(12) United States Patent
Hill

(10) Patent No.: US 6,246,481 B1
(45) Date of Patent: Jun. 12, 2001

(54) SYSTEMS AND METHODS FOR QUANTIFYING NONLINEARITIES IN INTERFEROMETRY SYSTEMS

(75) Inventor: Henry A. Hill, Tucson, AZ (US)

(73) Assignee: Zygo Corporation, Middlefield, CT (US)

( * ) Notice: Subject to any disclaimer, the term of this patent is extended or adjusted under 35 U.S.C. 154(b) by 0 days.

(21) Appl. No.: 09/583,368

(22) Filed: May 30, 2000

Related U.S. Application Data

(63) Continuation-in-part of application No. 09/557,338, filed on Apr. 24, 2000.
(60) Provisional application No. 60/166,639, filed on Nov. 19, 1999.

(51) Int. Cl.$^7$ .......................................... G01B 9/02
(52) U.S. Cl. ............................. 356/487; 356/498
(58) Field of Search .................... 356/484, 485, 356/486, 487, 496, 498

(56) References Cited

U.S. PATENT DOCUMENTS 6,137,574 * 10/2000 Hill ...................................... 356/351

\* cited by examiner

Primary Examiner—Robert H. Kim
Assistant Examiner—Andrew H. Lee
(74) Attorney, Agent, or Firm—Fish & Richardson P.C.

(57) ABSTRACT

The invention features interferometry systems and methods that quantify nonlinearities, e.g., cyclic errors, in an interference signal produced by an interferometry system. The systems and methods analyze interference signals for each of multiple Doppler shifts to thereby resolve nonlinearities that may otherwise overlap spectrally with a dominant interference signal, and also, to interpolate the contributions of the nonlinearities to measurements at different Doppler shifts. The time-varying interference signal or the phase extracted from the time-varying interference signal is Fourier transformed and at least some of the nonlinearities are associated with peaks in the square modulus of the Fourier transformed signal (i.e., the power spectrum). The amplitude and phase of the Fourier transform at the frequency of each such peak are used to quantify the associated nonlinearity. The quantified nonlinearities are used to correct optical path length measurements by the system. Changes in the magnitude of one or more of the quantified nonlinearities can also be used to identify degradation of a component of the interferometry system.

27 Claims, 22 Drawing Sheets

SYSTEMS AND METHODS FOR QUANTIFYING NONLINEARITIES IN INTERFEROMETRY SYSTEMS

CROSS-REFERENCE TO RELATED APPLICATIONS

This application is a continuation-in-part of parent application Ser. No. 09/557,338 filed Apr. 24, 2000, which claims priority from provisional application No. 60/166,639 filed Nov. 19, 1999. The contents of the parent application and the provisional application are incorporated herein by reference.

BACKGROUND OF THE INVENTION

This invention relates to interferometers, e.g., displacement measuring and dispersion interferometers that measure displacements of a measurement object such as a mask stage or a wafer stage in a lithography scanner or stepper system, and also interferometers that monitor wavelength and determine intrinsic properties of gases.

Displacement measuring interferometers monitor changes in the position of a measurement object relative to a reference object based on an optical interference signal. The interferometer generates the optical interference signal by overlapping and interfering a measurement beam reflected from the measurement object with a reference beam reflected from the reference object.

In many applications, the measurement and reference beams have orthogonal polarizations and different frequencies. The different frequencies can be produced, for example, by laser Zeeman splitting, by acousto-optical modulation, or internal to the laser using birefringent elements or the like. The orthogonal polarizations allow a polarizing beam splitter to direct the measurement and reference beams to the measurement and reference objects, respectively, and combine the reflected measurement and reference beams to form overlapping exit measurement and reference beams. The overlapping exit beams form an output beam that subsequently passes through a polarizer. The polarizer mixes polarizations of the exit measurement and reference beams to form a mixed beam. Components of the exit measurement and reference beams in the mixed beam interfere with one another so that the intensity of the mixed beam varies with the relative phase of the exit measurement and reference beams. A detector measures the time-dependent intensity of the mixed beam and generates an electrical interference signal proportional to that intensity. Because the measurement and reference beams have different frequencies, the electrical interference signal includes a "heterodyne" signal having a beat frequency equal to the difference between the frequencies of the exit measurement and reference beams. If the lengths of the measurement and reference paths are changing relative to one another, e.g., by translating a stage that includes the measurement object, the measured beat frequency includes a Doppler shift equal to $2vnp/\lambda$, where $v$ is the relative speed of the measurement and reference objects, $\lambda$ is the wavelength of the measurement and reference beams, n is the refractive index of the medium through which the light beams travel, e.g., air or vacuum, and p is the number of passes to the reference and measurement objects. Changes in the relative position of the measurement object correspond to changes in the phase of the measured interference signal, with a $2\pi$ phase change substantially equal to a distance change L of $\lambda/(np)$, where L is a round-trip distance change, e.g., the change in distance to and from a stage that includes the measurement object.

Unfortunately, this equality is not always exact. Many interferometers include nonlinearities such as what are known as "cyclic errors." The cyclic errors can be expressed as contributions to the phase and/or the intensity of the measured interference signal and have a sinusoidal dependence on the change in optical path length pnL. In particular, the first order cyclic error in phase has a sinusoidal dependence on $(2\pi pnL)/\lambda$ and the second order cyclic error in phase has a sinusoidal dependence on $2(2\pi nL)/\lambda$. Higher order cyclic errors can also be present.

Cyclic errors can be produced by "beam mixing," in which a portion of an input beam that nominally forms the reference beam propagates along the measurement path and/or a portion of an input beam that nominally forms the measurement beam propagates along the reference path. Such beam mixing can be caused by ellipticity in the polarizations of the input beams and imperfections in the interferometer components, e.g., imperfections in a polarizing beam splitter used to direct orthogonally polarized input beams along respective reference and measurement paths. Because of beam mixing and the resulting cyclic errors, there is not a strictly linear relation between changes in the phase of the measured interference signal and the relative optical path length pnL between the reference and measurement paths. If not compensated, cyclic errors caused by beam mixing can limit the accuracy of distance changes measured by an interferometer. Cyclic errors can also be produced by imperfections in transmissive surfaces that produce undesired multiple reflections within the interferometer and imperfections in components such as retroreflectors and/or phase retardation plates that produce undesired ellipticities in beams in the interferometer. For a general reference on the theoretical cause of cyclic error, see, for example, C. W. Wu and R. D. Deslattes, "Analytical modelling of the periodic nonlinearity in heterodyne interferometry," *Applied Optics*, 37, 6696–6700, 1998.

In dispersion measuring applications, optical path length measurements are made at multiple wavelengths, e.g., 532 nm and 1064 nm, and are used to measure dispersion of a gas in the measurement path of the distance measuring interferometer. The dispersion measurement can be used to convert the optical path length measured by a distance measuring interferometer into a physical length. Such a conversion can be important since changes in the measured optical path length can be caused by gas turbulence and/or by a change in the average density of the gas in the measurement arm even though the physical distance to the measurement object is unchanged. In addition to the extrinsic dispersion measurement, the conversion of the optical path length to a physical length requires knowledge of an intrinsic value of the gas. The factor $\Gamma$ is a suitable intrinsic value and is the reciprocal dispersive power of the gas for the wavelengths used in the dispersion interferometry. The factor $\Gamma$ can be measured separately or based on literature values. Cyclic errors in the interferometer also contribute to dispersion measurements and measurements of the factor $\Gamma$. In addition, cyclic errors can degrade interferometric measurements used to measure and/or monitor the wavelength of a beam.

SUMMARY OF THE INVENTION

The invention features interferometry systems and methods that quantify nonlinearities, e.g., cyclic errors, in an interference signal. The nonlinearities are caused by properties of the interferometry system such as beam mixing, multiple reflections, and nonlinear signal processing electronics. The nonlinearities produce additional terms in the interference signal that cause the phase of the interference signal to deviate from a linear relationship with the optical path length difference. The systems and methods allow the accuracy of displacement, wavelength, and dispersion measurements to be improved by correcting the measurements for the contribution of the nonlinearities. Moreover, sources of nonlinearity not previously recognized have been identified and formalized.

The systems and methods analyze multiple measurements of an interference signal corresponding to different optical path length differences to quantify the nonlinearities. In particular embodiments, the time-varying interference signal or the phase extracted from the time-varying interference signal is Fourier transformed and at least some of the nonlinearities are associated with peaks in the square modulus of the Fourier transformed signal (i.e., the power spectrum). The amplitude and phase of the Fourier transform at the frequency of each such peak are used to quantify the associated nonlinearity. The frequency of each peak and whether it can be resolved typically depends on the rate of change of the optical path length difference, i.e., on the Doppler shift. Thus, the systems and methods often analyze multiple time-varying interference signals for each of multiple Doppler shifts to thereby resolve nonlinearities that may otherwise remain hidden, and also, to interpolate the contributions of the nonlinearities to measurements at different Doppler shifts. For example, the contribution of the nonlinearities can be interpolated for measurements when the measurement object is stationary or changing direction, i.e., when the Doppler shift is zero or is passing through zero.

In general, in one aspect, the invention features an interferometry system. The interferometry system includes: an interferometer which during operation directs two beams along separate paths and then combines the beams to produce an overlapping pair of exit beams, the separate paths defining an optical path length difference; a detector which responds to optical interference between the overlapping pair of exit beams and produces an interference signal s(t) indicative of the optical path length difference; and an analyzer coupled to the detector. The signal s(t) includes a dominant term having a frequency equal to the sum of the frequency splitting $\omega$ between the two beams, if any, and a Doppler shift $\dot{\phi}$ defined by the rate of change of the optical path length difference. Properties of the interferometry system cause the signal s(t) to further include additional terms each having a frequency not equal to the sum of the frequency splitting $\omega$ and the Doppler shift $\dot{\phi}$. During operation the analyzer: i) quantifies at least one of the additional terms based on values of s(t) for which the value of the Doppler shift causes the dominant term and the at least one additional term to be separated spectrally; and ii) uses the quantified at least one additional term to estimate a change in the optical path length difference corresponding to another value of s(t) for which the value of the Doppler shift causes the dominant term and the at least one additional term to overlap spectrally.

The interferometry system can include any of the following features.

The detector can include a photodetector, an amplifier, and an analog-to-digital converter. The frequency splitting between the two beams can be nonzero. The at least one of the additional terms can include a plurality of the additional terms.

To quantify the at least one additional term, the analyzer can calculate the Doppler shift $\dot{\phi}$ for the values of s(t) based on the expression s(t) $\cos(\omega t+\phi+\zeta_{1,0,1,0})$+NL, where NL is an initial quantification of the additional terms, and where $\phi$=Lkn, L is the physical path length difference, k is a wavenumber, n is a refractive index, $\omega$ is the angular frequency splitting between the two beams, t is time, and $\zeta_{1,0,1,0}$ is a phase-offset. The initial quantification can be NL=0.

The analyzer can quantify the at least one additional term by estimating corresponding coefficients of a representation of s(t) that accounts for the additional terms. For example, the representation of s(t) can be expressed as:

$$s(t) = a_{1,0,1,0}\cos(\omega t + \varphi + \zeta_{1,0,1,0}) +$$

$$\sum_{u,u',p,p^+} a_{u,u',p,p^+}\cos(u\omega t + \omega'_{u'}t + p\varphi - p^+\varphi^+ + \zeta_{u,u',p,p^+}) +$$

$$\sum_q (a_{1,0,1,0})^q \begin{cases} B_{1,0,1,0,q,q}\cos[q(\omega t+\varphi)+\zeta_{1,0,1,0,q,q}] + \\ B_{1,0,1,0,q,q-2}\cos[(q-2)(\omega t+\varphi)+\zeta_{1,0,1,0,q,q-2}] + \\ \ldots + \\ B_{1,0,1,0,q,q_R}\cos[q_R(\omega t+\varphi)+\zeta_{1,0,1,0,q,q_R}] \end{cases} +$$

$\ldots$, $u$=0 or 1; $u'$=0,1, . . . ; $\omega'_0$=0;

$p,p^+$=0,1, . . . , $w_{2,1}/w_{2,2}$, $p^+ \neq 0$ if $p$=1 and $u$=1, $w_{2,1}, w_{2,2}$=1,2, . . . , $w_{2,1} \neq w_{2,2}$, $q$=2,3 . . . , $q_R$=0 for $q$ even, 1 for $q$ odd where $\phi$=Lkn, $\phi^+$=Lk$^+$n, k=$2\pi/\lambda$, k$^+$=$2\pi[(1/\lambda)+(\omega/2\pi c)]$, wherein $\omega$ is the angular frequency splitting between the two beams, $\omega'_{u'}$ are frequencies not equal to $\omega$ caused by at least one of the detector, the analyzer, and a source for the two beams, L is the physical path length difference, $\lambda$ is the wavelength of the beams in the first set, n is a refractive index, c is the speed of light in vacuum, and t is time. The dominant term corresponds to $a_{1,0,1,0}\cos(\omega t+\phi+\zeta_{1,0,1,0})$ and the additional terms correspond to the remaining terms. The amplitudes $a_v$ and $B_v$ and phases $\zeta_v$ define the coefficients for the representation of s(t), the subscript v denoting a general index.

To quantify the at least one additional term, the analyzer can calculate a frequency spectrum corresponding to a set of the values of s(t), and then estimate the coefficients for the at least one additional term based on the amplitude and phase of the frequency spectrum at an angular frequency $\omega$ equal to the derivative with respect to time of the argument of one of the sinusoids in the representation of s(t) not corresponding to the dominant term, or an alias $\omega_A$ of $\omega$. For example, the frequency spectrum can be the Fourier transform of the set of values of s(t). Alternatively, the frequency spectrum can be the Fourier transform of $\alpha(t)$, where s(t) is expressed as s(t)=A(t)cos($\alpha$(t)), and $\alpha(t)$ is the phase of s(t). If the analyzer estimates the coefficients for the at least one additional term based on the amplitude and phase of the frequency spectrum at the alias $\omega_A$ of $\omega$, the alias frequency can be expressed as $\omega_A = (-1)^r \omega - [(-1)^r(r+(\frac{1}{2}))-(\frac{1}{2})]\omega_{Ny}$, for a positive integer of r that satisfies $r\omega_{N_y} < \omega < (r+1)\omega_{N_y}$, where the detector has a sampling rate that defines the Nyquist frequency $\omega_{N_y}$. To estimate the coefficients, for example, $\omega$ can be one of $\omega + \omega'_u$, for $u' \neq 0$; $\omega$ can be one of $q(\omega + \dot\phi)$; or $\omega$ can be one of $u\omega + p\dot\phi + p^+\dot\phi$, for $p \neq 1$ and, $p \neq 0$ when $u = 0$.

To estimate the coefficients for the at least one additional term, the analyzer can also normalize the amplitude and phase of the frequency spectrum at the angular frequency $\omega$ to account for at least one non-zero, derivative of $\dot\phi$.

The analyzer can quantify the at least one additional term based on a first set of values of s(t) for which the Doppler shift is sufficiently large to spectrally separate the additional frequency from the dominant frequency, and then further quantify the at least one additional term based on at least a second set of values of s(t) for which the Doppler shift is different from that of the first set of values and sufficiently large to spectrally separate the additional frequency from the dominant frequency. The analyzer can then quantify the at least one additional term as a function of the Doppler shift by interpolating values of the quantification for each set of values of s(t).

The analyzer can determine the dependence of each of the estimated coefficients on the Doppler shift based on multiple sets of values of s(t), each set corresponding to a different Doppler shift.

The at least one additional term can be a plurality of the additional terms, to quantify the plurality of the additional terms, the analyzer can estimate the coefficients for each of the plurality of the additional terms based on the amplitude and phase of the frequency spectrum at a corresponding plurality of angular frequencies $\omega_v$ or their aliases. Each $\omega_v$ equals the derivative with respect to time of the argument of one of the sinusoids in the representation of s(t) not corresponding to the dominant term. In such embodiments, the analyzer can estimate coefficients corresponding to at least some of $B_{1,0,1,0,q,q-2j}$ and $\zeta_{1,0,1,0,q,q-2j}$, where q is odd and j is a nonnegative integer less than $q/2-1$, to determine $B_{1,0,1,0,q,1}$ and $\zeta_{1,0,1,0,q,1}$ (e.g., zero-frequency-shift errors).

The analyzer can estimate the change in the optical path length difference corresponding to the other value of s(t) by determining a value for $\phi = Lkn$ that is self-consistent with s(t) $\cos(\omega t + \phi + \zeta_{1,0,1,0}) + NL(\phi,\dot\phi)$. NL expresses the quantified at least one additional term, wherein L is the physical path length difference, k is a wavenumber, n is a refractive index, $\omega$ is the angular frequency difference between the two beams, t is time, and $\zeta_{1,0,1,0}$ is a phase-offset. For example, the analyzer can determine the value for $\phi$ by iteratively improving an estimate for the value for $\phi$.

The analyzer can use the estimated change in optical path length to determine a change in physical path length, to determine a change in dispersion, to determine an intrinsic value a gas, or to monitor the wavelength of the beams.

In general, in another aspect, the invention features an interferometry system including: an interferometer which during operation directs two beams along separate paths and then combines the beams to produce an overlapping pair of exit beams, the separate paths defining an optical path length difference; a detector which responds to optical interference between the overlapping pair of exit beams and produces a signal s(t) indicative of the interference; and an analyzer coupled to the detector. The signal s(t) is a function of the optical path length difference. Properties of the interferometry system cause the signal s(t) to deviate from the expression $s(t) = a \cos(\omega t + \phi + \zeta)$, where $\phi = Lkn$, L is the physical path length difference, k is a wavenumber, n is a refractive index, $\omega$ is the angular frequency difference, if any, between the two beams, t is time, a is an amplitude that is constant with respect to $\phi$, and $\zeta$ is a phase offset that is constant with respect to $\phi$ and $\dot\phi$. During operation, the analyzer: i) Fourier transforms at least one set of values of s(t) for which the rate of change of the optical path length difference is not zero ($\dot\phi \neq 0$), the Fourier transform defining a power spectrum equal to the square modulus of the Fourier transform; ii) quantifies at least some of the deviations based on the amplitude and phase of the Fourier transform at frequencies that differ from $\omega + \dot\phi$ and correspond to peaks in the power spectrum; and iii) uses the quantified deviations to estimate a change in the optical path length difference corresponding to a particular value of s(t).

In general, in another aspect, the invention features an interferometry system including: an interferometer which during operation directs two beams along separate paths and then combines the beams to produce an overlapping pair of exit beams, the separate paths defining an optical path length difference; a detector which responds to optical interference between the overlapping pair of exit beams and produces a signal s(t) indicative of the interference; and an analyzer coupled to the detector. The signal s(t) is a function of the optical path length difference. Properties of the interferometry system cause the signal s(t) to deviate from the expression $s(t) = a \cos(\omega t + \phi + \zeta)$, where $\phi = Lkn$, L is the physical path length difference, k is a wavenumber, n is a refractive index, $\omega$ is the angular frequency difference, if any, between the two beams, t is time, a is an amplitude that is constant with respect to $\phi$, and $\zeta$ is a phase offset that is constant with respect to $\phi$ and $\dot\phi$, where s(t) can be expressed as $s(t) = A(t) \cos(\alpha(t))$, and $\alpha(t)$ is the phase of s(t). During operation, the analyzer: i) extracts the phase $\alpha(t)$ for s(t); ii) Fourier transforms at least one set of values of $\alpha(t)$ for which the rate of change of the optical path length difference is not zero ($\dot\phi \neq 0$), the Fourier transform defining a power spectrum equal to the square modulus of the Fourier transform; iii) quantifies at least some of the deviations based on the amplitude and phase of the Fourier transform at frequencies that differ from $\omega + \dot\phi$ and correspond to peaks in the power spectrum; and iv) uses the quantified deviations to estimate a change in the optical path length difference corresponding to a particular value of s(t).

In general, in another aspect, the invention features an interferometry system including: an interferometer which during operation directs two beams along separate paths and then combines the beams to produce an overlapping pair of exit beams, the separate paths defining an optical path length difference; a detector which responds to optical interference between the overlapping pair of exit beams and produces an interference signal s(t) indicative of the optical path length difference; an analyzer coupled to the detector; and an alert mechanism coupled to the analyzer. The signal s(t) includes a dominant term having a frequency equal to the sum of the frequency splitting $\omega$ between the two beams, if any, and a Doppler shift $\dot\phi$ defined by the rate of change of the optical path length difference. Properties of the interferometry system cause the signal s(t) to further include additional terms each having a frequency not equal to the sum of the frequency splitting $\omega$ and the Doppler shift $\dot\phi$. During operation, the analyzer monitors the frequencies of the signal s(t), and produces a signal indicative of system degradation when the amplitude of a frequency corresponding to one of the additional terms exceeds a threshold value. The alert mechanism is responsive to the system degradation signal.

The interferometry system can include any of the following features.

To alert an operator, the alert mechanism can include at least one of a visual display, a sound system, a warning light, and a printer.

To monitor the frequencies in s(t), the analyzer can Fourier transform at least one set of values for s(t). Alternatively, the analyzer can extract the phase $\alpha(t)$ of s(t) for a set of values of s(t), where s(t) is expressed as s(t)=A(t)cos($\alpha(t)$), and then Fourier transform the extracted phases to monitor the frequencies in it).

The analyzer can monitor the frequencies in s(t) based on values of s(t) for which the value of the Doppler shift causes the dominant term and at least one of the additional terms to be separated spectrally.

The signal s(t) can be expressed by the summation shown above with reference to an earlier aspect of the invention. To determine whether to produce the signal indicative of system degradation, the analyzer can compare the threshold value to the amplitude of one of frequencies $\omega+\omega'_{u'}$, for u'≠0, frequencies q($\omega+\phi$), or frequencies u$\omega$+p$\phi$+p$^+\phi$, for p≠1, and for p≠0 when u=0.

In general, in another aspect, the invention features an interferometry system including: a source which during operation provides a first set of two beams having a frequency splitting $\omega$ and a second set of two beams having a frequency splitting $\omega_T$ not equal to $\omega$; an interferometer which during operation directs the first beam of the first set and the first beam of the second set along a measurement path and the second beam of the first set and the second beam of the second set along a reference path, and then combines the two sets of beams to form an output beam, the measurement and reference paths defining an optical path length difference; a detector which responds to optical interference between the beams in the output beam and produces a signal S(t) indicative of the interference, the interference being a function of the optical path length difference; and an analyzer coupled to the detector. In the absence of the second set of beams, the signal S(t) equals s(t) which includes a dominant term at a frequency equal to the sum of the frequency splitting $\omega$ and a Doppler shift $\phi$ defined by the rate of change of the optical path length difference. Properties in the interferometry system cause zero-frequency-shift cyclic errors that contribute to s(t) at the same frequency as the dominant frequency. In the presence of the second set of beams, the properties that produce the zero-frequency-shift cyclic error contribution to s(t) produce a multiplet in the frequency spectrum of S(t), wherein the multiplet has adjacent peaks that are spaced by $\omega-\omega_T$. During operation the analyzer resolves frequencies in S(t) to identify the multiplet and quantifies at least one of the zero-frequency-shift cyclic errors based on the amplitude and phase of at least one of the peaks in the multiplet.

The interferometry system can include any of the following features.

The analyzer can quantify multiple zero-frequency-shift cyclic errors based on the amplitude and phase of each of multiple peaks in the multiplet. The analyzer can be further coupled to the source, and can selectively cause the source to provide the first set of beams and not the second set of beams to the interferometer. When the analyzer selectively causes the source to provide the first set of beams and not the second set of beams to the interferometer, the analyzer can determine the optical path length difference based on s(t) and at least one of the quantified zero-frequency-shift cyclic errors. Alternatively, the analyzer can determine the optical path length difference based on S(t) and at least one of the quantified zero-frequency-shift cyclic errors.

The analyzer can resolve frequencies in S(t) by Fourier transforming at least one set of values for S(t). Alternatively, S(t) is expressed as S(t)=$A_S$(t)cos($\alpha_S$(t)), $\alpha_S$(t) being the phase of S(t), and the analyzer can resolve the frequencies of S(t) by extracting the phase $\alpha_S$(t) from S(t) and Fourier transforming at least one set of values of $\alpha_S$(t).

The multiplet can include a peak at the dominant frequency. The frequency splittings can each be less than a Nyquist frequency $\omega_{N_y}$, where the detector samples values of S(t) at a rate that defines the Nyquist frequency. The difference between the average frequency of the first set of beams and the average frequency of the second set of beams can be more than the Nyquist frequency. For example, the frequency splittings can satisfy: $\omega<\omega_{N_y}$, $\omega_T<\omega_{N_y}$, and $|\omega-\omega_T|<<\omega$, e.g., $|\omega-\omega_T|<(\omega/100)$.

The source can include first and second lasers, the first set of beams derived from the first laser and the second set of beams derived from the second laser. Furthermore, the source can include first and second lasers and first and second acousto-optical modulators, the first set of beams derived from the first laser and the first acousto-optical modulator and the second set of beams derived from second laser and the second acousto-optical modulator. Alternatively, the source includes a laser and first and second acousto-optical modulators, wherein a first beam derived from the laser passes through first acousto-optical modulator to produce the first set of beams and a second beam derived from the laser passes through the second acousto-optical modulator to produce the second set of beams. For example, the first and second beams derived from the laser can correspond to adjacent longitudinal modes of the laser.

The analyzer can resolve the frequency multiplet in S(t) for each of multiple Doppler shifts and quantify the dependence of the quantified zero-frequency-shift cyclic on the Doppler shift. During operation the analyzer can produce a signal indicative of system degradation when the amplitude of the multiplet exceeds a threshold value. The system can further include an alert mechanism coupled to the analyzer that is responsive to the system degradation signal. For example, the alert mechanism can include at least one of a visual display, a sound speaker, a printer, and a warning light.

Finally, the signal s(t) can be expressed by the summation shown above with reference to an earlier aspect of the invention, in which case the quantified zero-frequency-shift cyclic error can correspond to $B_{1,0,1,q,1}$ and $\zeta_{1,0,1,q,1}$ for one of q=3,5,7 . . . .

In general, in another aspect, the invention features an interferometry system including an interferometer, a detector, and an analyzer. During operation, the interferometer directs two beams along separate paths and then combines the beams to produce an overlapping pair of exit beams, the separate paths defining an optical path length difference. The detector responds to optical interference between the overlapping pair of exit beams and produces an interference signal s(t) indicative of the optical path length difference. The signal s(t) includes a dominant term having a frequency equal to the sum of the frequency splitting $\omega$ between the two beams, if any, and a Doppler shift $\phi$ defined by the rate of change of the optical path length difference. Properties of the interferometry system causes the signal s(t) to further include additional terms each having a frequency not equal to the sum of the frequency splitting $\omega$ and the Doppler shift $\phi$. The analyzer is coupled to the detector, and during operation it: i) applies a window function to a sequence of values of the signal s(t); ii) Fourier transforms the windowed sequence of values, the Fourier transform defining a power spectrum equal to the square modulus of the Fourier transform; and iii) identifies at least one of the additional terms based on at least one peak in the power spectrum at a frequency not equal to the sum of the frequency splitting $\omega$ and the Doppler shift $\dot{\phi}$.

The interferometry system can include any of the following features.

The window function can reduce the amplitude of the sequence of values of s(t) as the sequence approaches either of its endpoints. Alternatively, or in addition, the window function can suppress the frequency equal to the sum of the frequency splitting $\omega$ and the Doppler shift $\dot{\phi}$ relative to a frequency of at least one of the additional terms.

Furthermore, during operation the analyzer can quantify at least one of the additional terms based on the amplitude and phase of the Fourier transform at the frequency of the at least one peak in the power spectrum. The analyzer can further use the quantified additional term to estimate a change in the optical path length difference corresponding to a particular value of s(t). The analyzer can also use the estimated change in optical path length difference to do at least one of determine a change in physical path length, determine a change in dispersion, determine an intrinsic value of a gas, and monitor the wavelength of the beams.

Also, the analyzer can further produce a signal indicative of system degradation when the amplitude of the identified additional term exceeds a threshold value, and the interferometry system can further includes an alert mechanism coupled to the analyzer and responsive to the system degradation signal. For example, the alert mechanism can include at least one of a visual display, a sound system, a warning light, and a printer.

In general, in another aspect, the invention features an interferometry system including an interferometer, a detector, and an analyzer. During operation, the interferometer directs two beams along separate paths and then combines the beams to produce an overlapping pair of exit beams, the separate paths defining an optical path length difference. The detector responds to optical interference between the overlapping pair of exit beams and produces an interference signal s(t) indicative of the optical path length difference. The signal s(t) includes a dominant term having a frequency equal to the sum of the frequency splitting $\omega$ between the two beams, if any, and a Doppler shift $\dot{\phi}$ defined by the rate of change of the optical path length difference. Properties of the interferometry system causes the signal s(t) to further include additional terms each having a frequency not equal to the sum of the frequency splitting $\omega$ and the Doppler shift $\dot{\phi}$. The analyzer is coupled to the detector and includes a low-pass filter. During operation, the analyzer: i) tracks the value of the Doppler shift based on the signal s(t); ii) calculates the frequency $\omega'_v$ of one of the additional terms based on the tracked value of the Doppler shift; iii) generates a first tuned-filter signal equal to $s(t)\cos(\omega'_v t)$ and a second tuned-filter signal equal to $s(t)\sin(\omega'_v t)$; and iv) passes the tuned-filter signals through the low-pass filter to quantify the additional term corresponding to $\omega'_v$.

The interferometry system can include any of the following features.

During operation, the analyzer can calculate the frequency $\omega'_v$ of one of the additional terms based on the tracked value of the Doppler shift and a Nyquist frequency defined by the sampling rate of the detector. The analyzer can also generate additional tuned-filter signals based on the frequency of at least one other additional term to quantify the at least one other additional term. The analyzer can also use the quantified additional term to estimate a change in the optical path length difference corresponding to a particular value of s(t). Furthermore, the analyzer can use the estimated change in optical path length difference to do at least one of determine a change in physical path length, determine a change in dispersion, determine an intrinsic value of a gas, and monitor the wavelength of the beams.

Also, the analyzer can further produce a signal indicative of system degradation when the amplitude of the quantified additional term exceeds a threshold value, and the system can further includes an alert mechanism coupled to the analyzer and responsive to the system degradation signal. For example, the alert mechanism can include at least one of a visual display, a sound system, a warning light, and a printer.

In general, in another aspect, the invention features an interferometry system including an interferometer, a detector, and an analyzer. During operation, the interferometer directs two beams along separate paths and then combines the beams to produce an overlapping pair of exit beams, the separate paths defining an optical path length difference. The detector responds to optical interference between the overlapping pair of exit beams and produces an interference signal s(t) indicative of the optical path length difference. The signal s(t) includes a dominant term having a frequency equal to the sum of the frequency splitting $\omega$ between the two beams, if any, and a Doppler shift $\dot{\phi}$ defined by the rate of change of the optical path length difference. Properties of the interferometry system causes the signal s(t) to further include additional terms each having a frequency not equal to the sum of the frequency splitting $\omega$ and the Doppler shift $\dot{\phi}$. The analyzer is coupled to the detector, and during operation it: i) provides a quantification for at least some of the additional terms; ii) Fourier transforms at least one set of values of s(t); and iii) estimates a value for the optical path length difference based on the amplitude and phase of the Fourier transform at the frequency $\omega+\dot{\phi}$ and values of the quantification for the additional terms that contribute to the Fourier transform at the frequency $\omega+\dot{\phi}$ based on the Doppler shift $\dot{\phi}$ corresponding to the set of values of s(t).

The interferometry system can include any of the following features.

During operation, the analyzer can identify which of the additional terms in the quantification contribute to the Fourier transform at the frequency $\omega+\dot{\phi}$ based on the Doppler shift $\dot{\phi}$ corresponding to the set of values of s(t) and a Nyquist frequency corresponding to the sampling rate of the detector. Also, the analyzer can use the estimated change in optical path length difference to do at least one of determine a change in physical path length, determine a change in dispersion, determine an intrinsic value of a gas, and monitor the wavelength of the beams.

In general, in another aspect, the invention features a lithography system for use in fabricating integrated circuits on a wafer, the system including: a stage for supporting the wafer; an illumination system for imaging spatially patterned radiation onto the wafer; a positioning system for adjusting the position of the stage relative to the imaged radiation; and any of the interferometry systems described above for measuring the position of the stage.

In general, in another aspect, the invention features a lithography system for use in fabricating integrated circuits on a wafer, the system including: a stage for supporting the wafer; and an illumination system including a radiation source, a mask, a positioning system, a lens assembly, and any of the interferometry systems described above, wherein during operation the source directs radiation through the mask to produce spatially patterned radiation, the positioning system adjusts the position of the mask relative to the radiation from the source, the lens assembly images the spatially patterned radiation onto the wafer, and the interferometry system measures the position of the mask relative to the radiation from the source.

In general, in another aspect, the invention features a beam writing system for use in fabricating a lithography mask, the system including: a source providing a write beam to pattern a substrate; a stage supporting the substrate; a beam directing assembly for delivering the write beam to the substrate; a positioning system for positioning the stage and beam directing assembly relative one another; and any of the interferometry systems describe for measuring the position of the stage relative to the beam directing assembly.

In further aspects, the invention features interferometry method, lithography methods, and beam writing methods based on the systems described above. General aspects of such methods are described below.

In one aspect, the invention features an interferometry method for use with an interferometry system. The interferometry method includes: directing two beams along separate paths; combining the beams to produce an overlapping pair of exit beams, the separate paths defining an optical path length difference; measuring optical interference between the overlapping pair of exit beams to produce an interference signal $s(t)$ indicative of the optical path length difference, the signal $s(t)$ including a dominant term having a frequency equal to the sum of the frequency splitting $\omega$ between the two beams, if any, and a Doppler shift $\dot{\phi}$ defined by the rate of change of the optical path length difference, wherein properties of the interferometry system causes the signal $s(t)$ to further include additional terms each having a frequency not equal to the sum of the frequency splitting $\omega$ and the Doppler shift $\dot{\phi}$; quantifying at least one of the additional terms based on values of $s(t)$ for which the value of the Doppler shift causes the dominant term and the at least one additional term to be separated spectrally; and using the quantified at least one additional term to estimate a change in the optical path length difference corresponding to another value of $s(t)$ for which the value of the Doppler shift causes the dominant term and the at least one additional term to overlap spectrally.

In another aspect, the invention features an interferometry method for use with an interferometry system. The interferometry method includes: directing two beams along separate paths; combining the beams to produce an overlapping pair of exit beams, the separate paths defining an optical path length difference; measuring optical interference between the overlapping pair of exit beams to produce an interference signal $s(t)$ indicative of the optical path length difference, the signal $s(t)$ including a dominant term having a frequency equal to the sum of the frequency splitting $\omega$ between the two beams, if any, and a Doppler shift $\dot{\phi}$ defined by the rate of change of the optical path length difference, wherein properties of the interferometry system causes the signal $s(t)$ to further include additional terms each having a frequency not equal to the sum of the frequency splitting $\omega$ and the Doppler shift $\dot{\phi}$; monitoring the frequencies of the signal $s(t)$; and alerting an operator when the amplitude of a frequency corresponding to one of the additional terms exceeds a threshold value.

In another aspect, the invention features an interferometry method for use with an interferometry system. The interferometry method includes: providing a first set of two beams having a frequency splitting $\omega$ and a second set of two beams having a frequency splitting $\omega_T$ not equal to $\omega$; directing the first beam of the first set and the first beam of the second set along a measurement path and the second beam of the first set and the second beam of the second set along a reference path; combining the two sets of beams to form an output beam, the measurement and reference paths defining an optical path length difference; measuring optical interference between the beams in the output beam to produce a signal $S(t)$ indicative of the interference, the interference being a function of the optical path length difference, wherein in the absence of the second set of beams, the signal $S(t)$ equals $s(t)$ which includes a dominant term at a frequency equal to the sum of the frequency splitting $\omega$ and a Doppler shift $\dot{\phi}$ defined by the rate of change of the optical path length difference, wherein properties in the interferometry system cause zero-frequency-shift cyclic errors that contribute to $s(t)$ at the same frequency as the dominant frequency, and in the presence of the second set of beams, the properties that produce the zero-frequency-shift cyclic error contribution to $s(t)$ produce a multiplet in the frequency spectrum of $S(t)$, wherein the multiplet has adjacent peaks that are spaced by $\omega-\omega_T$; resolving frequencies in $S(t)$ to identify the multiplet; and quantifying at least one of the zero-frequency-shift cyclic errors based on the amplitude and phase of at least one of the peaks in the multiplet.

In general, in another aspect, the invention features an interferometry method including: directing two beams along separate paths; combining the beams to produce an overlapping pair of exit beams, the separate paths defining an optical path length difference; measuring optical interference between the overlapping pair of exit beams to produce an interference signal $s(t)$ indicative of the optical path length difference, the signal $s(t)$ including a dominant term having a frequency equal to the sum of the frequency splitting $\omega$ between the two beams, if any, and a Doppler shift $\dot{\phi}$ defined by the rate of change of the optical path length difference, wherein properties of the interferometry system causes the signal $s(t)$ to further include additional terms each having a frequency not equal to the sum of the frequency splitting $\omega$ and the Doppler shift $\dot{\phi}$; applying a window function to a sequence of values of the signal $s(t)$; Fourier transforming the windowed sequence of values, the Fourier transform defining a power spectrum equal to the square modulus of the Fourier transform; and identifying at least one of the additional terms based on at least one peak in the power spectrum at a frequency not equal to the sum of the frequency splitting $\omega$ and the Doppler shift $\dot{\phi}$.

In general, in another aspect, the invention features an interferometry method including: directing two beams along separate paths; combining the beams to produce an overlapping pair of exit beams, the separate paths defining an optical path length difference; measuring optical interference between the overlapping pair of exit beams to produce an interference signal $s(t)$ indicative of the optical path length difference, the signal $s(t)$ including a dominant term having a frequency equal to the sum of the frequency splitting $\omega$ between the two beams, if any, and a Doppler shift $\dot{\phi}$ defined by the rate of change of the optical path length difference, wherein properties of the interferometry system causes the signal $s(t)$ to further include additional terms each having a frequency not equal to the sum of the frequency splitting $\omega$ and the Doppler shift $\dot{\phi}$; tracking the value of the Doppler shift based on the signal $s(t)$; calculating the frequency $\omega'_v$ of one of the additional terms based on the tracked value of the Doppler shift; generating a first tuned-filter signal equal to $s(t)\cos(\omega'_v t)$ and a second tuned-filter signal equal to $s(t)\sin(\omega'_v t)$; and passing the tuned-filter signals through a low-pass filter to quantify the additional term corresponding to $\omega'_v$.

In general, in another aspect, the invention features, an interferometry system including: directing two beams along separate paths; combining the beams to produce an overlapping pair of exit beams, the separate paths defining an optical path length difference; measuring optical interference between the overlapping pair of exit beams to produce an interference signal s(t) indicative of the optical path length difference, the signal s(t) including a dominant term having a frequency equal to the sum of the frequency splitting ω between the two beams, if any, and a Doppler shift φ defined by the rate of change of the optical path length difference, wherein properties of the interferometry system causes the signal s(t) to further include additional terms each having a frequency not equal to the sum of the frequency splitting ω and the Doppler shift φ; providing a quantification for at least some of the additional terms; Fourier transforming at least one set of values of s(t); and estimating a value for the optical path length difference based on the amplitude and phase of the Fourier transform at the frequency ω+φ and values of the quantification for the additional terms that contribute to the Fourier transform at the frequency ω+φ based on the Doppler shift φ corresponding to the set of values of s(t).

In a further aspect, the invention features a lithography method including: supporting a wafer on a stage; imaging spatially patterned radiation onto the wafer; adjusting the position of the stage relative to the imaged radiation; and using any of the interferometry methods described above to measure the relative position of the stage.

In another aspect, the invention features a lithography method including: supporting a wafer on a stage; directing radiation from a source through a mask to produce spatially patterned radiation; positioning the mask relative to the radiation; using any of the interferometry methods described above to measures the position of the mask relative to the radiation; and imaging the spatially patterned radiation onto the wafer.

In another aspect, the invention features a beam writing method including: providing a write beam to pattern a substrate; supporting the substrate on a stage;

delivering the write beam to the substrate; positioning the stage relative to the write beam; and using any of the interferometry methods describe above to measure the relative position of the stage.

Embodiments of the invention can include many advantages. For example, they can identify and quantify nonlinearities that can otherwise degrade the interferometric displacement or dispersion measurement. The quantified nonlinearities can be used to correct interferometric measurements and thereby significantly improve their accuracy. Moreover, by using the systems of and methods of the invention, interferometers can be made more cheaply because expensive optical components that reduce the likelihood of nonlinearities are not necessary, similarly, nonlinearities in the detection electronics need not be minimized. In addition, by using the systems and methods of the invention, a degradation in performance of one or more components of an interferometer can be detected and corrective measures implemented, for example, as part of a programmed maintenance, thus reducing the potential for a significant loss in acceptable operation time as a consequence of operating the interferometer in an unacceptable mode. By quantifying the nonlinearities, embodiments of the invention can permit rapid correction of the interferometric measurement, such as is usually necessary during online applications when the measurement object is rapidly scanned or stepped. The quantification of the nonlinearities and its use in correcting interferometric measurements can be applied to optical distance measurements, dispersion measurements, wavelength measurements, and measurements of intrinsic optical properties of the gas in the measurement arm of the interferometer such as the reciprocal dispersive power Γ. In addition, the interferometry systems can be used in lithography and mask writing applications.

Other features and advantages will be apparent from the following detailed description and from the claims.

BRIEF DESCRIPTION OF THE DRAWINGS

FIGS. 2b and 2c are schematic diagrams of various embodiments for an electronic processor in the interferometry system of FIG. 2a.

FIGS. 3b and 3c are schematic diagrams of various embodiments for an electronic processor in the interferometry system of FIG. 3a.

FIGS. 4b and 4c are schematic diagrams of electronic processors in the interferometry system of FIG. 4a.

DETAILED DESCRIPTION

Nonlinearities such as cyclic errors can degrade the accuracy of displacement and/or dispersion measurements extracted from interferometric data. The nonlinearities can arise from imperfections in the light source and the interferometer optics, and from nonlinearity in the detection electronics such as the photoelectric detector, amplifier, or analog-to-digital converter. Although it might be possible to minimize the causes of such nonlinearities, one aspect of the present invention proposes to improve the accuracy of the interferometric measurement by quantifying the nonlinearities and, using the quantified nonlinearities, correcting the interferometric signal (or information derived from the interferometric signal) for the nonlinearities to thereby improve the accuracy of the measurement of interest, e.g., displacement or dispersion. Another aspect of the present invention proposes to detect a degradation of certain components of an interferometer system by quantifying nonlinearities of the interferometer system, and monitoring whether the components are degrading based on a change in the magnitude of the quantified nonlinearities. Interferometry systems that provide such features will now be described generally, and thereafter, more specific embodiments will be described in greater detail.

Figure 1:
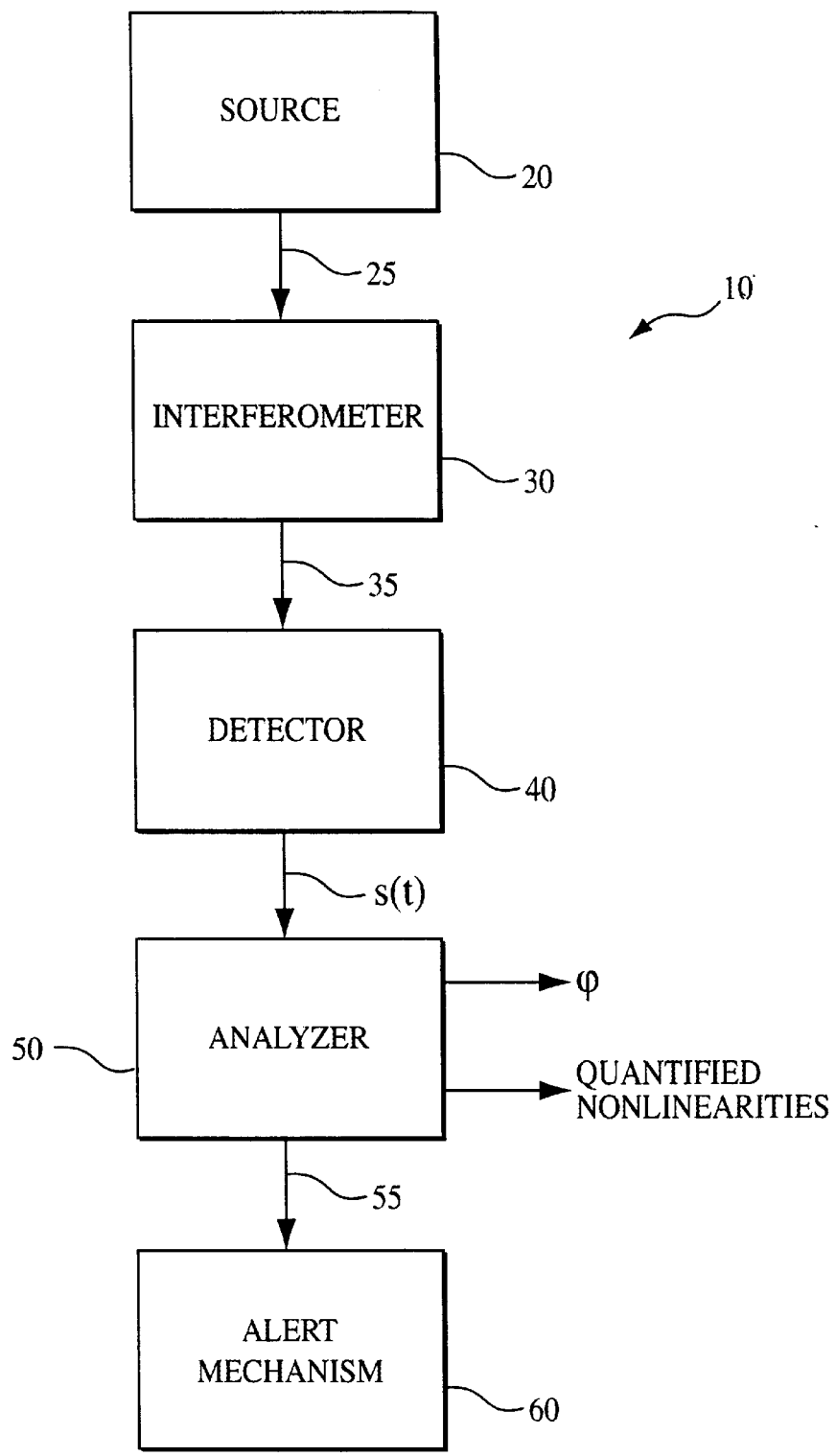
FIG. 1 is a general schematic diagram of an interferometry system that quantifies and/or monitors nonlinearities caused by properties of the system.

Referring to FIG. 1, an interferometry system 10 includes a source 20, an interferometer 30, a detector 40, and an analyzer 50. Source 20 includes a laser for providing one or more beams 25 to interferometer 30. For dispersion interferometry, beams 25 include at least two beams at different wavelengths, e.g., 1064 nm and 532 nm. For optical path displacement measurements, a single wavelength is sufficient. When using heterodyne interferometry techniques at one or more different wavelengths, source 20 introduces a frequency splitting between components of each beam at the one or more different wavelengths. For example, one or more acousto-optical modulators can be used to introduce the frequency splitting, or alternatively, the source can include a Zeeman-split laser to produce the frequency splitting. Often the frequency-split components are made to have orthogonal polarizations. The frequency-split components can be sent to interferometer 30, where they are separated into measurement and reference beams. Alternatively, source 20 can spatially separate the frequency-split components and send the spatially separated components to interferometer 30, where they become measurement and reference beams.

Interferometer 30 can be any type of interferometer, e.g., a differential plane mirror interferometer, a double-pass interferometer, or a Michelson-type interferometer. The interferometer can be designed to monitor, for example, changes in optical path length, changes physical path length, changes in refractive index, changes in wavelength of a beam, or intrinsic gas properties along a path length. The interferometer directs a reference beam along a reference path (which may contact a reference object) and a measurement beam along a measurement path contacting a measurement object (e.g., a lithography stage), and then combines the reference and measurement beams to form an overlapping pair of exit beams 35. In dispersion interferometry applications, there are overlapping pairs of exit beams for each of the different wavelengths.

The interference between the overlapping pair of exit beams contains information about the relative difference in optical path length between the reference and measurement paths. In some embodiments, the reference path is fixed and therefore changes in the optical path length difference correspond to changes in the optical path length of the measurement path. In other embodiments, however, the optical path length of both the reference and measurement paths can be changing. For example, the reference path can contact a reference object (e.g., a column reference), that may move relative to the interferometer. In this latter case, the changes in the optical path length difference correspond to changes in the position of the measurement object relative to the reference object.

When the reference and measurement beams have orthogonal polarizations, the intensity of at least one intermediate polarization of the overlapping pair of exit beams is selected to produce the optical interference. For example, a polarizer can be positioned within interferometer 30 to mix the polarizations of the overlapping pair of exit beams, which is then sent to detector 40. Alternatively, the polarizer can be positioned within detector 40. The detector 40 measures the intensity of the selected polarization of the overlapping pair of exit beams to produce the interference signal. Portions of the beams can be combined with one another before being directed along the reference and measurement paths to provide a reference pair of a overlapping exit beams, which is used to provide a reference interference signal.

Detector 40 includes a photodetector, which measures the intensity of the selected polarization of the overlapping pair of exit beams, and electronics such as a preamplifier and an analog-to-digital converter, which amplify the output from the photodetector and produce a digital signal s(t) corresponding to the optical interference. In dispersion interferometry applications, digital signals s(t) are produced for each of the overlapping pair of exit beams (which correspond to different wavelengths) by using multiple photodetection channels within detector 40.

The signal s(t), absent any nonlinearities and ignoring a constant offset intensity, can be expressed as $s(t)=a\cos(\omega t+\phi+\zeta)$, where $\phi=Lkn$, L is the physical path length difference between the reference and measurement paths, k is the wavenumber of the measurement beam, n is the refractive index within the interferometer, $\omega$ is the angular split frequency difference between the measurement and reference beams before introduction of any Doppler shift, t is time, a is an amplitude that is constant with respect to $\phi$, and $\zeta$ is a phase offset that is constant with respect to $\phi$ and $\dot{\phi}$, where $\dot{\phi}$ is the first derivative of $\phi$ with respect to time. In homodyne applications, the split frequency difference between beam components in the expression for s(t) is zero, i.e. $\omega=0$, and to accurately separate background signal from the optical inteference, detector 40 includes multiple photodetection channels to measure interference for multiple phase offsets, the phase offsets being introduced within detector 40.

The signal s(t) is sent to analyzer 50, which extracts phase $\phi=Lkn$ from s(t) using a reference phase provided by the source of the heterodyne frequency split difference or the reference interference signal, the analyzer can determine changes in the optical length difference between the measurement and reference paths. Furthermore, using the signals corresponding to additional wavelengths, the analyzer can make dispersion measurements, determine physical path length difference measurements, and/or measure intrinsic properties of the gas in the measurement path.

Analyzer 50 includes a computer or digital processor for performing the phase extraction and other analysis steps described below relating to quantification of nonlinearities. For example, the numerical and symbolic steps described herein can be converted into a digital program executed, e.g., on a digital signal processor (DSP) according to methods well known in the art. The digital program can be stored on a computer readable medium such as a hard disk and can be executable by the computer processors in the analyzer. Alternatively, the appropriate analysis steps can be converted into a digital program that is hardwired into dedicated electronic circuits within the analyzer that executes the steps. Methods for generating such dedicated electronic circuits based on a given numerical or symbolic analysis procedure are also well known in the art.

Beam mixing and intensity fluctuations in beam 25, imperfections in interferometer 30, and nonlinearity in detector 40 and the electronics therein, can all produce nonlinearities in the signal s(t). The nonlinearities cause the signal s(t) to deviate from the expression s(t)=a cos($\omega$t+$\phi$+ $\zeta$), e.g., the cyclic errors described above can introduce additional terms to the expression such as $a_{p1}$ cos($\omega$t+p$\phi$+ $\zeta_{p1}$) where p=2,3, . . . . Moreover, p can take on fractional values when there are multiple passes within interferometer 30. Intensity fluctuations in beam 25 can introduce additional terms to the expression such as $a_{u'p1}$ cos($\omega$t+$\omega'_{u'}$t+ p$\phi$+$\zeta_{u'p1}$) where u'=0,1, . . . . The angular frequencies $\omega_{u'}$ can arise, for example, from the switching frequencies of power supplies in source 20. In heterodyne applications, beam mixing can also produce additional terms such as $a_{p0}$ cos (p$\phi$+$\zeta_{10}$), and there can also be terms that address the small wavevector difference between the measurement and reference beams associated with the heterodyne frequency splitting. Moreover, nonlinearity in the output and frequency response of detector 40 and the electronics therein introduces additional terms and mixes the dominant term a cos($\omega$t+$\phi$+$\zeta$) with the terms described above. For example, an expression for s(t) that accounts for some of the nonlinearities can take the form:

$$s(t) = \sum_q B_q \left\{ \sum_{u,p} a_{up} \cos(u\omega t + p\varphi + \zeta_{up}) \right\}^q$$

where p=1,2,3 . . . and fractional values, u=0 or 1, and q=1,2,3 . . . , and where the "q" index is associated with nonlinearity in detector 40. The above equation for s(t), however, assumes that the nonlinearity in the detector is frequency independent. If it is not, each of the terms that result from the expansion in the above equation can include a phase-shift and amplitude that depend on the frequency of that term. The expression can be further complicated by the finite sampling rate of the analog-to-digital converter in detector 40, which can cause aliasing in the digital representation of s(t).

If not accounted for, the contributions of the nonlinearities to s(t) can degrade the accuracy of the optical path difference information to be extracted from the interference signal. Often, the degree to which the accuracy is degraded depends on $\dot\phi$, or the relative speed of the measurement and reference objects, e.g., the Doppler shift. For example, at large Doppler shifts, determining a change in $\phi$ from the phase of the Fourier transform of s(t) at $\omega$+$\dot\phi$ minimizes the contributions from those nonlinearities that have peaks separated in frequency space from $\omega$+$\dot\phi$, e.g., at 2$\dot\phi$, $\omega$+2$\dot\phi$, $\omega$+3$\dot\phi$, 2$\omega$+2$\dot\phi$. However, at smaller Doppler shifts, the contributions from many nonlinearities will overlap with the dominant peak at $\omega$+$\dot\phi$ in the power spectrum of s(t), the power spectrum being the square modulus of the Fourier transform of s(t). The overlap is particularly large when $\dot\phi$=0, e.g., when the relative position of the measurement and reference object is stationary, or when the relative speed of the measurement and reference objects changes sign. Moreover, even when the Doppler shift separates the frequency of the nonlinearity from that of the dominant peak in the power spectrum of s(t), aliases of the frequency of the nonlinearities may overlap with the dominant peak at $\omega$+$\dot\phi$. Furthermore, the magnitude and phase of the nonlinearity, e.g., $B_q a_{up}$ and $\zeta_{up}$, may also vary with $\dot\phi$ because, for example, of a frequency-dependent response of the detection electronics.

Furthermore, some of the nonlinearities have frequencies that overlap exactly with the dominant peak, regardless of the value of $\dot\phi$. Such nonlinearities can be called zero-frequency-shift cyclic errors. For example, in the expansion of s(t) in the equation above for q=3, the $B_3 a_{11}^3 \cos^3(\omega t + \phi + \zeta_{11})$ produces a term at the dominant frequency. Similarly, for example, difference mixing in the q=2 expansion between a u=1,p=2 term and a u=0,p=1 term produces a term at the dominant frequency.

Analyzer 50 quantifies the nonlinearities based on values of s(t) for multiple optical path length differences. In some embodiments, the nonlinearities are expressed as additional sinusoidal terms in an expression for s(t) as shown, for example, in the above equation. In other embodiments, the nonlinearities are expressed in an additional phase term $\psi$ in s(t), where s(t)=A(t)cos($\omega$t+$\phi$+$\psi$+$\zeta$) and the phase term $\psi$ can be expressed as a series of sinusoids having arguments similar to those shown in the sinusoids of the above equation for s(t). In either case, each nonlinearity is quantified by estimating the amplitude and phase of its corresponding sinusoid, the amplitude and phase defining coefficients for the nonlinearity. Alternatively, coefficients can be defined by the amplitudes of sine and cosine terms that both have the argument corresponding to the nonlinearity.

During operation, analyzer 50 determines $\phi$ (relative to the offset phase $\zeta_{11}$) from the interference signal s(t) and the quantified nonlinearities or an initial guess for the quantified nonlinearities by using an iterative process, e.g., by first determining $\phi$ assuming no nonlinearities, and then determining iteratively improved values for $\phi$ from the interference signal by including the contributions of nonlinearities that correspond to the previously determined value of $\phi$. Analyzer can also determine values for $\dot\phi$ based on the interference signal s(t) and the quantified nonlinearities or an initial guess for the quantified nonlinearities.

In embodiments where the nonlinearities are expressed as a series of sinusoids in an expression s(t), analyzer 50 estimates the coefficients of the nonlinearities by Fourier transforming values of s(t) corresponding to a substantially constant value of $\dot\phi$ that causes the frequency peaks of one or more of the nonlinearities to be separated spectrally from the dominant frequency $\omega$+$\dot\phi$, thereby allowing the nonlinearities to be quantified. The analyzer identifies the dominant peak at $\omega$+$\dot\phi$, associates each of the remaining peaks with a nonlinearity, and determines the coefficients for each nonlinearity from the complex amplitude of its corresponding peak and, where necessary, a normalization factor that accounts for the effect of higher order derivatives of $\phi$ on the Fourier transform. Analyzer 50 can repeat these steps for additional sets of values of s(t) corresponding to the same substantially constant value of $\dot\phi$, and average (or "filter") the determined coefficients from all of the sets to improve the quantification of the nonlinearities.

Analyzer 50 then repeats the steps in the preceding paragraph for values of s(t) corresponding to a different substantially constant value of $\dot\phi$. The Fourier transform of such values can produce peaks for nonlinearities that were not resolved in the Fourier transform of the values of s(t) corresponding to the first substantially constant value of $\dot\phi$, and permits the analyzer to determine the coefficients for the previously unresolved nonlinearities. The steps can be further repeated for values of s(t) corresponding to each of additional, substantially constant values of $\dot\phi$. Furthermore, analyzer 50 can interpolate the values of the coefficients determined for values of s(t) corresponding to each of the different, substantially constant values of $\dot\phi$, to determine the dependence of each nonlinearity on $\dot\phi$, if any.

In other embodiments in which the nonlinearities are expressed as a series of sinusoids in the phase $\psi$ of $s(t)=A(t)\cos(\omega t+\phi+\psi+\zeta)$, analyzer 50 estimates the coefficients of the nonlinearities by Fourier transforming the phase $\alpha$ (where $\alpha=\omega t+\phi+\psi+\zeta$) of values of s(t) corresponding to each of multiple, substantially constant values of $\phi$. Otherwise the analysis is similar to that described above. In further embodiments, any combination of $\omega t$, $\phi$, and $\psi$, can be subtracted from $\alpha$ before taking the Fourier transforms, where $\bar\phi$ and $\bar\psi$ are approximate guesses for $\phi$ and $\psi$, respectively.

In dispersion applications or applications in which the intrinsic refractive properties of a gas are being measured, detector 40 sends signals $s_\lambda(t)$ for each of multiple wavelengths $\lambda$ to analyzer 50. Quantification of the nonlinearities by analyzer 50 can be based on one or more of the signals $s_\lambda(t)$ in a manner similar to that summarized above. Furthermore, because of the improved accuracy provided by the quantification of nonlinearities, interferometry system 10 can be advantageously used in microlithography and beam-writing systems.

The magnitudes of the nonlinearities can change over time as components of the interferometry system degrade. For example, optical and electronic components can degrade over time because of, e.g., overuse, faulty design, or environmental factors such as humidity, dust, and temperature. Furthermore, environmental disturbances may degrade the optical alignment of the system.

Referring again to FIG. 1, to identify such degradation, analyzer 50 monitors the quantified nonlinearities over time to determine whether there is any sudden or gradual increase in the magnitude of one or more of the quantified nonlinearities. For example, analyzer can monitor the frequency spectrum of either s(t) or the phase $\alpha$ of s(t), and determine when peaks at frequencies other than the dominant frequency $\omega+\phi$ exceed an acceptable threshold level. If so, analyzer 50 sends a signal 55 indicative of system degradation to an alert mechanism 60. The alert mechanism responds to signal 55 indicative of system degradation by alerting a user that one or more components of the interferometry system may have degraded beyond an acceptable level. For example, alert mechanism 60 can include one or more of a video monitor that displays an error message in response to signal 55, a sound system or siren that produces an audio warning signal in response to signal 55, a printer that prints an error message in response to signal 55, and a light that flashes or changes color in response to signal 55. Alert mechanism 60 can also be coupled to a related system, e.g., a lithography or a beam writing system, and can cause the related system to shut down in response to signal 55.

The threshold level in analyzer 50 can be preset by an operator to define the acceptable level for a particular application. Moreover, an operator may preset multiple threshold levels, each corresponding to a particular nonlinearity, e.g., the corresponding frequency of the nonlinearity in the frequency spectrum of s(t) or the phase $\alpha$ of s(t). Furthermore, even for a particular nonlinearity, the analyzer 50 can compare the magnitude of the nonlinearity to multiple threshold levels and cause signal 55 to indicate a degree of degradation corresponding to which threshold levels had been exceeded. Depending on the embodiment, analyzer 50 can quantify the nonlinearities and correct the measurement of the optical path length difference using the quantified nonlinearities, monitor system degradation based on the magnitude of nonlinearities in the frequency spectrum of s(t) (or the phase $\alpha$ of s(t)), or both.

Detailed descriptions of specific embodiments follow below. While they differ in some details, the disclosed embodiments otherwise share many common elements and naturally fall into several different categories depending on the type of end use application and on the type of procedure used for measuring and correcting for effects of nonlinearities due to the cyclic errors.

A first category of embodiments of the several different categories comprise distance measuring interferometers operating with one wavelength and effects of cyclic errors are determined and compensated. The effects of cyclic errors are determined from analyses of Fourier transforms of electrical interference signals wherein the electrical interference signals are generated by detection of a polarization mixed reference and measurement beams from the interferometers.

A second category of embodiments of the several different categories comprise distance measuring interferometers operating with one wavelength and the effects of cyclic errors are compensated using measured effects of cyclic error determined in part from analyses of Fourier transforms of phases of electrical interference signals. The electrical interference signals are generated by detection of polarization mixed reference and measurement beams from the interferometers.

Embodiments of a third category of the several different categories comprise an apparatus and method for compensating for effects of cyclic errors on dispersion or dispersion and distance measuring related signals. The effects of the cyclic errors are determined from analyses of Fourier transforms of electrical interference signals wherein the electrical interference signals are generated by detection of polarization mixed reference and measurement beams from dispersion measuring and distance measuring interferometers. The effects of a gas in the measuring path of a distance measuring interferometer are corrected by a dispersion interferometry based procedure.

A fourth category of embodiments of the several different categories comprise both an apparatus and method for measuring and compensating for effects of cyclic errors in dispersion related signals and in both dispersion related signals and distance measuring related signals of distance measuring interferometry. Dispersion interferometry is used to determine the effects of a gas on the measured optical path of the distance measuring interferometry and an apparatus and method is used for detecting and compensating for the effects of cyclic errors in the dispersion related signals and in the distance measuring related signals. Effects of cyclic errors are compensated in the dispersion measuring related signals or the dispersion measuring and the distance measuring related signals using measured effects of cyclic error. The measured effects of cyclic error are determined from analyses of Fourier transforms of phases of electrical interference signals wherein the electrical interference signals are generated by detection of polarization mixed reference and measurement beams from the distance measuring and/or dispersion measuring interferometers.

Embodiments in a fifth category of the several different categories comprise both an apparatus and method for measuring and correcting for cyclic errors in both a dispersion measuring related signal and a refractivity measuring related signal or refractivity measuring related signals used to determine intrinsic optical properties of a gas. Embodiments in the fifth category of the several different categories also comprise both an apparatus and method for measuring and correcting for cyclic errors in a wavelength measuring and/or related signal used to determine and/or monitor the wavelength of an optical beam.

Figure 2A:
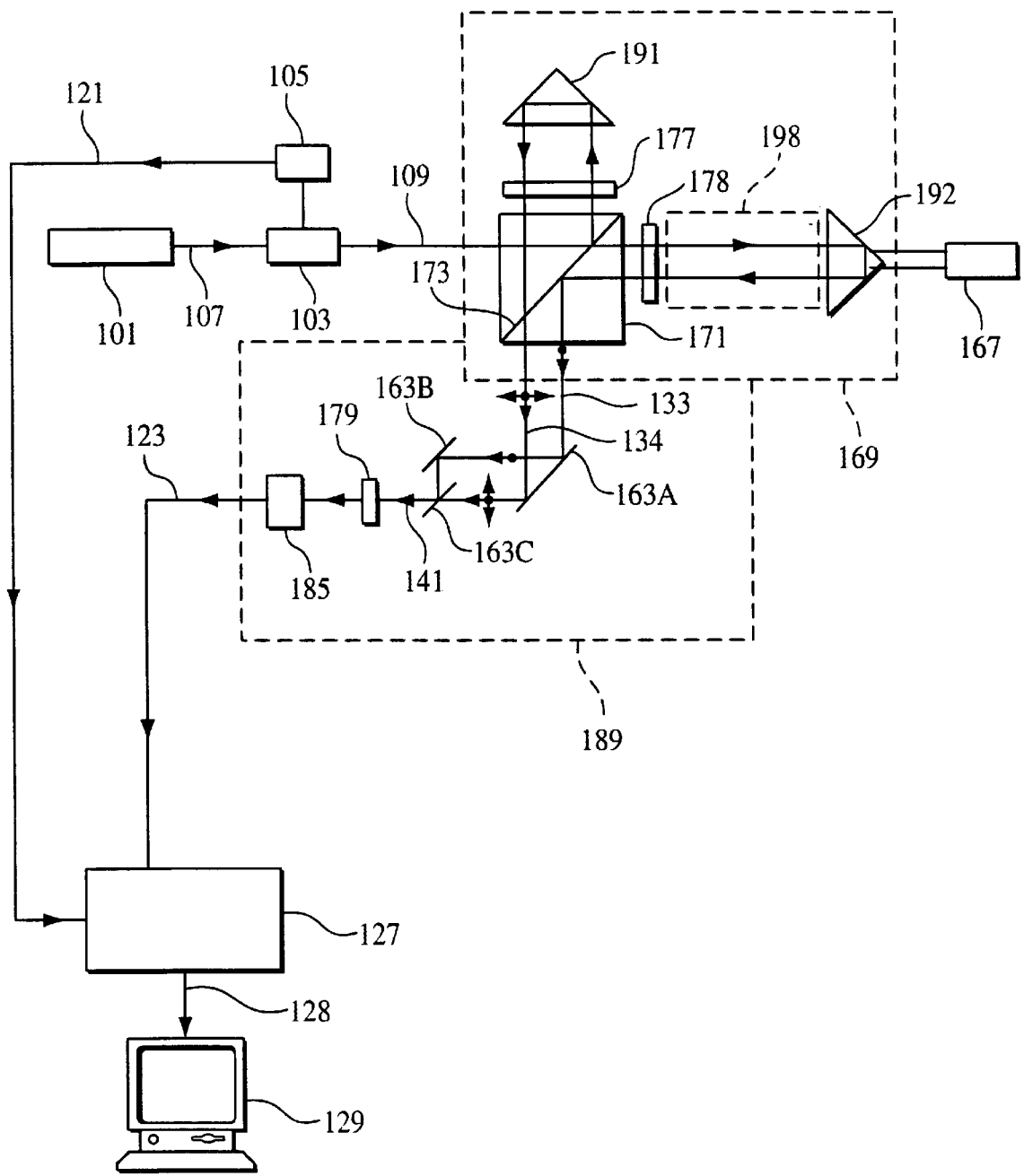
FIG. 2a is a schematic diagrams of a first embodiment of an interferometry system that quantifies nonlinearities.

FIG. 2a depicts in schematic form an apparatus and method in accordance with the first embodiment of the present invention. The first embodiment is from the first category of embodiments. The interferometer depicted in FIG. 2a is a polarizing, heterodyne, single pass interferometer. Although the first embodiment comprises a heterodyne system, the instant invention is readily adapted for use in a homodyne system in which the reference and measurement beams have the same frequencies before introduction of any Doppler shifts. While the apparatus has application for a wide range of radiation sources, the following description is taken by way of example with respect to an optical measuring system.

Referring to FIG. 2a, a light beam 107 emitted from source 101 passes through a modulator 103 becoming light beam 109. Modulator 103 is excited by a driver 105. Source 101 is preferably a laser or like source of coherent radiation, preferably polarized, and having a wavelength $\lambda_2$. Modulator 103 may, for example, be an acousto-optic device or a combination of acousto-optic devices with additional optics for selectively modulating polarization components of beam 107. Modulator 103 preferably shifts the oscillation frequency of one linearly polarized component of beam 107 an amount $f_2$ with respect to an orthogonally linearly polarized component, the directions of polarizations of the non-frequency and frequency shifted components being parallel and orthogonal, respectively, to the plane of FIG. 2a. The oscillation frequency $f_2$ is determined by the driver 105.

Light source 101 such as a laser can be any of a variety of frequency modulation apparatus and/or lasers. For example, the laser can be a gas laser, e.g., a HeNe laser, stabilized in any of a variety of conventional techniques known to those skilled in the art, see for example, T. Baer et al., "Frequency Stabilization of a 0.633 $\mu$m He—Ne-longitudinal Zeeman Laser," *Applied Optics*, 19, 3173–3177 (1980); Burgwald et al., U.S. Pat. No. 3,889,207, issued Jun. 10, 1975; and Sandstrom et al., U.S. Pat. No. 3,662,279, issued May 9, 1972. Alternatively, the laser can be a diode laser frequency stabilized in one of a variety of conventional techniques known to those skilled in the art, see for example, T. Okoshi and K. Kikuchi, "Frequency Stabilization of Semiconductor Lasers for Heterodyne-type Optical Communication Systems," *Electronic Letters*, 16, 179–181 (1980) and S. Yamaqguchi and M. Suzuki, "Simultaneous Stabilization of the Frequency and Power of an AlGaAs Semiconductor Laser by Use of the Optogalvanic Effect of Krypton," *IEEE J. Quantum Electronics*, QE-19, 1514–1519 (1983).

Two optical frequencies may be produced by one of the following techniques: (1) use of a Zeeman split laser, see for example, Bagley et al., U.S. Pat. No. 3,458,259, issued Jul. 29, 1969; G. Bouwhuis, "Interferometrie Mit Gaslasers," Ned. T. Natuurk, 34, 225–232 (August 1968); Bagley et al., U.S. Pat. No. 3,656,853, issued Apr. 18, 1972; and H. Matsumoto, "Recent interferometric measurements using stabilized lasers," *Precision Engineering*, 6(2), 87–94 (1984); (2) use of a pair of acousto-optical Bragg cells, see for example, Y. Ohtsuka and K. Itoh, "Two-frequency Laser Interferometer for Small Displacement Measurements in a Low Frequency Range," *Applied Optics*, 18(2), 219–224 (1979); N. Massie et al., "Measuring Laser Flow Fields With a 64-Channel Heterodyne Interferometer," *Applied Optics*, 22(14), 2141–2151 (1983); Y. Ohtsuka and M. Tsubokawa, "Dynamic Two-frequency Interferometry for Small Displacement Measurements," *Optics and Laser Technology*, 16, 25–29 (1984); H. Matsumoto, ibid.; P. Dirksen, et al., U.S. Pat. No. 5,485,272, issued Jan. 16, 1996; N. A. Riza and M. M. K. Howlader, "Acousto-optic system for the generation and control of tunable low-frequency signals," *Opt. Eng.*, 35(4), 920–925 (1996); (3) use of a single acousto-optic Bragg cell, see for example, G. E. Sommargren, commonly owned U.S. Pat. No. 4,684,828, issued Aug. 4, 1987; G. E. Sommargren, commonly owned U.S. Pat. No. 4,687,958, issued Aug. 18, 1987; P. Dirksen, et al., ibid.; (4) use of two longitudinal modes of a randomly polarized HeNe laser, see for example, J. B. Ferguson and R. H. Morris, "Single Mode Collapse in 6328 Å HeNe Lasers," *Applied Optics*, 17(18), 2924–2929 (1978); (5) use of birefringent elements or the like internal to the laser, see for example, V. Evtuhov and A. E. Siegman, "A "Twisted-Mode" Technique for Obtaining Axially Uniform Energy Density in a Laser Cavity," *Applied Optics*, 4(1), 142–143 (1965); or the use of the systems described in U.S. patent application with Ser. No. 09/061,928 filed Apr. 17, 1998 entitled "Apparatus to Transform Two Non-Parallel Propagating Optical Beam Components into Two Orthogonally Polarized Beam Components" and U.S. patent application with Ser. No. 09/507,529 filed Feb. 18, 2000 entitled "Apparatus for Generating Linearly-Orthogonally Polarized Light Beams" both by Henry A. Hill, the contents of both applications which are incorporated herein by reference.

The specific device used for the source of beam 109 will determine the diameter and divergence of beam 109. For some sources, e.g., a diode laser, it will likely be necessary to use conventional beam shaping optics, e.g., a conventional microscope objective, to provide beam 109 with a suitable diameter and divergence for elements that follow. When the source is a HeNe laser, for example, beam shaping optics may not be required.

As shown in FIG. 2a, interferometer 169 comprises a reference retroreflector 191, object retroreflector 192, quarter wave phase retardation plates 177 and 178, and a polarizing beam splitter 171. This configuration is known in the art as a polarized Michelson interferometer. The position of object retroreflector 192 is controlled by translator 167.

Beam 109 incident on interferometer 169 results in beams 133 and 134 as illustrated in FIG. 2a. Beams 133 and 134 contain information at wavelength $\lambda_2$ about the optical path length through the measuring path 198 and about the optical path length through the reference path, respectively. Beams 133 and 134 exit interferometer 169 and enter detector system 189 illustrated in diagrammatic form in FIG. 2a. In detector system 189, beam 133 is reflected by mirror 163A, reflected by mirror 163B, incident on polarizing beam splitter 163C, and a portion thereof reflected by polarizing beam splitter 163C to become a first component of beam 141. Beam 134 is reflected by mirror 163A, incident of polarizing beam splitter 163C, and a portion thereof transmitted by polarizing beam splitter 163C to become a second component of beam 141.

Interferometer 169 introduces phase shift $\phi_2$ between the first and second components of beam 141 so that beam 141 is a phase-shifted beam. The magnitude of phase shift $\phi_2$ is related to round-trip physical length $L_2$ of measurement path 198 according to the formulae $$\phi_2 = L_2 p_2 k_2 n_2 \qquad (1)$$

where $p_2$ is the number of passes through the respective reference and measurement legs, $n_2$ is the refractive index of a gas in measurement path 198 corresponding to the optical path introducing the phase shift $\phi_2$ and to wavenumber $k_2 = 2\pi/\lambda_2$. The interferometer shown in FIG. 2a is for $p_2=1$ so as to illustrate in the simplest manner the function of the apparatus of the first embodiment. To those skilled in the art, the generalization to the case when $p_2 \neq 1$ is a straight forward procedure. The value for $L_2$ corresponds to twice the difference between the physical length of measurement path 198 and an associated reference path.

In a next step as shown in FIG. 2a, phase-shifted beam 141 passes through polarizer 179, impinges upon photodetector 185, and generates an electrical interference signal, heterodyne signal $s_2$, preferably by photoelectric detection. Polarizer 179 is oriented so as to mix polarization components of phase-shifted beam 141. Signal $s_2$ may be written in a spectral representation of the form $$s_2 = a_{2,1,0,1,0}\cos(\omega_2 t + \varphi_2 + \zeta_{2,1,0,1,0}) +$$

$$\sum_{u,u',p,p^+} a_{2,u,u',p,p^+}\cos(u\omega_2 t + \omega'_{2u'} + p\varphi_2 - p^+\varphi_2^+ +$$

$$+\zeta_{2,u,u',p,p^+}) +$$

$$\sum_q (a_{2,1,0,1,0})^q \begin{cases} B_{2,1,0,1,0,q,q}\cos[q(\omega_2 t + \varphi_2) + \zeta_{2,1,0,1,0,q,q}] + \\ B_{2,1,0,1,0,q,q-2}\cos[(q-2)(\omega_2 t + \varphi_2) + \zeta_{2,1,0,1,0,q,q-2}] + \\ \ldots + \\ B_{2,1,0,1,0,q,q_R}\cos[q_R(\omega_2 t + \varphi_2) + \zeta_{2,1,0,1,0,q,q_R}] \end{cases} +$$

$$\ldots,$$

$u=0,1;$ $u'=0,1,\ldots;$ except $u'\neq 0$ if $u=1$, $p=1$, $p^+=0$; $\omega'_{2,0}=0;$ $p,p^+=0,1,\ldots;$ $w_{2,1}/w_{2,2};$ $p^+\neq 0$ if $p=1$ and $u=1;$ $w_{2,1},w_{2,2}=1,2,\ldots;$ $w_{2,1}\neq w_{2,2};$ \hfill (2)

$q=2,3,\ldots;$ where $\phi_2^+=L_2 p_2 k_2^+ n_2;$ \hfill (3)

$k_2^+=2\pi[(1/\lambda_2)+(f_2/c)];$ \hfill (4)

$\omega'_{2u'}$ is a set of angular frequencies not including $\omega$; $q_R=1$ or 0 depending on whether q is an odd or even integer, respectively; and c is the speed of light in vacuum.

Terms in Eq. (2) with $p^+\geq 1$ arise as a result of a portion of the reference beam component of the beam 109 being transmitted through polarizing beam splitter 171 and passing through the measurement beam path 198. The terms with $u=0$ may arise as a result of a portion of the measurement beam component of beam 109 being reflected by polarizing beam splitter 171, passing through the reference path of interferometer 169, and being detected as an electrical interference signal generated by detection of the portion of the measurement beam component and the measurement beam component that passes through the measurement path 198. The terms with $u=0$ may also arise as a result of a portion of the reference beam component of beam 109 being transmitted by polarizing beam splitter 171, passing through the measurement beam path 198, and detected as an electrical interference signal generated by detection of the portion of the reference beam component of the beam 109 and the reference beam component that passes through the reference path of interferometer 169. The terms with $u'\neq 0$ may arise from intensity fluctuations in beam 107 that as can be produced by one or more switching frequencies in power supplies of source 101.

The parameter q is a nonlinearity order index where the nonlinearity arises as a result of nonlinearities in detector 185 and/or the analogue-to-digital converter used to convert $s_2$ from an analogue signal to a digital format. Coefficients $B_{2,u,u',p,p^+,q,m}$ are related to the coefficients in the expansion of $(\cos x)^q$ in terms of $\cos(q-m)x$, $m=q,q-2,\ldots,q_R$. The coefficients $a_{2,u,u',p^+}$, phase offsets $\zeta_{2,u,u',p,p^+}$, and coefficients $B_{2,u,u',p,p^+,q,m}$ may be functions of system properties such as degree of overlap of reference and measurement beam components of an output beam, the angular frequency $\phi_2$, and the intensity of beam 109 but are otherwise substantially constant in time.

There are terms not explicitly represented in Eq. (2) that are due to higher order effects, a higher order than those explicitly represented in Eq. (2). Effects of the higher order effect terms are typically less than effects of the terms explicitly represented in Eq. (2). However, should it be necessary to include for a given application any of the higher order effect terms not explicitly represented in from Eq. (2), such terms will be identified in an initialization procedure and operating procedure of the first embodiment and thereby included in described cyclic error compensation procedure of the first embodiment.

The dominant term in Eq. (2) has a phase dependence of $(\omega_2 t+\phi_2+\zeta_{2,1,0,1,0})$ and coefficient $a_{2,1,0,1,0}$. The remaining terms in Eq. (2), hereinafter denoted as $s_{2,\psi}$, i.e.

$$s_{2,\psi}=s_2-a_{2,1,0,1,0}\cos(\omega_2 t+\phi_2+\zeta_{2,1,0,1,0}), \hfill (5)$$

correspond to cyclic error terms.

Heterodyne signal $s_2$ is transmitted to electronic processor 127 for analysis as electronic signal 123 in either digital or analog format, preferably in digital format. Electronic signal 123 further comprises a Nyquist angular frequency $\omega_{2,Ny}$ determined by the sampling frequency of an analog-to-digital converter, preferably in detector 185, used in the conversion of $s_2$ to a digital format.

The phase of driver 105 is transmitted by electrical signal $S_{2,Ref}$, reference signal 121, in either digital or analog format, preferably in digital format, to electronic processor 127. A reference signal, an alternative reference signal to reference signal 121, may also be generated by an optical pick off means and detector (not shown in figures) by splitting off a portion of beam 109 with a non-polarizing beam splitter, mixing the portion of the beam 109 that is split off, and detecting the mixed portion to produce an alternative heterodyne reference signal.

Figure 2B:
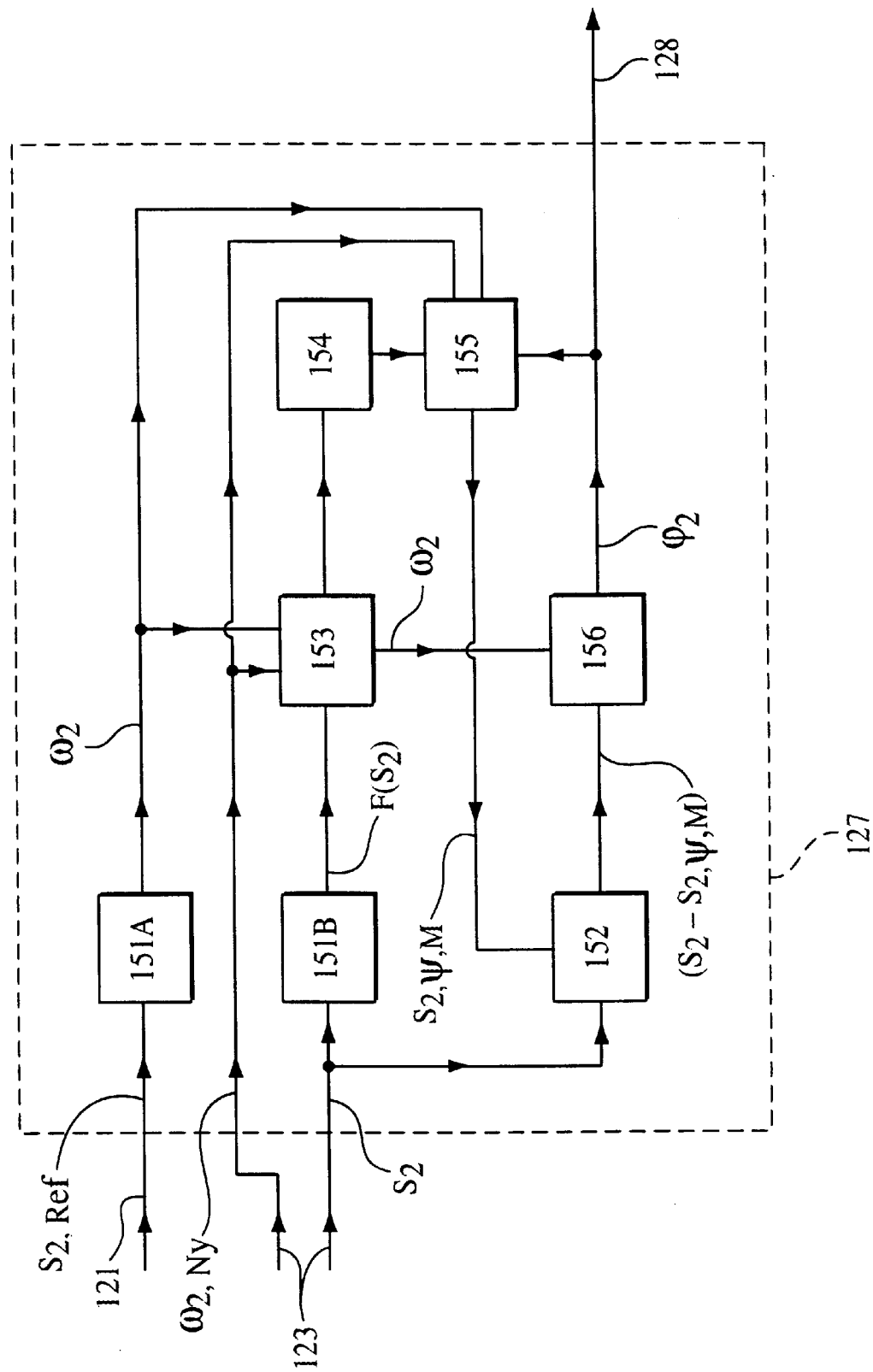

Referring to FIG. 2b, electronic processor 127 comprises electronic processor 151B where a Fourier transform $F(s_2)$ of heterodyne signal $s_2$ is generated by either digital or analog signal processes, preferably a digital process such as a finite Fourier transform algorithm (FFT). Electronic processor 127 further comprises spectrum analyzer 151A that processes reference signal $s_{2,Ref}$ for $\omega_2=2\pi f_2$. Spectrum analyzer 151A is preferably based on a sliding window Fourier transform algorithm.

In a next step, Fourier transform $F(s_2)$ and angular frequencies $\omega_2$ and $\omega_{2,Ny}$ are transmitted to electronic processor 153 where complex spectral coefficients in $F(s_2)$ corresponding to cyclic error terms in $s_{2,\psi}$ are extracted at angular frequencies $\omega_{2,v}$ and aliases of $\omega_{2,v}$. An amplitude of a cyclic error term in $s_{2,\psi}$ corresponds to the amplitude of a corresponding peak in an associated power spectrum and the phase of the cyclic error term in $s_{2,\psi}$ corresponds to the arctan of the ratio of the imaginary and real components of $F(s_2)$ at the angular frequency of the corresponding peak in the associated power spectrum. Angular frequencies $\omega_{2,v}$, where $v$ is an index parameter comprising u, u', p, $p^+$, and q, correspond to the set of angular frequencies equal to derivatives, with respect to time, of the arguments of the sinusoidal factors in the terms of $s_{2,\psi}$. Aliases $\omega_{2,v,A}$ of $\omega_{2,v}$ are given by the formula $$\tilde{\omega}_{2,v,A} = (-1)^r \tilde{\omega}_{2,v} - \left[(-1)^r\left(r+\frac{1}{2}\right)-\left(\frac{1}{2}\right)\right]\omega_{2,Ny}; \quad (6)$$
$$r = 1, 2, \ldots;$$

with $$r\omega_{2,Ny} < \omega_{2,v} < (r+1)\omega_{2,Ny}. \quad (7)$$

In practice, the amplitudes and associated phases of cyclic error terms in $s_{2,\psi}$ need be extracted only for a small subset of the set of possible $\omega_{2,v}$ and $\omega_{2,v,A}$. The selection of the subset of the set of possible $\omega_{2,v}$ and $\omega_{2,v,A}$ may be guided by properties of certain terms in Eq. (2). However, as part of an initialization procedure, the selection of the subset of the set of possible $\omega_{2,v}$ and $\omega_{2,v,A}$ is based on a power spectrum analysis of $s_2$ and chi-square tests of peaks in the power spectrum. The chi-square tests identify statistically significant peaks in the power spectrum. Representation of the angular frequencies $\omega_{2,v}$ and $\omega_{2,v,A}$ of the subset of $\omega_{2,v}$ and $\omega_{2,v,A}$ associated with the statistically significant peaks in terms of $\omega_2$, $\omega_{2,Ny}$, $\dot{\phi}_2$, $\dot{\phi}_2^+$, u, u', p, $p^+$, q, $w_{2,1}/w_{2,2}$, and r is determined by observing properties of the respective $\omega_{2,v}$ and $\omega_{2,v,A}$ as $\dot{\phi}_2$ is varied where $\dot{\phi}_2 = d\phi_2/dt$ and $\dot{\phi}_2^+ = d\phi_2^+/dt$. Note that $\dot{\phi}_2^+ = \dot{\phi}_2$ to a relative precision of the order of or less than $10^{-6}$.

The initialization procedure is performed by electronic processor 153. As part of an operating procedure of the first embodiment, power spectrum analyses of $s_2$ and chi-square tests of peaks in the power spectra are monitored for possible changes that may need be made to the subset of the set of possible $\omega_{2,v}$ and $\omega_{2,v,A}$ during operation of the apparatus and method of the first embodiment. The power spectrum analyses of $s_2$ and associated chi-square tests executed as part of the monitoring procedure are also performed as a background task by electronic processor 153.

Cyclic error terms in $s_{2,\psi}$ comprise terms generated by several mechanisms and hereinafter will be referred to broadly as comprising coherent cyclic errors. For some configurations of interferometers, in particular multiple pass interferometers, it is possible for a system comprising a source, interferometer, and detector to generate coherent cyclic errors that comprise subharmonics of $\dot{\phi}_2$. Cyclic errors terms in $s_{2,\psi}$ comprising subharmonics of $\dot{\phi}_2$ correspond to terms in Eq. (2) with $p = w_{2,1}/w_{2,2}$, $w_{2,1}, w_{2,2}=1,2,\ldots$, $w_{2,1} \neq w_{2,2}$ and/or $p^+ = w_{2,1}/w_{2,2}$, $w_{2,1}, w_{2,2}=1,2,\ldots$, $w_{2,1} \neq w_{2,2}$.

One example of subharmonic cyclic error generation can be in a differential plane mirror interferometer where a ghost beam is generated as a result of one reflection by an object mirror, and a second reflection from a nominally transmissive surface of a quarter wave phase retardation plate. When the reflecting surface of the object mirror and the nominally transmissive surface of the quarter wave phase retardation plate are parallel, the ghost beam and reference beam components of output beam have directions of propagation that are parallel. A subsequent detection of a mixed output beam comprising ghost and reference beam components is a heterodyne signal with a subharmonic cyclic error.

Another example of subharmonic cyclic error generation can be in a high stability plane mirror interferometer, HSPMI, comprising a polarizing beam splitter, a measurement object and reference plane mirrors, and a retroreflector. The state of polarizations of an input beam impinging on a retroreflector and a corresponding exit beam are generally different, e.g., for a linearly polarized input beam, the exit beam typically is elliptically polarized with the major axis of the ellipse rotated with respect to the plane of polarization of the input beam (see N. Bobroff, "Recent advances in displacement measuring interferometry," *Measurement and Sci. & Tech.*, 4(9), 907–926, 1993). The ellipticity of the exit beam generates measurement and reference beam components in the HSPMI output beam that have made only a single pass instead a double pass to the measurement object mirror. The single pass components when mixed with other components of the HSPMI output beam produce subharmonic cyclic errors in subsequently generated interference signal.

In addition, it is possible for a system comprising a source, interferometer, detector, and digital signal processing to generate coherent cyclic errors that comprise neither subharmonics or harmonics of $\dot{\phi}_2$ but are related to harmonics of $\omega_2 + \dot{\phi}_2$, $\omega_2$, and other angular frequencies. Coherent cyclic errors that have angular frequencies that are not subharmonics, not harmonics of subharmonics, and not harmonics of $\dot{\phi}_2$ can be produced for example by nonlinearities in the detector and/or amplifiers generating $s_2$ and in an analog-to-digital converter used to digitize $s_2$ and have angular frequencies which are harmonics of $\omega_2 + \dot{\phi}_2$, $\omega_2$, and other angular frequencies. Coherent cyclic errors that have angular frequencies that are not subharmonics, not harmonics of subharmonics, and not harmonics of $\dot{\phi}_2$ can also be produced for example by aliasing in digital signal processing and have angular frequencies which are aliases of subharmonics and harmonics of $\dot{\phi}_2$ and aliases of $\omega_2 + \dot{\phi}_2$, $\omega_2$, and other angular frequencies and harmonics thereof. The aliases are related to the Nyquist angular frequency $\omega_{2,Ny}$.

Figure 2C:
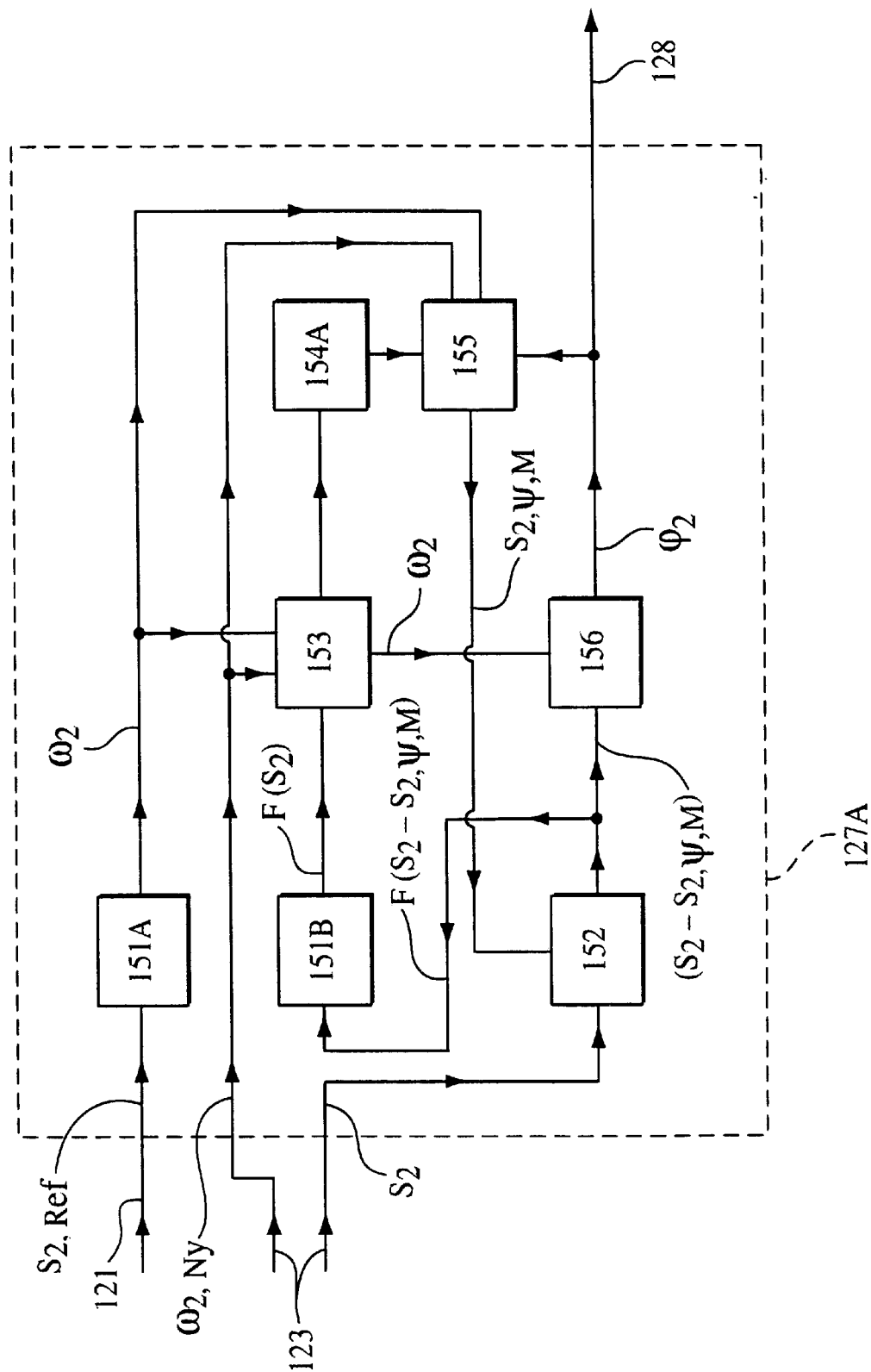
Figure 2D:
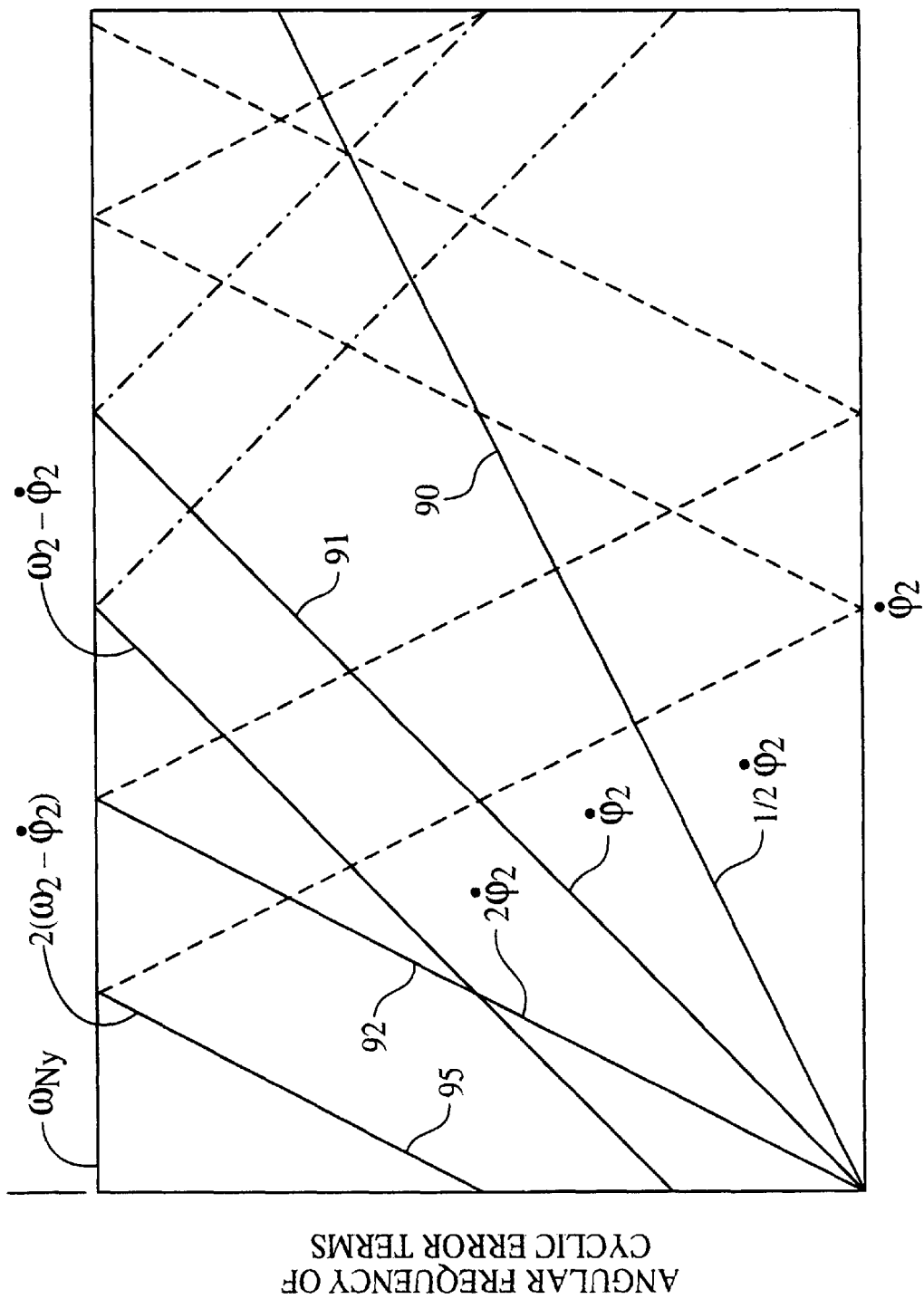
FIG. 2d is a graph that illustrates the frequencies of various types of nonlinearities.

An example of the various coherent cyclic errors that are harmonics of $\dot{\phi}_2$ and coherent cyclic errors that have angular frequencies that are not subharmonics and not harmonics of $\dot{\phi}_2$ is shown graphically in FIG. 2d as a function of $\dot{\phi}_2$. Coherent cyclic errors that are harmonics and subharmonics of $\dot{\phi}_2$ are indicated in FIG. 2d as solid lines 90, 91, and 92, for example, with line 91 being the first harmonic. Coherent cyclic errors that are the result for example of nonlinearities in the detector and amplifiers generating $s_2$ and in analog-to-digital converters are indicated in FIG. 2d as solid line 95. Coherent cyclic errors that are the result of aliasing are indicated in FIG. 2d as dashed lines that reflect from line 99 representing the Nyquist frequency.

The amplitudes and phase offsets of terms in the spectral representation given by Eq. (2) will in general depend on the magnitude of the rate of change of a phase associated with the term as a result, for example, of properties of group delay experienced by the heterodyne signal. Group delay, often called envelope delay, describes the delay of a packet of frequencies and the group delay at a particular frequency is defined as the negative of the slope of the phase curve at the particular frequency [see H. J. Blinchikoff and A. I. Zverev, *Filtering in the Time and Frequency Domains*, Section 2.6, 1976 (Wiley, New York)].

The extracted complex spectral coefficients in $F(s_2)$ corresponding to cyclic error terms in $s_{2,\psi}$ are then sent to electronic processor 154 where the extracted spectral coefficients are normalized, filtered with respect to time, and interpolations made as required and a multidimensional array of normalized, filtered, and interpolated complex spectral coefficients maintained. The step of normalization is for the purpose of compensating for effects of non-zero values of second and higher order derivatives of $\phi_2$ with respect to time that exist at the time of a determination of the set of complex spectral coefficients. The dimensionality of the multidimensional array is determined in part by the magnitude of the filtered complex spectral coefficients, the required precision of an end use application with respect to correction for coherent cyclic errors, and the dependence of the filtered complex spectral coefficients on $\dot{\phi}_2$ and other system properties.

For the next step in electronic processor 127 as shown in FIG. 2b, electronic procession 155 computes the coherent cyclic error correction $s_{2,\psi,M}$ using information listed in the multidimensional array of normalized, filtered, and interpolated complex spectral coefficients and generated by electronic processor 154. Electronic processor 152 computes $s_2-s_{2,\psi,M}$ to compensate for coherent cyclic errors in $s_2$. Coherent cyclic error compensated signal $s_2-s_{2,\psi,M}$ and angular frequency $\omega_2$ are transmitted to electronic processor 256 where the phase of $s_2-s_{2,\psi,M}$, $\phi_2$, is determined by a phase detector such as a sliding window FFT, a zero crossing phase detector, or the like. Phase $\phi_2$ is transmitted as signal 128 to digital computer 129 for use in downstream applications such as determining linear displacements of object 192 not effected by coherent cyclic errors.

Each of the electronic processors comprising electronic processor 127 preferably performs respective functions as digital processes.

The formalism for the normalization of extracted complex spectral coefficients is next described. The Fourier transform of $s_2$ comprises Fourier transforms of terms having factors such as $$\cos\zeta_{2,u,u',p,p^+}\cos(u\omega_2 t+\omega'_u+p\phi_2-p^+\phi_2^+)$$

and $$\sin\zeta_{2,u,u',p,p^+}\sin(u\omega_2 t+\omega'_u+p\phi_2-p^+\phi_2^+)$$

as evident from Eq. (2).

The Fourier transform of a sinusoidal function $\sin\beta$ is related to the Fourier transform of $\cos\beta$ as $$F(\sin\beta)=F\{\cos[\beta-(\pi/2)]\} \qquad (8)$$

where $\beta$ is a function of time and representative of arguments of sinusoidal factors in Eq. (2). For evaluation of the Fourier transform of $\cos\beta$, factor $\cos\beta$ is written as $$\cos\beta=\cos[\beta(T)+\dot{\beta}(T)(t-T)]\cos[\beta(t)-T)-\dot{\beta}(T)(t-T)]-\sin[\beta(T)+\dot{\beta}(T)(t-T)]\sin[\beta(t)-\beta(T)-\dot{\beta}(T)(t-T)] \qquad (9)$$

and factors $\cos[\beta(t)-\beta(T)-\dot{\beta}(T)(t-T)]$ and $\sin[\beta(t)-\beta(T)-\dot{\beta}(T)(t-T)]$ in Eq. (9) are expanded in Taylor's series about t=T where $\dot{\beta}(T)=[d\beta/dt]_{t=T}$. The Taylor's series expansions including terms up through fifth order in (t−T) may be expressed according to the formulae $$\cos[\beta(t)-\beta(T)-\dot{\beta}(T)(t-T)] = 1 - 3[\ddot{\beta}(T)]^2\frac{(t-T)^4}{4!} - \qquad (10)$$
$$10\ddot{\beta}(T)\dddot{\beta}(T)\frac{(t-T)^5}{5!} + \ldots,$$

$$\sin[\beta(t)-\beta(T)-\dot{\beta}(T)(t-T)] = \ddot{\beta}(T)\frac{(t-T)^2}{2!} + \qquad (11)$$
$$\dddot{\beta}(T)\frac{(t-T)^3}{3!} + \overset{IV}{\beta}(T)\frac{(t-T)^4}{4!} +$$
$$\overset{V}{\beta}(T)\frac{(t-T)^5}{5!} + \ldots,$$

where $$\ddot{\beta}(T) = [d^2\beta/dt^2]_{t=T}, \dddot{\beta}(T) = [d^3\beta/dt^3]_{t=T}, \overset{IV}{\beta}(T) = [d^4\beta/dt^4]_{t=T},$$

and $$\overset{V}{\beta}(T) = [d^5\beta/dt^5]_{t=T}.$$

For a given term in $s_{2,\psi}$, the corresponding second and higher order derivatives of $\beta$ with respect to time are proportional to second and higher order derivatives of $\phi_2$ with respect to time, respectively, with a proportionally constant determined by properties of the respective sinusoidal factor in the given term. The proportionally constant may be zero or non-zero. The Fourier transform of $\cos t$ over time interval T−τ/2 to T+τ/2 can be expressed, using representations in Eqs. (9), (10), and (11), as $$F(\cos\beta) = \tau\frac{e^{i\omega T}}{2\sqrt{2\pi}}\left(\left(e^{i\beta(T)}C^+\left\{\frac{[\omega+\dot{\beta}(T)]\tau}{2}\right\}+\right.\right. \qquad (12)$$
$$\left.\left.e^{-i\beta(T)}C^-\left\{\frac{[\omega-\dot{\beta}(T)]\tau}{2}\right\}\right)\right),$$

where $$C^+(x) = j_0\left(\frac{x}{2}\right) - g_2\left(\frac{x}{2}\right)\left(\frac{1}{2!}\right)\left(\frac{\tau}{2}\right)^2\ddot{\beta}(T) - \qquad (13)$$
$$g_3\left(\frac{x}{2}\right)\left(\frac{1}{3!}\right)\left(\frac{\tau}{2}\right)^3\dddot{\beta}(T) -$$
$$g_4\left(\frac{x}{2}\right)\frac{1}{4!}\left(\frac{\tau}{2}\right)^4\left\{\overset{IV}{\beta}(T) + 3[\ddot{\beta}(T)]^2\right\} -$$
$$g_5\left(\frac{x}{2}\right)\frac{1}{5!}\left(\frac{\tau}{2}\right)^5\left\{\overset{V}{\beta}(T) + 10\ddot{\beta}(T)\dddot{\beta}(T)\right\} + \ldots,$$

$$C^-(x) = j_0\left(\frac{x}{2}\right) + g_2\left(\frac{x}{2}\right)\left(\frac{1}{2!}\right)\left(\frac{\tau}{2}\right)^2\ddot{\beta}(T) + \qquad (14)$$
$$g_3\left(\frac{x}{2}\right)\left(\frac{1}{3!}\right)\left(\frac{\tau}{2}\right)^3\dddot{\beta}(T) +$$
$$g_4\left(\frac{x}{2}\right)\frac{1}{4!}\left(\frac{\tau}{2}\right)^4\left\{\overset{IV}{\beta}(T) - 3[\ddot{\beta}(T)]^2\right\} +$$
$$g_5\left(\frac{x}{2}\right)\frac{1}{5!}\left(\frac{\tau}{2}\right)^5\left\{\overset{V}{\beta}(T) + 10\ddot{\beta}(T)\dddot{\beta}(T)\right\} + \ldots,$$

$$g_1(x) = \frac{i}{2}j_1(x), \qquad (15)$$

-continued $$g_2(x) = \frac{1}{3}[j_0(x) - 2j_2(x)], \quad (16)$$

$$g_3(x) = \frac{i}{5}[3j_1(x) - 2j_3(x)], \quad (17)$$

$$g_4(x) = \frac{1}{35}[7j_0(x) - 20j_2(x) = 8j_4(x)], \quad (18)$$

$$g_5(x) = \frac{i}{63}[27j_1(x) - 28j_3(x) + 8j_5(x)], \quad (19)$$

and $j_n(x)$, $n=0,\pm1,\pm2,\ldots$, is the spherical Bessel function of the first kind and order n [see Chapter 10 of *Handbook of Mathematical Functions*, Eds. M. Abramowitz and I. Stegun, Nat. Bureau of Standards Applied Mathematics Series 55]. The coefficients for $g_n(x)$ in terms of $j_m(x)$ are the same as the coefficients for xf in terms of $P_m(x)$, the Legendre polynominal of degree m, multiplied by $(i)^m$ [see Eq. 10.1.14 and Table 22.9 in Abramowitz and Stegun, ibid.].

In electronic processor 153, the complex spectral coefficients of coherent cyclic errors are extracted using the complex values of the Fourier transform $F(s_2)$ at the subset of frequencies of $\omega_{2,v}$ and $\omega_{2,v,A}$ and normalized for the effects of non-zero second and higher order time derivatives of $\dot{\phi}_2$. The normalizations for non-zero second and higher order derivatives of β are obtained using Eqs. (8), (12), (13), and (14). Values for the second and higher order time derivatives of $\dot{\phi}_2$ are obtained form the output of electronic processor 156 in an iterative procedure. The number of higher order derivatives of $\dot{\phi}_2$ that must be included in making the corrections for non-zero second and higher order time derivatives of $\dot{\phi}_2$ is determined in part by the magnitude of τ and in part by the magnitudes of the second and higher order time derivatives of $\dot{\phi}_2$.

There is a set of values of $\dot{\phi}_2$ for which certain of the subset of corresponding frequencies $\omega_{2,v}$ and $\omega_{2,v,A}$ and the frequency of the dominant complex peak in $F(s_2)$ comprise two or more frequency values that are separated by less than or of the order of the angular frequency resolution of the Fourier transform $F(s_2)$. For the set of values of $\dot{\phi}_2$, the respective values of $F(s_2)$ represent superimposed values of respective Fourier transforms of coherent cyclic errors and the dominant complex peak in $F(s_2)$ and are not included in the values of complex spectral coefficients determined by electronic processor 153. The values of complex spectral coefficients determined by electronic processor 153 are transmitted to electronic processor 154.

Electronic processor 154 filters with respect to time the values of the normalized complex spectral coefficients received from electronic processor 153 and interpolates the filtered, normalized values to determine complex spectral coefficients of the coherent cyclic errors not included in the values of filtered, normalized complex spectral coefficients determined by electronic processor 153. If the normalized, filtered, and interpolated values of the complex spectral coefficients are determined to be dependent on $\dot{\phi}_2$, the $\dot{\phi}_2$ dependence of the normalized, filtered, and interpolated values of the complex spectral coefficients may effectively be represented in a power series, orthogonal functions, or orthogonal polynomials of $\dot{\phi}_2$.

The determined the set of normalized, filtered, and interpolated values of the complex spectral coefficients are transmitted to electronic processor 155 wherein a computed value of $s_{2,\psi}$, $s_{2,\psi,M}$, is generated.

There is a type of coherent cyclic error with a corresponding coherent cyclic error amplitude and phase offset that depends on an orientation of a measurement object mirror. This type of coherent cyclic error will hereinafter be referred to as a variable coefficient type of coherent cyclic error. For those end use applications where tilt and yaw of the measurement object mirror are measured and monitored to a requisite accuracy, e.g., measured by interferometric means, the variable coefficient type of coherent cyclic error can be measured and compensated within the framework of the present invention.

The cyclic error complex amplitude in the coherent cyclic error representation for a variable coefficient type of coherent cyclic error will comprise a complex multiplicative factor. The variable type of coherent cyclic error will subsequently be described in terms of two subtypes. The complex multiplicative factor for a first subtype of the two subtypes will generally be function of the degree of overlap of a ghost beam and a non-ghost beam components or of two ghost beam components of an output beam and the function can be modeled and/or measured experimentally. For the first subtype, the wavefronts of corresponding ghost beam and non-ghost beam components or two ghost beam components of the output beam are parallel independent of the orientation of the object mirror. The complex multiplicative factor of a second subtype of the two subtypes will generally be a function of the degree of overlap of a ghost beam and a non-ghost beam components or of two ghost beam components of an output beam and the wedge angle between the wavefronts of the corresponding ghost beam and the non-ghost beam components or of the two corresponding ghost beam components of the output beam. For the second subtype, the wavefronts of the corresponding ghost beam and the non-ghost beam components or of the two corresponding ghost beam components of the output beam will be substantially parallel for a particular orientation of the measurement object mirror. The properties of the complex multiplicative factor will be analogous to properties of a fringe visibility function and can be modeled and/or measured experimentally.

For those end use applications where the variable coefficient type of coherent cyclic error can be eliminated by tilting of certain optical elements or portions thereof, information on the tilt and yaw can be used to ascertain when the variable coefficient type of coherent cyclic error is sufficiently small as to be negligible.

Complex amplitudes in a spectral representation of coherent cyclic errors in $s_{2,\psi}$ will also depend on the magnitude of $s_2$. The dependence of the complex amplitudes on the magnitude of $s_2$ can be measured and compensated within the framework of the present invention. The complex amplitudes in the coherent cyclic error spectral representation will comprise complex multiplicative factors. The complex multiplicative factor for a specific coherent cyclic error spectral component will be a function of $s_2$ and easily represented as a power series in $s_2$. The power series representation will be determined from measured properties of the respective specific complex amplitude as the magnitude of $s_2$ is varied. For certain interferometer and detector systems, the power series representation can be determined from a corresponding value of q associated with the corresponding value of $\omega_{2,v}$ or $\omega_{2,v,A}$.

One of the more subtle types of coherent cyclic errors to identify and compensate has a $\omega_{2,v}$ that is the same as the angular frequency of the dominant peak in $|F(s_2)|^2$ independent of the value of $\dot{\phi}_2$. This type of coherent cyclic error will be referred to hereinafter as a zero-frequency-shift coherent cyclic error. Sources of zero-frequency-shift coherent cyclic errors generally comprise nonlinearities with odd order values of nonlinearity index q greater than 1, e.g. q=3,5,....

The primary zero-frequency-shift coherent cyclic errors arise in Eq. (2) from terms with u=1, u'=0, p=1, p⁺=0, and $q_R=1$ and can be expressed as $$\sum_{q=3,5,\ldots} \{(a_{2,1,0,1,0})^q B_{2,1,0,1,0,q,1} \cos\left[(\omega_2 t + \varphi_2) + \zeta_{2,1,0,1,0,q,1}\right]\}. \quad (20)$$

Other zero-frequency-shift coherent cyclic errors not represented in Eq. (20) arise in Eq. (2) for different values and combination of values of u, p, and p⁺. The terms omitted in Eq. (20) arise from nonlinear coupling between the dominant term with amplitude $a_{2,1,0,1,0}$ and other cyclic error terms and therefore are generally several orders of magnitude smaller. It is evident from Eq. (20) that the zero-frequency-shift coherent cyclic errors modify the amplitude and phase offset of the measured spectral component of $s_2$ having a phase of $(\omega_2 t + \phi_2)$ with the modifications depending on properties of coherent cyclic errors present.

Thus the effects of zero-frequency-shift coherent cyclic errors are manifested in $s_2$ not as cyclic errors but as errors that modify a phase offset at the frequency of the dominant peak in $|F(s_2)|^2$ over a range of operating conditions for the apparatus of the first embodiment. In particular, the zero-frequency-shift coherent cyclic errors alter the group delay properties of $s_2$ at the frequency of the dominant peak in $|F(s_2)|^2$. It is therefore evident that the effect of the zero-frequency-shift coherent cyclic errors are compensated in the first embodiment for the case when the effects of group delay at the frequency of the dominant peak in $|F(s_2)|^2$ are measured for a system comprising an interferometer and associated electric signal processors. Preferably, the measurement is performed with the measurement leg of the interferometer in vacuum to prevent the affects of air turbulence on the characterization of $\phi$.

For the case where the zero-frequency-shift coherent cyclic error terms in $F(s_2)$ are not compensated as part of a procedure for compensation for group delay effects, two procedures are described in the following paragraphs for isolating and detecting effects of the zero-frequency-shift coherent cyclic errors.

Characterization of the zero-frequency-shift errors can be important because the phase offset they produce in the dominant peak of $|F(s_2)|^2$ will vary with the intensity of the measurement and reference beams and the relative overlap of the beams that produce the optical interference signal—parameters that may change during operation of the interferometry system. Furthermore, the phase offset may additionally vary with the Doppler shift.

The first of the two procedures described for isolating and detecting effects of the zero-frequency-shift coherent cyclic errors is the simpler of the two procedures to implement although of a restricted domain of applicability. For each coherent cyclic error of the set of zero-frequency-shift coherent cyclic errors, there are corresponding coherent cyclic errors with values of $\omega_{2,v}$ that are different from the angular frequencies of the dominant peak in $|F(s_2)|^2$. For example, for an odd order nonlinearity order index of $q=n \geq 3$, the set of different $\omega_{2,v}$ may be written as $3\omega_d$, $5\omega_d$, . . . ,$n\omega_d$ where $\omega_d$ is the angular frequency of the dominant complex peak in $F(s_2)$. For a $F(s_2)$ where the corresponding coherent cyclic errors correspond to only one value of n, ratios of coefficients of the zero-frequency-shift coherent cyclic error and of the corresponding coefficients of the zero-frequency-shift coherent cyclic errors are specified for certain apparatus by coefficients comprising ratios of $B_{q,n}$ for respective values of n. Electronic processor 154 examines the set of corresponding coherent cyclic errors coefficients and determines the value of the zero-frequency-shift coherent cyclic error coefficient using the ratios between the coefficients of the zero-frequency-shift coherent cyclic errors and of the set of corresponding coherent cyclic error coefficients. For a case where more the one value of q is required in the description of the corresponding coherent cyclic errors, the corresponding zero-frequency-shift coherent cyclic error coefficients can be determined from a least squares analysis of set of corresponding coherent cyclic error coefficients, a set of corresponding simultaneous equations, and a set of corresponding binomial coefficients.

Effectiveness of the first procedure for isolating and detecting effects of the zero-frequency-shift coherent cyclic errors is diminished when the set of different $\omega_{2,v}$ include angular frequencies where the transfer function of the analog portion of detector 185 generating $s_2$ is not substantially constant.

The second procedure described for isolating and detecting effects of the zero-frequency-shift coherent cyclic errors is based on the use of two input beams 109 and 109T (beam 109T is not shown in FIG. 2a). Beam 109T is similar to beam 109 in that it has two orthogonally polarized components having a frequency splitting $\omega_{2,T}$. However, the frequency splitting 02T between the components of beam 109T is selected to be different from the frequency splitting $\omega_2$ between the components of beam 109. The absolute value of the difference between the frequency splittings, $|\omega_{2,T}-\omega_2|$, is selected to be less than both $\omega_2+\phi$ and $\omega_{2,N_y}$. Beam 109T propagates through interferometer 169 and detector 189 to generate an interference signal component $s_{2,T}$ in signal 123. The description of $s_{2,T}$ is the same as corresponding portions of the description given for $s_2$. The properties of the apparatus of the first embodiment that generate the zero-frequency-shift coherent cyclic errors also generate a closely spaced multiplet with respect to frequency in the power spectrum of $s_2+s_{2T}$ when beam 109T is present. The frequency spacing between contiguous members of the multiplet is equal to the frequency separation of beams 109 and 109T. The amplitude and phase of the zero-frequency-shift coherent cyclic errors can be expressed by a relationship in terms of amplitudes and phases of members of the multiplet. In the procedure to isolate the zero-frequency-shift coherent cyclic errors, the primary zero-frequency-shift coherent cyclic errors are determined using the relationship and measured amplitudes and phases of the members of the multiplet.

Figure 2E:
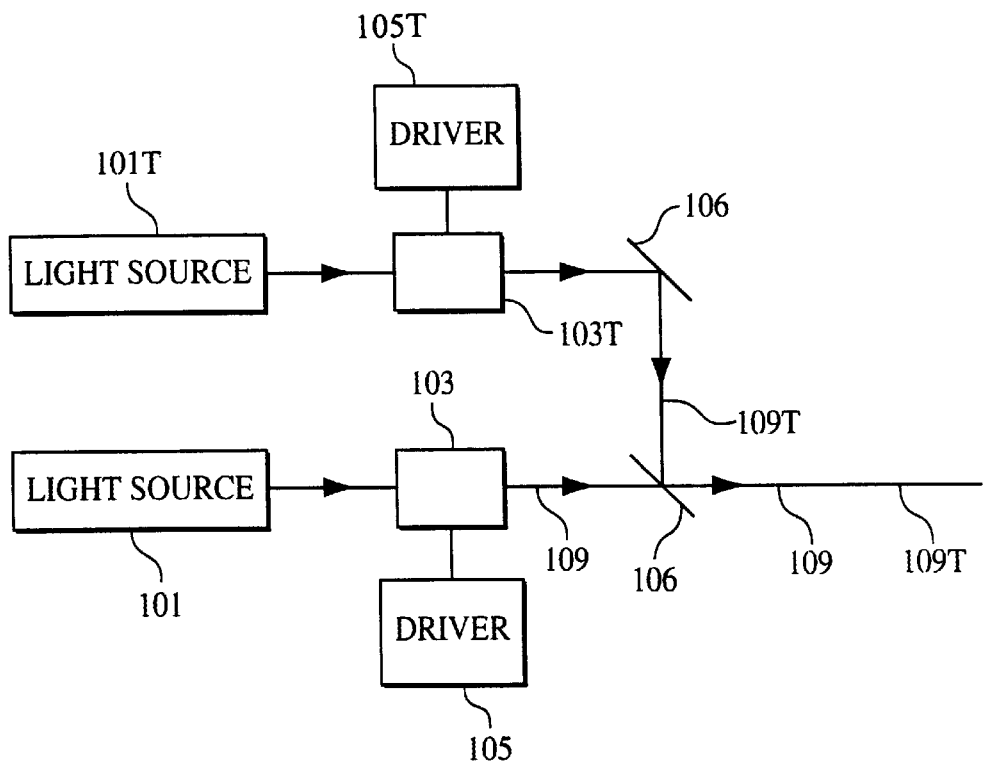
FIGS. 2e and 2f are schematic diagrams of different embodiments for a source to produce to two input beams for the interferomery system of FIG. 2a to quantify zero-frequency-shift cyclic errors.
Figure 2F:
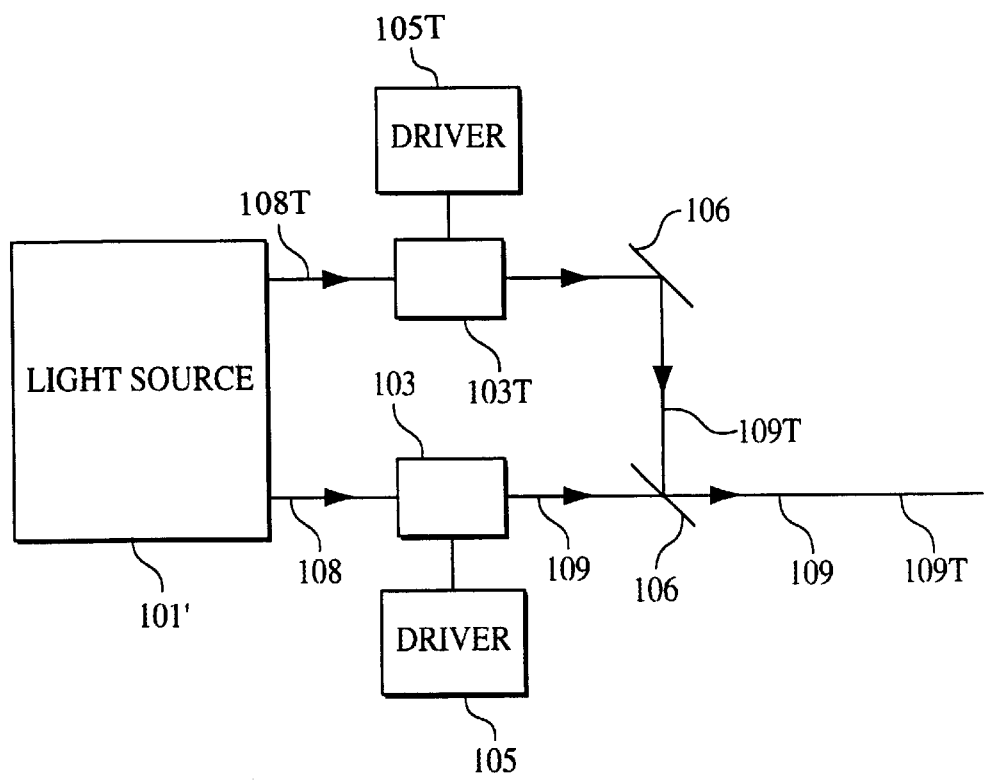

The description of the source of beam 109T (source of beam 109T is not shown in FIG. 2a) is the same as corresponding portions of the description given for the source of beam 109. For example, as shown in FIG. 2e, the interferometry system can include a first source for beam 109 including light source 101 and modulator 103 excited by driver 105, a second source for beam 109T including another light source 101T and another modulator 103T excited by another driver 105T, and optics 106 to combine the beams produced by the first and second sources. In another embodiment shown in FIG. 2f, beams 109 and 109T are both derived from the same light source, laser 101'. For example, laser 101' can produce two beams 108 and 108T corresponding to different longitudinal modes of laser 101'. Modulators 103 and 103T excited by drivers 105 and 105T, respectively, then act on beams 108 and 108T to produce input beams 109 and 109T. In further embodiments, a single modulator driven at both split frequencies, $\omega_2$ and $\omega_{2,T}$, can be used. As necessary, the intensity of beams 109 and 109T may be adjusted as may the frequency splittings. For example, the source for beam 109T can remove it from the interferometry system once the zero-frequency-shift cyclic errors are characterized.

Generally, the difference between the average frequency of the components of beam 109 and the average frequency of the components of beam 109T is selected to be greater than the Nyquist frequency $\omega_{2,Ny}$, e.g., twice as great as the Nyquist frequency $\omega_{2,Ny}$, to minimize terms in the signal generated by detector 189 corresponding to interference between beams 109 and 109T other than in the zero-frequency-shift multiplet. Conversely, the frequency splittings themselves are selected to be smaller than the Nyquist frequency. Generarally, the absolute value of the difference between the frequency splittings $|\omega_{2,T}-\omega_2|$ is selected to be smaller than either of the frequency splittings themselves to minimize spectral overlap of the multiplet with other cyclic errors and to minimize any difference between the zero-shift-frequency cyclic error coefficients in $s_2$ and $s_{2,T}$. For example, $|\omega_{2,T}-\omega_2|$ can be selected so that $|\omega_{2,T}-\omega_2|<(\omega_2/100)$.

The zero-frequency-shift cyclic errors are determined from a Fourier analyses of terms in $s_2+s_{2T}$ such as $[a_v \cos(\omega_2 t+\phi_2+\zeta_v)+a_{vT}\cos(\omega_{2T}t+\phi_{2T}+\zeta_{vT})]^q$ where $v=(2,1,0,1,0)$ and $q=3,5,\ldots$. Results from such an analysis are listed for examples of $q=3,5$, and 7. Results for other values of $q$, as required in a particular end use application, can be generated by the same procedure. For $q=3$, the primary terms contributing to the multiplet are $$(a_v)^3 B_{v3,1} \begin{cases} x\cos[\alpha_{2,3}-(\alpha_{2,3T}-\alpha_{2,3})] + \\ (1+2x^2)\cos\alpha_{2,3} + \\ x(2+x^2)\cos[\alpha_{2,3}+(\alpha_{2,3T}-\alpha_{2,3})] + \\ x^2\cos[\alpha_{2,3}+2(\alpha_{2,3T}-\alpha_{2,3})] \end{cases} \quad (21)$$

where $$x = \frac{a_{vT}}{a_v}, \quad (22)$$

$$\alpha_{2q}=\omega_2 t+\phi_2+\zeta_{vq,1}, \quad (23)$$

$$\alpha_{2qT}=\omega_{2T}t+\phi_{2T}+\zeta_{vq,1T}, \quad (24)$$

$$\alpha_{2qT}-\alpha_{2q}=L_2 p_2 n_2(k_{2T}-k_2)+(\zeta_{2qT}-\zeta_{2q}), \quad (25)$$

Note the quantity $(k_{2T}-k_2)$ is simply $2\pi/c$ times the difference in frequency of beams 109 and 109T.

For $q=5$, the primary terms contributing to the multiplet are $$(a_v)^5 B_{v5,1} \begin{cases} x^2\cos[\alpha_{2,5}-2(\alpha_{2,5T}-\alpha_{2,5})] + \\ x(2+3x^2)\cos[\alpha_{2,5}-(\alpha_{2,5T}-\alpha_{2,5})] + \\ (1+6x^2+3x^4)\cos\alpha_{2,5} + \\ x(3+6x^2+x^4)\cos[\alpha_{2,5}+(\alpha_{2,5T}-\alpha_{2,5})] + \\ x^2(3+2x^2)\cos[\alpha_{2,5}+2(\alpha_{2,5T}-\alpha_{2,5})] + \\ x^3\cos[\alpha_{2,5}+3(\alpha_{2,5T}-\alpha_{2,5})] \end{cases} \quad (26)$$

For $q=7$, the primary terms contributing to the multiplet are $$(a_v)^7 B_{v7,1} \begin{cases} x^3\cos[\alpha_{2,7}-3(\alpha_{2,7T}-\alpha_{2,7})] + \\ x^2(3+4x^2)\cos[\alpha_{2,7}-2(\alpha_{2,7T}-\alpha_{2,7})] + \\ 3x(1+4x^2+2x^4)\cos[\alpha_{2,7}-(\alpha_{2,7T}-\alpha_{2,7})] + \\ (1+12x^2+18x^4+4x^6)\cos\alpha_{2,7} + \\ x(4+18x^2+12x^4+x^6)[\alpha_{2,7}+(\alpha_{2,7T}-\alpha_{2,7})] + \\ 3x^2(2+4x^2+x^4)\cos[\alpha_{2,7}+2(\alpha_{2,7T}-\alpha_{2,7})] + \\ x^3(4+3x^2)\cos[\alpha_{2,7}+3(\alpha_{2,7T}-\alpha_{2,7})] + \\ x^4\cos[\alpha_{2,7}+4(\alpha_{2,7T}-\alpha_{2,7})] \end{cases} \quad (27)$$

Since the magnitude of the angular frequency separation is chosen to be much less than both $\omega_2+\dot\phi$ and $\omega_{2,Ny}$, the coefficient $B_{vq,1}$ is used to a good approximation for both the representation of corresponding terms in $s_2$ and $s_{2T}$.

The terms in Eqs. (21), (26), and (27) are arranged according to the respective locations in respective multiplets. Note that the largest terms of the zero-frequency-shift coherent cyclic error in $s_2$ is a sum of the coefficients $(a_v)^3 B_{v3,1} \cos \alpha_{2,3}, (a_v)^5 B_{v5,1} \cos \alpha_{2,5}, (a_v)^7 B_{v7,1} \cos \alpha_{2,7}, \ldots$. Further, note that the phase difference $(\alpha_{2qT}-\alpha_{2q})$ for multiplet $q$ can be obtained directly from the difference of the measured phases of the two terms corresponding to the lowest and highest frequency components of the respective multiplet, that difference being equal to $q(\alpha_{2qT}-\alpha_{2q})$.

Continuing with the description of the procedure for isolating and detecting effects of the zero-frequency-shift coherent cyclic errors, electronic processor 154 examines the normalized, filtered, and interpolated values of the complex spectral coefficients for the set of complex spectral coefficients corresponding to the terms in the multiplet. The zero-frequency-shift coherent cyclic error in $s_2$, the sum of the coefficients $(a_v)^3 B_{v3,1} \cos \alpha_{2,3}, (a_v)^5 B_{v5,1} \cos \alpha_{2,5}, (a_v)^7 B_{v7,1} \cos \alpha_{2,7}, \ldots$, is determined from a least squares analysis of the set of complex spectral coefficients using equations describing terms contributing to the multiplet such as found in Eqs. (21), (26), and (27). The number of terms in the sum of the coefficients $(a_v)^3 B_{v3,1} \cos \alpha_{2,3}, (a_v)^5 B_{v5,1} \cos \alpha_{2,5}, (a_v)^7 B_{v7,1} \cos \alpha_{2,7}, \ldots$ that need to be included is determined by the magnitudes of the terms and a required accuracy in the compensation for the zero-frequency-shift coherent cyclic error in $s_2$.

Electronic processor 154 as previously cited filters the values of the normalized complex spectral coefficients received from electronic processor 153 and interpolates the normalized, filtered values to determine values of the coherent cyclic errors not included in the values of complex spectral coefficients determined by electronic processor 153. If the normalized, filtered, and interpolated values of the complex spectral coefficients are determined to be dependent on $\dot\phi_2$, the $\dot\phi_2$ dependence of the normalized, filtered, and interpolated values of the complex spectral coefficients may effectively be represented in a power series, a series of orthogonal functions, or a series of orthogonal polynomials in $\dot\phi_2$. The set of zero-frequency-shift coherent cyclic errors, if determined, and the determined values of the normalized, filtered, and interpolated values of the complex spectral coefficients are transmitted to electronic processor 155 wherein a simulated value of $s_{2,\psi}$, $s_{2,\psi,M}$, is generated. Simulated valued $s_{2,\psi,M}$ and $s_2$ are transmitted to electronic processor 152 where $s_{2,\psi,M}$ is subtracted from $s_2$ to yield $s_2-s_{2,\psi,M}$. Signal $s_2-s_{2,\psi,M}$ and frequency $\omega_2$ are transmitted to electronic processor 156 where phase $\phi_2$ is determined preferably by a sliding window FFT or other like phase detector. Phase $\phi_2$ is transmitted to computer 129 as signal 128 for use in determining linear displacements of object 192 not effected by coherent cyclic errors.

It was noted in the description of the first embodiment that the different contributions to the cyclic errors were generally the result of imperfections in the source of beam 109, in the components of interferometer 169, in detector system 189, and/or in electronic processor 127. It is also evident from the description that properties of a cyclic error term with respect to frequency and amplitude generally permit identification of the origin of the cyclic error term, i.e. with respect to a particular type of imperfection. For example, cyclic errors associated with the set of frequencies $\omega'_{2u'}$ indicate an intensity fluctuation in beam 109 that could be due to an imperfection in the acousto-optic modulator 103, in the power supply system of source 101, and/or an instability in the laser. A cyclic error term associated with the frequency $\phi$ could be due to polarization mixing in beam 109 and/or due to an imperfection in the polarizing beam splitter interface 171. A cyclic error term associated with the parameter q indicates a nonlinearity in detector system 189 and/or electronic processor 127.

Consequently, degradation in performance of one or more components of an interferometer system can be detected by monitoring properties of the cyclic error terms as described above with reference to FIG. 1. Such detection of degradation generally amounts to an early detection system, i.e. an opportunity is afforded for implementation of corrective measures that can generally be implemented before the interferometer system is used in a mode unacceptable for a given end use application. The corrective measures can, for example, be part of a programmed maintenance to correct for a degraded component in a problem area indicated by the properties of the associated cyclic error term. Furthermore, indication of the problem area by properties of the associated cyclic error term can substantially improve the efficiency of executing the corrective measures.

The description of the first embodiment noted that the configuration of interferometer illustrated in FIG. 2a is known in the art as polarized Michelson interferometer. Other forms of the Michelson interferometer and forms of other interferometers such as the high stability plane mirror interferometer, or the angle-compensating interferometer or similar device such as is described in an article entitled "Differential interferometer arrangements for distance and angle measurements: Principles, advantages and applications" by C. Zanoni, *VDI Berichte Nr.* 749, 93–106 (1989), may be incorporated into the apparatus of the present invention, the foregoing article being herein incorporated by reference, as when working with stages commonly encountered in the lithographic fabrication of integrated circuits without departing from the spirit or scope of the present invention.

Other forms of interferometer described in copending commonly owned U.S. patent applications with Ser. No. 09/157,131 filed Sep. 18, 1998 entitled "Interferometer Having A Dynamic Beam Steering Assembly" by Henry A. Hill and Peter de Groot; Ser. No. 09/305,828 filed May 5, 1999 entitled "Interferometry System Having A Dynamic Beam Steering Assembly For Measuring Angle And Distance" by Henry A. Hill; Ser. No. 09/384,742 filed Aug. 27, 1999 entitled "Polarization Preserving Optical Systems" by Henry A. Hill; Ser. No. 09/384,609 filed Aug. 27, 1999 entitled "Interferometer Having Reduced Ghost Beam Effects" by Peter de Groot; and Ser. No. 09/384,855 filed Aug. 27, 1999 entitled "Interferometers Utilizing Polarization Preserving Optical Systems" by Henry A. Hill may be incorporated into the apparatus of the present invention, the foregoing applications being herein incorporated by reference, without departing from the spirit or scope of the present invention.

FIG. 2c depicts in schematic form, in accordance with the preferred apparatus and method of a variant of the first embodiment, electronic processor 127A. The variant of the first embodiment is from the first category of embodiments of the several different categories and comprises beam 109, source of beam 109, interferometer 169, detector system 189, and digital computer 129 of the first embodiment shown in FIG. 2a and electronic processor 127A shown in FIG. 2c.

Electronic processor 127A comprises certain elements that perform like functions as like numbered elements of electronic processor 127 of the first embodiment. In the operation of electronic processor 127A, as shown in FIG. 3c, signal $(s_2-s_{2,\psi,M})$ generated by electronic processor 152 is transmitted to electronic processor 156 and electronic processor 151B. Electronic processor 151B generates a Fourier transform $F(s_2-s_{2,\psi,M})$ of $(s_2-s_{2,\psi,M})$ and $F(s_2-s_{2,\psi,M})$ is transmitted to electronic processor 153 of 127A.

Non-zero complex spectral coefficients in $F(s_2-s_{2,\psi,M})$ represent in complete compensation for coherent cyclic errors in $s_2$. Incomplete compensation for coherent cyclic errors in $s_2$ can be the result for example of changes of coherent cyclic errors with respect to time and/or the result of statistical errors in measured quantities. Incomplete compensation will generally be present during an initialization phase for establishing a multidimensional array of normalized, filtered, and interpolated complex spectral coefficients by electronic processor 154A. Electronic processor 153 of 127A determines the complex spectral coefficients of $F(s_2-s_{2,\psi,M})$ and the complex spectral coefficients are transmitted to electronic processor 154A. Electronic processor 154A processes the complex spectral coefficients representing an incomplete compensation of coherent cyclic errors in $s_2$ and updates the multidimensional array of normalized, filtered, and interpolated complex spectral coefficients. Electronic processor 154A otherwise processes the multidimensional array of normalized, filtered, and interpolated complex spectral coefficients the same as electronic processor 154 of processor 127 of the first embodiment.

The remaining description of the variant of the first embodiment is the same as corresponding portions of the description given for the first embodiment.

Figure 3A:
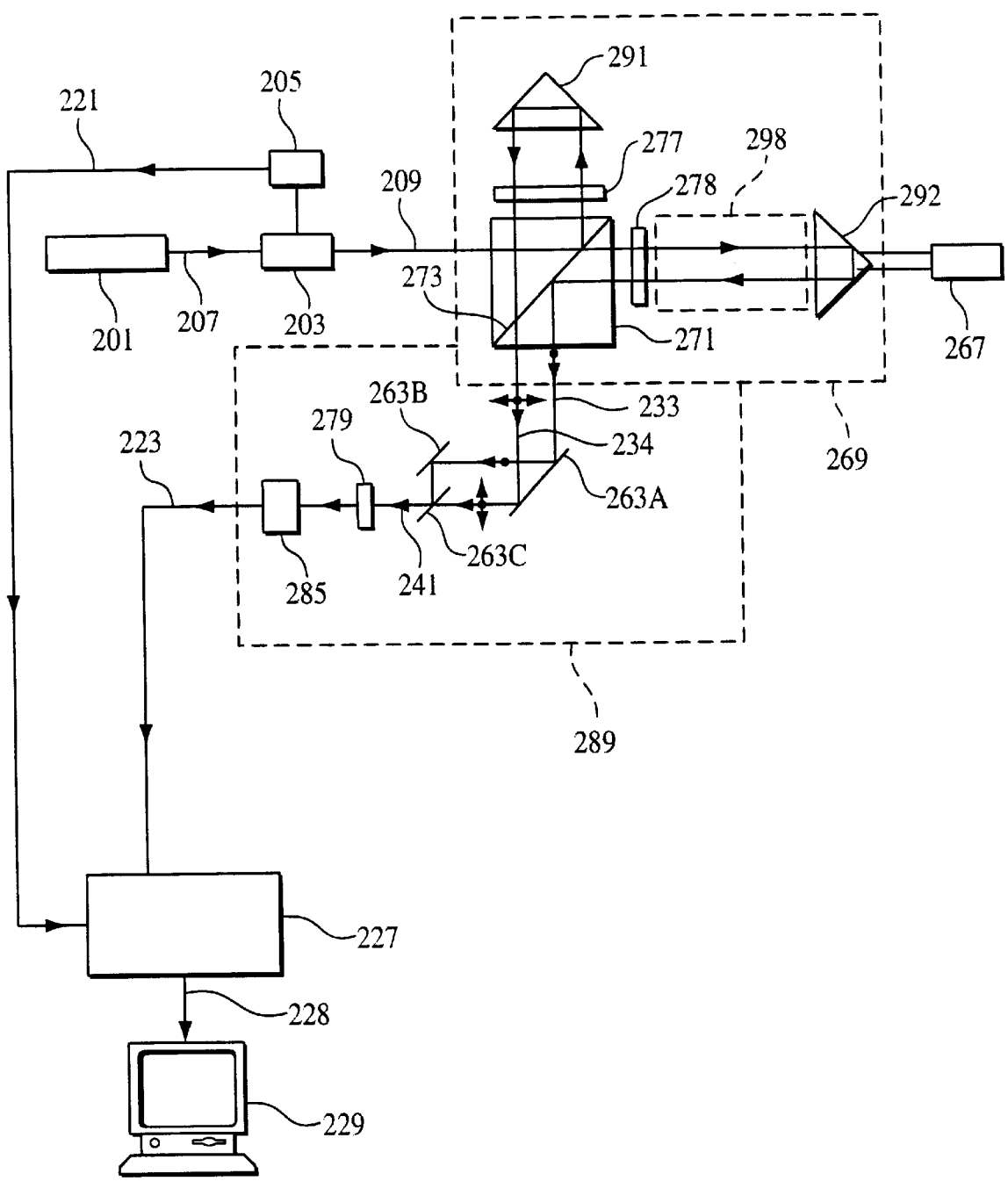
FIG. 3a is schematic diagrams of a second embodiment of an interferometry system that quantifies nonlinearities.

FIG. 3a depicts in schematic form an apparatus and method in accordance with the second embodiment of the present invention. The second embodiment is from the second category of embodiments. The interferometer depicted in FIG. 3a is a polarizing, heterodyne, single pass interferometer. Although the described embodiment is a heterodyne system, the instant invention is readily adapted for use in a homodyne system in which the reference and measurement beams have the same frequencies.

Descriptions of a source of beam 209 and of beam 209 of the second embodiment are the same as the corresponding portions of the descriptions given for the source of beam 109 and of beam 109 of the first embodiment. Also descriptions of interferometer 269 and detector system 289 of the second embodiment are the same as corresponding portions of the descriptions given for interferometer 169 and detector system 189 of the first embodiment. Elements of the second embodiment comprising the source of beam 209 and beam 209, interferometer 269, and detector system 289 perform like functions as like numbered elements, decremented by 100, of the first embodiment comprising the source of beam 109 and beam 109, interferometer 169, and detector system 189.

Interferometer 269 introduces phase shift $\phi_3$ between the first and second components of beam 241 so that beam 241 is a phase-shifted beam. The magnitude of phase shift $\phi_3$ is related to round-trip physical length $L_3$ of measurement path 298 according to the formula $$\phi_3 = L_3 p_3 k_3 n_3 \tag{28}$$

where $p_3$ is the number of passes through the respective reference and measurement legs, $n_3$ is the refractive index of a gas in measurement path 298 corresponding to the optical path introducing the phase shift $\phi_3$ and to wavenumber $k_3 = 2\pi/\lambda_3$, and $\lambda_3$ is the wavelength of beam 207. The interferometer shown in FIG. 3a is for $p_3=1$ so as to illustrate in the simplest manner the function of the apparatus of the second embodiment. To those skilled in the art, generalization to the case when $p_3 \neq 1$ is a straight forward procedure. The value for $L_3$ corresponds to twice the difference between the physical length of measurement path 298 and an associated reference path.

In a next step as shown in FIG. 3a, phase-shifted beam 241 passes through polarizer 279, impinges upon photodetector 285, and generates an electrical interference signal, heterodyne signal $s_3$, preferably by photoelectric detection. Polarizer 279 is oriented so as to mix polarization components of phase-shifted beam 241. Signal $s_3$ has the form $$s_3 = A_3(t)\cos[\alpha_3(t)] \tag{29}$$

where $A_3(t)$ and $\alpha_3(t)$ are the amplitude and phase of $s_3$, respectively.

The signal $s_3$ is the real part, $\hat{s}_{3,R}$, of a complex signal $\hat{s}_3$ where $s_3$ comprises a causal, stable, i.e., absolutely summable, real sequence. Thus, the Fourier transform $S_{3,R}$ ($i\omega$) of $s_3$ completely defines $S_3(i\omega)$ [see Chapter 10 "Discrete Hilbert Transforms" in *Discrete-Time Signal Processing*, (Prentice Hall, 1989) by A. V. Oppenheim and R. W. Schafer] where $$S_3(i\omega) = S_{3,R}(i\omega) + S_{3,I}(i\omega), \tag{30}$$

$S_{3,I}(i\omega)$ is the imaginary component of $S_3(i\omega)$, $\omega$ is an angular frequency, and $i$ is the imaginary number $\sqrt{(-1)}$. $S_{3,I}(i\omega)$ is related to $S_{3,R}(i\omega)$) by a frequency response function, $H(i\omega)$, i.e.

$$S_{3,I}(i\omega) = H(i\omega) S_{3,R}(i\omega), \tag{31}$$

where the frequency response function $H(i\omega)$ is given by the equation $$H(i\omega) = \begin{cases} -i, & 0 < \omega, \\ i, & \omega < 0. \end{cases} \tag{32}$$

Imaginary component $\hat{s}_{3,I}$ of $\hat{s}_3$ is obtained from the inverse Fourier transform of $S_{3,I}(i\omega)$ with $$\hat{s}_{3,I} = A_3(t)\sin[\alpha_3(t)]. \tag{33}$$

The phase $\alpha_3$ can be obtained from $\hat{s}_{3,R}$ and $\hat{s}_{3,I}$ according to the formula $$\alpha_3(t) = \arctan\left(\frac{\hat{s}_{3,I}}{\hat{s}_{3,R}}\right). \tag{34}$$

Time-dependent argument $\alpha_3$ is expressed in terms of other quantities according to the formula $$\alpha_3 = 2\pi f_3 t + \phi_3 + \psi_3 + \zeta_3 \tag{35}$$

where $\psi_3$ comprises the non-linear cyclic error terms and phase offset $\zeta_3$ comprises all contributions to phase $\alpha_3$ that are not related or associated with the optical path of the measurement path 298 or reference path and not related to non-linear cyclic errors. Heterodyne signal $s_3$ is transmitted to electronic processor 227 for analysis as electronic signal 223 in either digital or analog format, preferably in digital format. Electronic signal 223 further comprises a Nyquist angular frequency $\omega_{3,Ny}$ determined by the sampling frequency of an analog-to-digital converter used in the conversion of $s_3$ to a digital format.

The phase of driver 205 is transmitted by electrical signal $S_{3,Ref}$, reference signal 221, in either digital or analog format, preferably in digital format, to electronic processor 227. A reference signal, an alternative reference signal to reference signal 221, may also be generated by an optical pick off means and detector (not shown in figures) by splitting off a portion of beam 209 with a non-polarizing beam splitter, mixing the split-off portion of beam 209, and detecting the mixed portion to produce an alternative heterodyne reference signal.

Non-linear cyclic error $\psi_3$ comprises terms generated by the same mechanisms as described for the first embodiment and accordingly will be referred hereinafter as a coherent cyclic error function. A spectral representation of the coherent cyclic error function $\psi_3$, in terms of quantities such as $\phi_3$, $\omega_3$, and $\omega_{3,Ny}$, can be based on different families of orthogonal polynomials and functions. Two examples are a series comprising Fourier sine and cosine functions and a series comprising Chebyshev polynomial functions. Without departing from the spirit and scope of the present invention, the Fourier sine and cosine series spectral representation of $\psi_3$ will be used.

The properties of the spectral representation of $\psi_3$ are described in terms of properties of signal $s_3$. Signal $s_3$ has a form the same as the form of $s_2$ given by Eq. (2) and accordingly is written as $$s_3 = a_{3,1,0,1,0}\cos(\omega_3 t + \varphi_3 + \zeta_{3,1,0,1,0}) + \tag{36}$$

$$\sum_{u,u',p,p^+} a_{3,u,u',p,p^+}\cos(u\omega_3 t + \omega'_{u'} + p\varphi_3 - p^+\varphi_3^+ +$$

$$+ \zeta_{3,u,u',p,p^+}) +$$

$$\sum_q (a_{3,1,0,1,0})^q \begin{Bmatrix} B_{3,1,0,1,0,q,q}\cos\left[q(\omega_3 t+\varphi_3)+\zeta_{3,1,0,1,0,q,q}\right]+ \\ B_{3,1,0,1,0,q,q-2}\cos\left[(q-2)(\omega_3 t+\varphi_3)+\zeta_{3,1,0,1,0,q,q-2}\right]+ \\ \ldots + \\ B_{3,1,0,1,0,q,q_R}\cos\left[q_R(\omega_3 t+\varphi_3)+\zeta_{3,1,0,1,0,q,q_R}\right] \end{Bmatrix}+$$

$\ldots,$ $u=0,1;$ $u'=0,1,\ldots$ except $u'\neq 0$ if $u=1, p=1, p^+=0;\ \omega'_{3,0}=0;$ $p, p^+=0,1,\ldots;\ w_{3,1}/w_{3,2};$ $p^+\neq 0$ if $p=1$ and $u=1;$ $w_{3,1}, w_{3,2}=1,2,\ldots,\ w_{3,1}\neq w_{3,2};$ $q=2,3,\ldots;$ \hfill (36)

where $\phi_3^+ = L_3 p_3 k_3^+ n_3,$ \hfill (37)

$k_3^+ = 2\pi[(1/\lambda_3)+(f_3/c)].$ \hfill (38)

The terms in $\psi_3$ can be obtained fromn Eq. (36) by first writing $s_3$ in the form $$s_3 = A_3(t)\begin{bmatrix}\cos\psi_3\cos(\omega_3 t+\varphi_3+\zeta_3) \\ -\sin\psi_3\sin(\omega_3 t+\varphi_3+\zeta_3)\end{bmatrix},$$ \hfill (39)

using Eqs. (29) and (35), and then using coefficients of $\sin(\omega_3 t+\phi_3+\zeta_3)$ and $\cos(\omega_3 t+\phi_3+\zeta_3)$ terms generated in the writing of $s_3$ in the form given by Eq. (39) to compute $\psi_3$ as the –arc tan of the ratio of the coefficients of $\sin(\omega_3 t+\phi_3+\zeta_3)$ and $\cos(\omega_3 t+\phi_3+\zeta_3)$ terms. Leading terms in Eq. (36) written in the form of Eq. (39) using trigonometric identities are $s_3 =$ \hfill (40)

$\cos(\omega_3 t+\varphi_3+\zeta_3)\times\Bigg\{a_{3,1,0,1,0}\cos(\zeta_{3,1,0,1,0}-\zeta_3)+\sum_{u,u',p,p^+}a_{3,u,u',p,p^+}$ $\cos[(u-1)\omega_3 t+\omega'_{3u'}t+(p-1)\varphi_3-p^+\varphi_3^+ +$ $(\zeta_{3,u,u',p,p^+}-\zeta_3)]+\sum_q (a_{3,1,0,1,0})^q$ $\{B_{3,1,0,1,0,q,q}\cos[(q-1)(\omega_3 t+\varphi_3)+(\zeta_{3,1,0,1,0,q,q}-\zeta_3)]+$ $B_{3,1,0,1,0,q,q-2}\cos[(q-3)(\omega_3 t+\varphi_3)+$ $(\zeta_{3,1,0,1,0,q,q-2}-\zeta_3)]+\ldots +$ $q_R B_{3,1,0,1,0,q,q_R}\cos(\zeta_{3,1,0,1,0,q,q_R}-\zeta_3))\Bigg\}-$ $\sin(\omega_3 t+\varphi_3+\zeta_3)\times\Bigg\{a_{3,1,0,1,0}\cos(\zeta_{3,1,0,1,0}-\zeta_3)+$ $\sum_{u,u',p,p^+}a_{3,u,u',p,p^+}\sin[(u-1)\omega_3 t+\omega'_{3u'}t+(p-1)\varphi_3-$ $p^+\varphi_3^+ +(\zeta_{3,u,u',p,p^+}-\zeta_3)]+\sum_q(a_{3,1,0,1,0})^q$ $\{B_{3,1,0,1,0,q,q}\sin[(q-1)(\omega_3 t+\varphi_3)+(\zeta_{3,1,0,1,0,q,q}-\zeta_3)]+$ -continued $B_{3,1,0,1,0,q,q-2}\sin[(q-3)(\omega_3 t+\varphi_3)+$ $(\zeta_{3,1,0,1,0,q,q-2}-\zeta_3)]+\ldots +$ $q_R B_{3,1,0,1,0,q,q_R}\sin(\zeta_{3,1,0,1,0,q,q_R}-\zeta_3))\Bigg\};$ $u=0,1;$ $u'=0,1,\ldots$ except $u'\neq 0$ if $u=1, p=1, p^+=0;\ \omega'_{3,0}=0;$ $p, p^+=0,1,\ldots;\ w_{3,1}/w_{3,2};$ $p^+\neq 0$ if $p=1$ and $u=1;$ $w_{3,1}, w_{3,2}=1,2,\ldots,\ w_{3,1}\neq w_{3,2};$ $q=2,3,\ldots.$ The terms in the spectral representation of $\psi_3$ are readily identified by noting that $\psi_3$ is equal to –arc tan of the ratio of the coefficients of $\sin(\omega_3 t+\phi_3+\zeta_3)$ and $\cos(\omega_3 t+\phi_3+\zeta_3)$ terms in Eq. (40) and inspection of the properties of the coefficients of $\sin(\omega_3 t+\phi_3+\zeta_3)$ and $\cos(\omega_3 t+\phi_3+\zeta_3)$ terms in Eq. (40).

The coefficients of terms in the spectral representation of $\psi_3$ will in general depend on the rate of change of a phase associated with the term as a result, for example, of properties of group delay experienced by the heterodyne signal.

Referring to FIG. 3c, electronic processor 227 comprises phase detector 250 to process heterodyne signal $s_3$ for phase $\alpha_3$ by either digital or analog signal processes, preferably digital processes, using time-based phase detection such as a digital Hilbert transform phase detector [see section 4.1.1 of "Phase-locked loops: theory, design, and applications" 2nd ed. McGraw-Hill (New York) 1993, by R. E. Best], zero crossing phase detectors, or the like. Electronic processor 227 further comprises spectrum analyzers 251A and 251B that process reference signal $s_{3,Ref}$ and heterodyne signal $s_3$, respectively, for $\omega_3$ and $\alpha_3$, respectively. Angular frequency $\dot{\alpha}_3$ is the angular frequency of the dominant peak in the power spectrum of $s_3$. Spectrum analyzers 251A and 251B are preferably based on a sliding window Fourier transform algorithm. Phase $\alpha_3$ and angular frequency $\omega_3$ are transmitted to electronic processor 252 where $\omega_3=\dot{\alpha}_3-\omega_3 t$ and the Fourier transform of $\alpha_3$, $F(\alpha_3)$, are computed.

In a next step in electronic processor 227, Fourier transform $F(\alpha_3)$ and angular frequencies $\dot{\alpha}_3$, $\omega_3$, and $\omega_{3,Ny}$ are transmitted to electronic processor 253 where the complex spectral coefficients of coherent cyclic error terms in $\psi_3$ are extracted at angular frequencies $\omega_{3,\nu}$ and aliases, $\omega_{3,\nu,A}$, of $\omega_{3,\nu}$. An amplitude of a cyclic error term in $\alpha_3$ corresponds to the amplitude of a corresponding peak in an associated power spectrum and the phase of the cyclic error term in $\alpha_3$ corresponds to the arctan of the ratio of the imaginary and real components of $F(\alpha_3)$ at the angular frequency of the corresponding peak in the associated power spectrum.

Angular frequencies $\omega_{3,v}$, where $v$ is an index parameter comprising u, u', p, p$^+$, and q, correspond to the set of angular frequencies equal to derivatives, with respect to time, of the arguments of the sinusoidal factors of terms in the spectral representation of $\psi_3$. Aliases $\omega_{3,v_A}$ are given by the formula $$\tilde{\omega}_{3,v,A} = (-1)^r \tilde{\omega}_{3,v} - \left[(-1)^r \left(r + \frac{1}{2}\right) - \left(\frac{1}{2}\right)\right]\omega_{3,Ny}, r = 1, 2, \ldots, \quad (41)$$

with $$r\omega_{3,Ny} < \omega_{3,v} < (r+1)\omega_{3,Ny}. \quad (42)$$

In practice, the amplitudes and associated phases of cyclic error terms in $\psi_3$ need be extracted only for a small subset of the set of possible $\omega_{3,v}$ and $\omega_{3,v_A}$. The selection of the subset of the set of possible $\omega_{3,v}$ and $\omega_{3,v_A}$ may be guided by properties of certain coefficients of $\sin(\omega_3 t + \phi_3 + \zeta_3)$ and $\cos(\omega_3 t + \phi_3 + \zeta_3)$ terms in Eq. (40). However, as part of an initialization procedure, the selection of the subset of the set of possible $\omega_{3,v}$ and $\omega_{3,v_A}$ is based on a power spectrum analysis of $\alpha_3$ and chi-square tests of peaks in the power spectrum. The chi-square tests identify statistically significant peaks in the power spectrum. Representation of the angular frequencies $\omega_{3,v}$ and $\omega_{3,v_A}$ of the subset of $\omega_{3,v}$ and $\omega_{3,v_A}$ associated with the statistically significant peaks in terms of $\omega_3$, $\omega_{3,Ny}$, $\dot\phi_3$, $\dot\phi_3^+$, u, u', p, p$^+$, q, $w_{3,1}/w_{3,2}$, and r is determined by observing properties of the respective $\omega_{3,v}$ and $\omega_{3,Ny}$ as $\dot\phi_3$ is varied. Note that $\dot\phi_3^+ = \dot\phi_3$ to a relative precision of the order of or less than $10^{-6}$.

The initialization procedure is performed by electronic processor 253. As part of an operating procedure of the second embodiment, power spectrum analyses of $\alpha_3$ and chi-square tests of peaks in the power spectra are monitored for possible changes that may need be made to the subset of the set of possible $\omega_{3,v}$ and $\omega_{3,v_A}$ during operation of the apparatus and method of the second embodiment. The power spectrum analyses of $\alpha_3$ and associated chi-square tests executed as part of the monitoring procedure are also performed as a background task by electronic processor 253.

The extracted complex spectral coefficients in $F(\alpha_3)$ corresponding to cyclic error terms in $\psi_3$ are then sent to electronic processor 254 where the extracted spectral coefficients are normalized, filtered with respect to time, and interpolations made as required and a multidimensional array of normalized, filtered, and interpolated complex spectral coefficients maintained. The step of normalization is for the purpose of compensating for effects of non-zero values of second and higher order derivatives of $\phi_2$ with respect to time that exist at the time of a determination of set of complex spectral coefficients. The dimensionality of the multidimensional array is determined in part by the magnitude of the filtered complex spectral coefficients, the required precision of an end use application with respect to correction for coherent cyclic errors, and the dependence of the filtered complex spectral coefficients on $\dot\phi_2$ and other system properties.

Figure 3B:
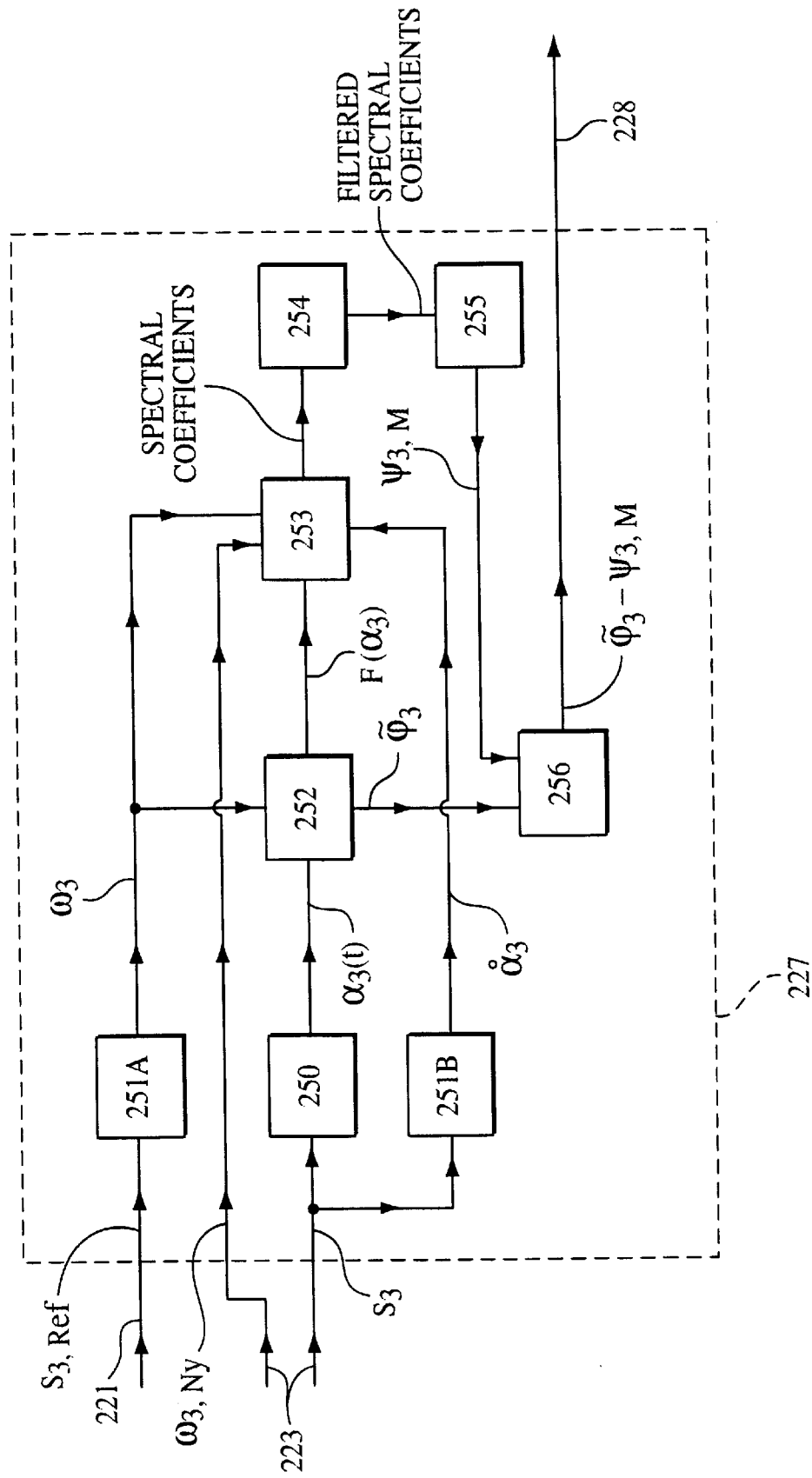
Figure 3C:
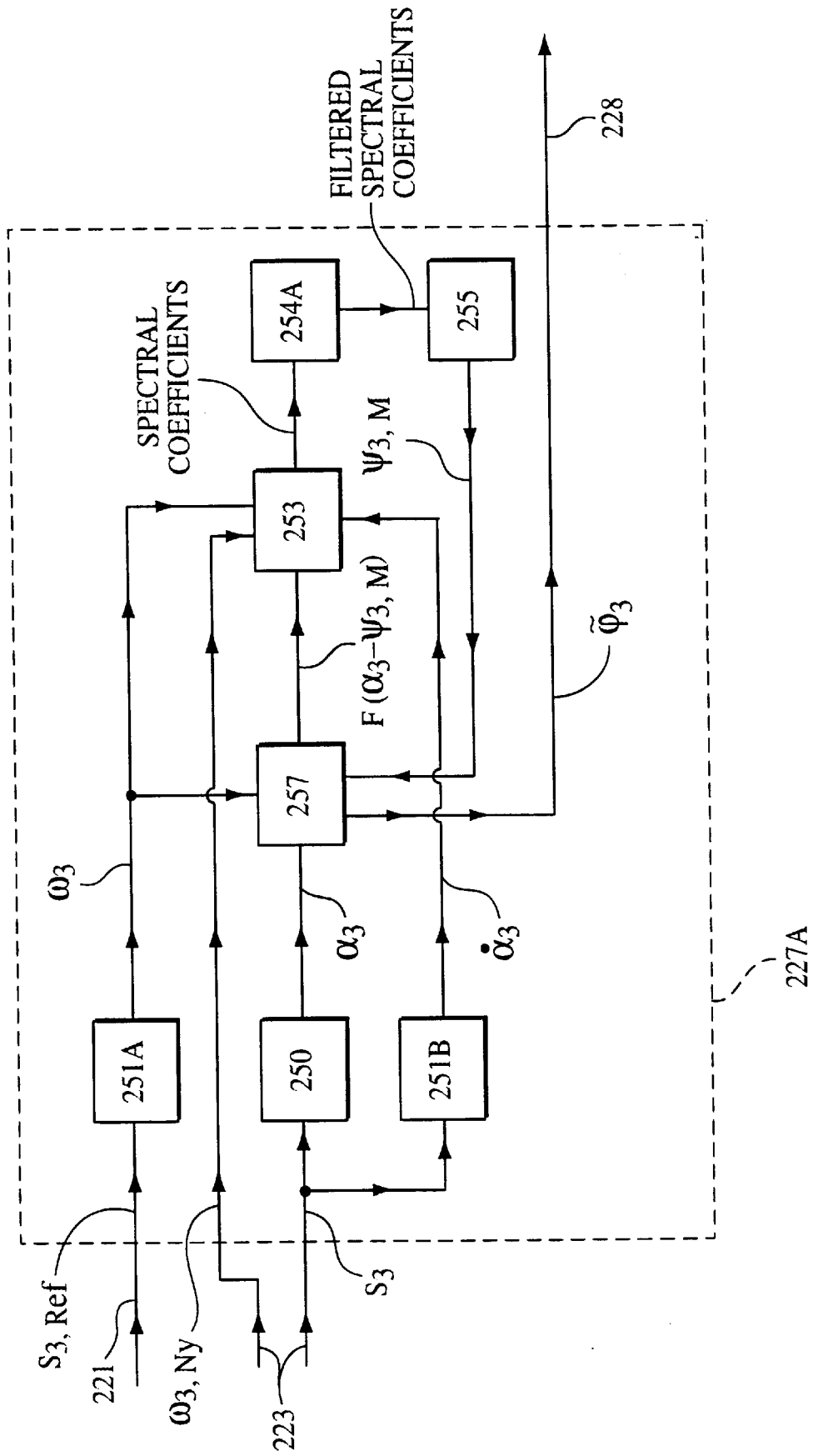

Electronic procession 255, in the next step in electronic processor 227 as shown in FIG. 3b, computes the coherent cyclic error correction $\psi_{3,M}$ using information listed in the multidimensional array of normalized, filtered, and interpolated spectral coefficients generated by electronic processor 254. Electronic processor 256 (see FIG. 3b) computes $\phi_3$ wherein the coherent cyclic errors have been compensated by subtracting $\psi_{3,M}$ from $\phi_3$. Phase $\phi_3$ is transmitted by electronic processor 227 as signal 228 to computer 229 for use in downstream applications.

Each of the electronic processors comprising electronic processor 227 preferably performs respective functions as digital processes. The Fourier transform of $\alpha_3$ comprises Fourier transforms of $(\phi_3 + \omega_3 t)$ and terms having factors such as $\cos[(u-1)\omega_3 t + \omega'_{3u'} + (p-1)\phi_3 - p^+\phi_3^+]$ and $\sin[(u-1)\omega_3 t + \omega'_{3u'} + (p-1)\phi_3 - p^+\phi_3^+]$ as evident for inspection of Eq. (40). The Fourier transform of $(\phi_3 + \omega_3 t)$ over time interval $T - \tau/2$ to $T + \tau/2$, with $\phi_3$ represented as a Taylor's series about $t = T$, may be expressed as $$F(\varphi_3 + \omega_3 t) = \quad (43)$$

$$\frac{\tau}{\sqrt{2\pi}} e^{i\omega T}[\varphi_3(T) + \omega_3 T]j_0\left(\frac{\omega\tau}{2}\right) + \frac{\tau}{\sqrt{2\pi}} e^{i\omega T}\left\{g_1\left(\frac{\omega\tau}{2}\right)\left(\frac{\tau}{2}\right)\dot\varphi_3(T) + \right.$$

$$g_2\left(\frac{\omega\tau}{2}\right)\left(\frac{1}{2!}\right)\left(\frac{\tau}{2}\right)^2 \ddot\varphi_3(T) + g_3\left(\frac{\omega\tau}{2}\right)\left(\frac{1}{3!}\right)\left(\frac{\tau}{2}\right)^3 \dddot\varphi_3(T) +$$

$$\left. g_4\left(\frac{\omega\tau}{2}\right)\left(\frac{1}{4!}\right)\left(\frac{\tau}{2}\right)^4 \varphi_3^{IV}(T) + g_5\left(\frac{\omega t}{2}\right)\left(\frac{1}{5!}\right)\left(\frac{\tau}{2}\right)^5 \varphi_3^V(T) + \ldots\right\}.$$

It is evident from inspection of Eq. (40) that, in the second embodiment, there will be present zero frequency shift coherent cyclic errors arising from terms having coefficients with factors $B_{3,1,0,1,0,q,qR}$, $q = 3, 5, \ldots$. The zero frequency shift coherent cyclic errors arise from the same type terms as the zero frequency shift coherent cyclic errors present in the first embodiment.

A second embodiment procedure used for detecting and isolating the primary zero frequency shift coherent cyclic errors is based on the same technique as the procedure described for detecting and isolating the primary zero frequency shift coherent cyclic errors for the first embodiment. A second beam 209T (not shown in FIG. 3a) is introduced and used to generate a multiplet in a power spectrum of phase $\alpha_3$ centered at a frequency equal to one half the frequency spacing of contiguous members of the multiplet. The description of beam 209T is the same as the corresponding portion of the description given for beam 109T of the first embodiment. Measured properties with respect to amplitudes and phases of members of the multiplet are processed by electronic processor 227 to determine for the second embodiment the primary zero frequency shift coherent cyclic errors following the same procedure as described for corresponding portions of the description given for the first embodiment.

The remaining description of the second embodiment is the same as corresponding portions of the description given for the first embodiment.

FIG. 3c depicts in schematic form, in accordance with the preferred apparatus and method of a variant of the second embodiment, electronic processor 227A. The variant of the second embodiment is from the second category of embodiments and comprises beam 209, source of beam 209, interferometer 269, detector system 289, and digital computer 229 of the second embodiment shown in FIG. 3a and electronic processor 227A shown in FIG. 3c.

Electronic processor 227A comprises certain elements that perform like functions as like numbered elements of electronic processor 227 of the second embodiment. In the operation of electronic processor 227A, as shown in FIG. 3c, phase $\alpha_3$, computed coherent cyclic error $\psi_{3,M}$, and angular frequency $\omega_3$ are transmitted to electronic processor 257 where $\phi_3$, $(\alpha_3 - \psi_{3,M})$, and the Fourier transform of $(\alpha_3 - \psi_{3,M})$, $F(\alpha_3 - \psi_{3,M})$, are generated. Fourier transform $F(\alpha_3 - \psi_{3,M})$ is transmitted to electronic processor 253 of 227A along with angular frequencies $\alpha_3$ from electronic processor 251B and $\omega_{3,Ny}$. Phase $\phi_3$ is transmitted by electronic processor 227A as electronic signal 228 to digital computer 229.

Non-zero spectral coefficients in $F(\alpha_3-\psi_{3,M})$ represent incomplete compensation for coherent cyclic errors in $\phi_3$. Incomplete compensation for coherent cyclic errors in $\phi_3$ can be a result for example of changes of coherent cyclic errors in time and/or the result of statistical errors in measured quantities. Incomplete compensation will generally be present during an initialization procedure for establishing a multidimensional array of normalized, filtered, and interpolated spectral coefficients by electronic processor 254A. Electronic processor 253 of 227A determines spectral coefficients from $F(\alpha_3-\psi_{3,M})$ and the spectral coefficients are transmitted to electronic processor 254A. Electronic processor 254A processes the spectral coefficients representing incomplete compensation of coherent cyclic errors in $\phi_3$ and updates the multidimensional array of filtered coherent cyclic error coefficients. Electronic processor 254A further processes the multidimensional array of filtered coherent cyclic error coefficients the same as electronic processor 254 of processor 227 of the second embodiment with respect to required corrections for non-zero second and higher order derivatives of $\phi_3$ and the identification and omission of spectral coefficients corresponding to superimposed values, with respect to frequency, of respective coherent cyclic errors.

The remaining description of the variant of the second embodiment is the same as corresponding portions of the description given for the second embodiment.

Figure 4A:
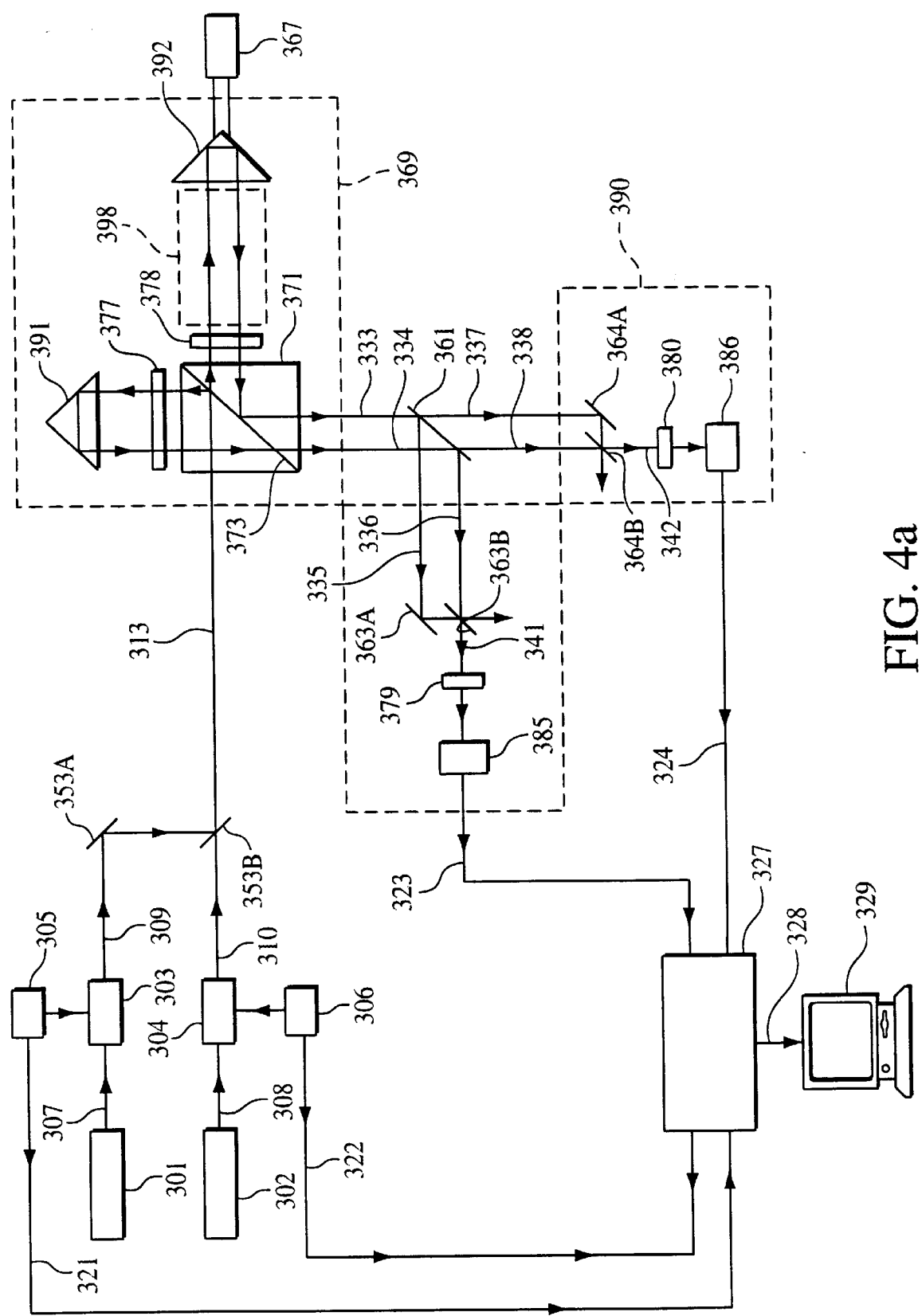
FIG. 4a is schematic diagrams of a third embodiment of an interferometry system that quantifies nonlinearities.
Figure 4B:
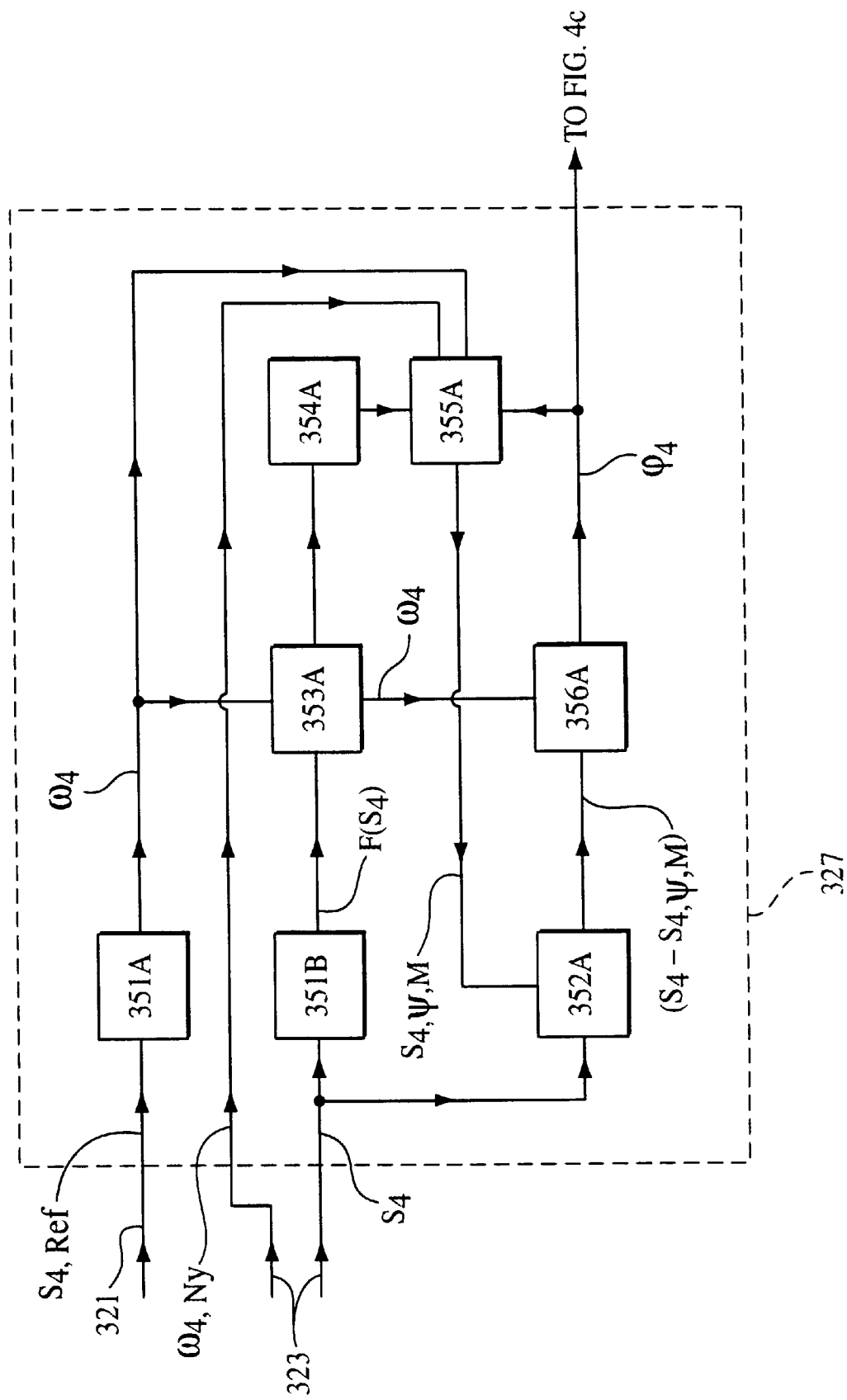
Figure 4C:
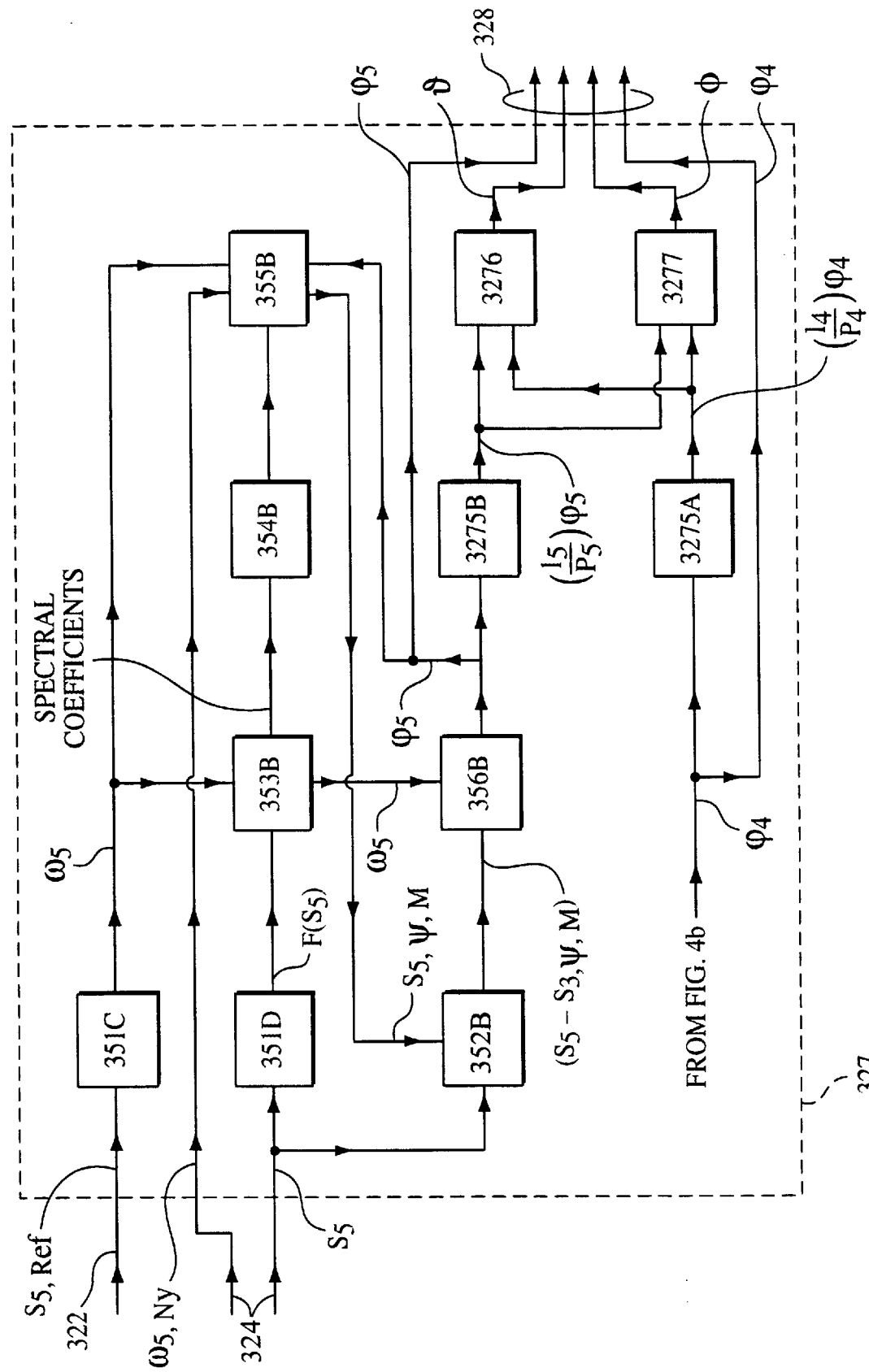

FIGS. 4a, 4b, and 4c depict in schematic form in accordance with the preferred apparatus and method of the third embodiment of the present invention. The third embodiment is from the third category of the several different categories of embodiments. Certain embodiments of the third category of embodiments comprise apparatus and methods for measuring and correcting for cyclic errors in optical dispersion related signals such as used to measure and correct for effects of a gas in a measuring path of a distance measuring interferometer. Certain other embodiments of the third category of embodiments comprise apparatus and methods for measuring and correcting for cyclic errors in both a dispersion related signal and a signal used for determination of changes in optical path length of a measurement path in a distance measuring interferometer. The effects of cyclic errors in corrections for effects of a gas in a measuring path are greater than the effects of cyclic errors in the signal used for determination of changes in optical path length by one and a half or more orders of magnitude.

The third embodiment comprises apparatus and method for measuring and monitoring the dispersion of a gas in a measurement path of a distance measuring interferometer and correcting for effects of the gas in the measurement path of the distance measuring interferometer. The third embodiment further comprises apparatus and method for measuring and correcting for effects of cyclic errors in both an optical dispersion related signal such as used to measure the dispersion of a gas and a signal used for determination of changes in an optical path length of a measurement path in the distance measuring interferometer. The refractive index of the gas and/or the physical length of the measurement path may be changing. In addition, the ratio of wavelengths of light beams generated by adopted light sources is matched with a certain relative precision to a known ratio value comprised of non-zero quantities. The non-zero quantities may comprise one or more low order non-zero integers.

Referring to FIG. 4a and in accordance with the preferred apparatus and method of the third embodiment, the description of light beam 309 and the source of light beam 309 is the same as corresponding portions of the descriptions given for light beam 109 and the source of light beam 109 of the first embodiment. The wavelength of source 301 is $\lambda_4$. In a next step, a light beam 308 emitted from a source 302 passes through a modulator 304 becoming light beam 310. Modulator 304 is excited by an electronic driver 306 similar to the excitation of modulator 303 by electronic driver 305, respectively. Source 302, similar to source 301, is preferably a laser or like source of polarized, coherent radiation, but preferably at a different wavelength, $\lambda_5$.

The ratio of the wavelengths $\lambda_4/\lambda_5$ has a known approximate ratio value $l_4/l_5$, i.e.

$$(\lambda_4/\lambda_5) \cong (l_4/l_5), \tag{44}$$

where $l_4$ and $l_5$ comprise non-zero quantities. The non-zero quantities may comprise one or more low order non-zero integer values. Components of beams 309 and 310 with oscillation frequencies shifted by amounts $f_4$ and $f_5$, respectively, with respect to non-frequency shifted components of beams 309 and 310, respectively, are polarized orthogonally to the plane of 4a. Oscillation frequencies $f_4$ and $f_5$ are determined by electronic drivers 305 and 306, respectively. In addition, the directions of the frequency shifts of the frequency shifted components of beams 309 and 310 are the same.

It will be appreciated by those skilled in the art that beams 307 and 308 may be provided alternatively be a single laser source emitting more than one wavelength, by a single laser source combined with optical frequency doubling means to achieve frequency doubling, a laser source with a non-linear element internal to the laser cavity, etc., two laser sources of differing wavelengths combined with sum-frequency generation or difference-frequency generation, or any equivalent source configuration capable of generating light beams of two or more wavelengths. It will also be appreciated by those skilled in the art that one or both of the frequency shifts $f_4$ and $f_5$ may be the result of Zeeman splitting, birefringent elements internal to a laser cavity, or like phenomena characteristic of the laser sources themselves. The generation of beams by a single laser with two widely separated wavelengths and for each beam, a pair of orthogonally polarized components, one component of each pair frequency shifted with respect to the second component of the corresponding pair, is described in U.S. Pat. No. 5,732,095 entitled "Dual Harmonic-Wavelength Split-Frequency Laser" and issued March 1998 to P. Zorabedian.

It will be further appreciated by those skilled in the art that both polarization components of beam 309 and/or of beam 310 may be frequency shifted without departing from the scope and spirit of the invention, $f_4$ remaining the difference in frequencies of the polarization components of beam 309 and $f_5$ remaining the difference in frequencies of the polarization components of beam 310. Improved isolation of an interferometer and a laser source is generally possible by frequency shifting both polarization components of a beam, the degree of improved isolation depending on the means used for generating the frequency shifts.

In a next step, beam 309 is reflected by mirror 353A and a portion thereof reflected by dichroic non-polarizing beamsplitter 353B to become a first component of beam 313, the $\lambda_4$ component. A portion of beam 310 is transmitted by dichroic non-polarizing beamsplitter 353B to become a second component of beam 313, the $\lambda_5$ component, wherein the propagation of the $\lambda_5$ component is preferably parallel and coextensive with the propagation of the $\lambda_4$ component. In a further step, beam 313 propagates to an interferometer 369 comprised of optical means for introducing a phase shift $\phi_4$ between the non-frequency shifted and frequency shifted components of the $\lambda_4$ component of beam 313 and a phase shift $\phi_5$ between the non-frequency shifted and frequency shifted components of the $\lambda_5$ component of beam 313. Magnitudes of phase shifts $\phi_4$ and $\phi_5$ are related to round-trip physical lengths $L_4$ and $L_5$ of measurement path 398 according to the formulae $$\phi_m = L_m p_m k_m n_m, \qquad (45)$$

m=4 and 5, where $p_m$ is the number of passes through the respective reference and measurement legs for a multiple pass interferometer and $n_m$ is the refractive index of a gas in measurement path 398 corresponding to wavenumbers $k_m = (2\pi)/\lambda_m$.

As shown in FIG. 4a, interferometer 369 comprises a reference retroreflector 391, object retroreflector 392 with a position controlled by translator 367, quarter-wave phase retardation plates 377 and 378, and a polarizing beam splitter 373. Quarter-wave phase retardation plates 377 and 378 and polarizing beam splitter 373 exhibit respective properties at both $\lambda_4$ and $\lambda_5$. This configuration is known in the art as a polarized Michelson interferometer and is shown as a simple illustration with $p_4 = p_5 = 1$.

The number-of-passes parameters $p_4$ and $p_5$ may have values that are the same or values that are different one with respect to other.

Eqs. (45) are valid for the case where the paths in an interferometer for beams with one wavelength and the paths in the interferometer for beams with the second wavelength are substantially coextensive, a case chosen to illustrate in the simplest manner the function of the invention in the third embodiment. To those skilled in the art, the generalization to the case where the respective paths for beams with the two different wavelengths are not substantially coextensive is a straight-forward procedure.

After passing through interferometer 369, the portion of beam 313 passing through the measurement path 398 becomes a phase-shifted beam 333 and the portion of beam 313 passing through the reference path containing retroreflector 391 becomes phase-shifted beam 334. Phase-shifted beams 333 and 334 are polarized orthogonal to the plane and in the plane of FIG. 4a, respectively. A conventional dichroic beam splitter 361 separates those portions of beam 333 corresponding to wavelengths $\lambda_4$ and $\lambda_5$ into beams 335 and 337, respectively, and those portions of beam 334 corresponding to wavelengths $\lambda_4$ and $\lambda_5$ into beams 336 and 338, respectively. Beams 335 and 336 enter detector system 389 and beams 337 and 338 enter detector system 390.

In detector system 389 as shown in FIG. 4a, beam 335 is first reflected by mirror 363A and then reflected by polarizing beam splitter 363B to form a first component of beam 341. Beam 336 is transmitted by polarizing beam splitter 363B to become a second component of beam 341. In detector system 390, beam 337 is first reflected by mirror 364A and then reflected by polarizing beam splitter 364B to form a first component of beam 342. Beam 338 is transmitted by polarizing beam splitter 364B to become a second component of beam 342. Beams 341 and 342 pass through polarizers 379 and 380, respectively, impinge upon photodetectors 385 and 386, respectively, and generate preferably by photoelectric detection two electrical interference signals. The two electrical interference signals comprise two heterodyne signals $s_4$ and $s_5$, respectively. Polarizers 379 and 380 are preferably oriented so as to mix polarization components of beams 341 and 342, respectively. The heterodyne signals $s_4$ and $s_5$ correspond to wavelengths $\lambda_4$ and $\lambda_5$, respectively.

Signals $s_4$ and $s_5$ have the forms $$\begin{aligned}
s_m = &\, a_{m,1,0,1,0} \cos(\omega_m t + \varphi_m + \zeta_{m,1,0,1,0}) + \\
&\sum_{u,u',p,p^+} a_{m,u,u',p,p^+} \cos(u\omega_m t + \omega'_{mu'} t + p\varphi_m - p^+\varphi_m^+ + \zeta_{m,p,p^+,u}) + \\
&\sum_q (a_{m,1,0,1,0})^q \{B_{m,1,0,1,0,q,q} \cos[q(\omega_m t + \varphi_m) + \zeta_{m,1,0,1,0,q,q}] + \\
&\quad B_{m,1,0,1,0,q,q-2} \cos[(q-2)(\omega_m t + \varphi_m) + \zeta_{m,1,0,1,0,q,q-2}] + \\
&\quad \ldots + B_{m,1,0,1,0,q,q_R} \cos[q_R(\omega_m t + \varphi_m) + \zeta_{m,1,0,1,0,q,q_R}] \} + \ldots;
\end{aligned}$$

$u=0,1;$ $u'=0,1,\ldots$ except $u'\neq 0$ if $u=1;\ p=1,\ p^+=0;\ \omega'_{4,0}=0;$ $p, p^+ = 0, 1, \ldots;\ w_{wm,1}/w_{m,2};$ $p^+ \neq 0$ if $p=1$ and $u=1;$ $w_{m,1} w_{m,2} = 1, 2, \ldots;\ w_{m,1} w_{m,2};$ $q = 2, 3, \ldots;$ $m = 4, 5;$ (46)

where $$\phi_m^+ = L_m p_m k_m^+ n_m, \qquad (47)$$

$$k_m^+ = 2\pi[(1/\lambda_m) + (\zeta_m/c)]. \qquad (48)$$

Descriptions of $s_4$ and $s_5$ representations given by Eqs. (46) are the same as corresponding portions of the description given of the $s_2$ representation of the first embodiment by Eq. (2). Heterodyne signals $s_4$ and $s_5$ are transmitted to electronic processor 327 for analysis as electronic signals 323 and 324, respectively, in either digital or analog format, preferably in digital format.

Referring now to FIG. 4b, phase $\phi_4$ is determined by certain elements of electronic processor 327 wherein the certain elements comprise electronic processors 351A, 351B, 352A, 353A, 354A, 355A, and 356A that perform like functions as elements 151A, 151B, 152, 153, 154, 155, and 156, respectively, of the first embodiment. Phase $\phi_5$ is determined by certain other elements of electronic processor 327 wherein the certain other elements comprise electronic processors 351C, 351D, 352B, 353B, 354B, 355B, and 356B (see FIG. 4c) that perform like functions as elements 151A, 151B, 152, 153, 154, 155, and 156, respectively, of the first embodiment.

The phases of electronic drivers 305 and 306 are transmitted by electrical signals, reference signals 321 and 322, respectively, in either digital or analog format, preferably in digital format, to electronic processor 327. Electronic processors 351A and 351C process reference signals $s_{4,Ref}$ and $s_{5,Ref}$, respectively, to determine angular frequencies $\omega_4 = 2\pi f_4$ and $\omega_5 = 2\pi f_5$, respectively, preferably by a sliding window FFT frequency detection algorithm.

Reference signals, alternatives to reference signals 321 and 322, may also be generated by an optical pick off means and detectors (not shown in figures) by splitting off portions of beams 309 and 310 with beam splitters, preferably non-polarizing beam splitters, mixing the respective split-off portions of beam 309 and beam 310, and detecting the mixed portions to produce alternative heterodyne reference signals.

Referring again to FIG. 4c, phases $\phi_4$ and $\phi_5$ are next multiplied by $l_4/p_4$ and $l_5/p_5$, respectively, in electronic processors 3275A and 3275B, respectively, preferably by digital processing, to produce phases $(l_4/p_4)\phi_4$ and $(l_5/p_5)\phi_5$, respectively. Phases $(l_4/p_4)\phi_4$ and $(l_5/p_5)\phi_5$ are next added together in electronic processor 3276 and subtracted one from the other in electronic processor 3277, preferably by digital processes, to create the phases $\theta$ and $\Phi$, respectively. Formally, $$\vartheta = \left(\frac{l_5}{p_5}\varphi_5 + \frac{l_4}{p_4}\varphi_4\right), \quad (49)$$

$$\Phi = \left(\frac{l_5}{p_5}\varphi_5 - \frac{l_4}{p_4}\varphi_4\right). \quad (50)$$

Phases $\theta$ and $\Phi$ can also be written, using the definitions given by Eqs. (45), (49), and (50) as $$\vartheta = \{\overline{L}[\chi(n_5+n_4) + K(n_5-n_4)] + \Delta L[\chi(n_5-n_4) + K(n_5+n_4)] + \xi_\zeta\}, \quad (51)$$

$$\Phi = \{\overline{L}[\chi(n_5-n_4) + K(n_5+n_4)] + \Delta L[\chi(n_5+n_4) + K(n_5-n_4)] + Z_\zeta\}, \quad (52)$$

where $$\chi = (l_5k_5 + l_4k_4)/2, \quad (53)$$

$$K = (l_5k_5 - l_4k_4)/2, \quad (54)$$

$$\overline{L} = (L_5+L_4)/2, \quad (55)$$

$$\Delta L = (L_5-L_4)/2, \quad (56)$$

$$\xi_\zeta = \left(\frac{l_5}{p_5}\zeta_{5,1,0,1,0} + \frac{l_4}{p_4}\zeta_{4,1,0,1,0}\right), \quad (57)$$

$$Z_\zeta = \left(\frac{l_5}{p_5}\zeta_{5,1,0,1,0} - \frac{l_4}{p_4}\zeta_{4,1,0,1,0}\right). \quad (58)$$

The preferred nominal value for $\Delta L$ is zero and for coextensive beam components at wavelengths $\lambda_4$ and $\lambda_5$, $\Delta L \ll \lambda_4$ or $\lambda_5$.

Dispersion $(n_5-n_4)$ of the gas corrected for effects of cyclic errors in dispersion related signals can be determined from $\theta$ and $\Phi$ using the formula $$(n_5-n_4) = \frac{1}{\chi\overline{L}[1-(K/\chi)^2]}[\Phi - \vartheta(K/\chi) - Q_\zeta] - \left(\frac{\Delta L}{\overline{L}}\right)\left(\frac{1}{n_5+n_4}\right), \quad (59)$$

where $$Q_\zeta = Z_\zeta - (K/\chi)\xi_\zeta. \quad (60)$$

For those applications related to distance measuring interferometry, heterodyne phase $\phi_4$ and phases $\theta$ and $\Phi$ may be used to determine distance $L_4$ as a quantity independent of the effects of the refractive index of the gas in the measuring path of the distance measuring interferometer and corrected for the effects of cyclic errors in both the dispersion related signals and optical path length related signals using the formula $$L_4 = \frac{1}{(\chi - K)} \quad (61)$$

$$\left\{\frac{l_4}{p_4}(\varphi_4 - \zeta_4) - [1-(\Delta L/\overline{L})]\frac{\Gamma}{[1+(K/\chi)]}[\Phi - (K/\chi)\vartheta - Q_\zeta]\right\} +$$

$$\Gamma\frac{1}{(n_5+n_4)}\Delta L[1-(\Delta L/\overline{L})]$$

where $\Gamma$, the reciprocal dispersive power of the gas, is defined as $$\Gamma = \frac{(n_4-1)}{(n_5-n_4)}. \quad (62)$$

It is evident from the definition of K given by Eq. (54) that $(K/\chi)=0$ corresponds to wavelengths $\lambda_4$ and $\lambda_5$ being strictly harmonically related. For an application where $|K/\chi|>0$ and the value of $(K/\chi)$ must be known to a certain precision in the use of Eqs. (59) and/or (61) to meet an end use requirement, $(K/\chi)$ is measured by wavelength monitors. The wavelength monitors may comprise interferometers with or without vacuum cells and/or frequency doubling of light beams by SHG. For an application where the value of $\chi$ must be known to another certain precision in the use of Eqs. (59) and/or (61), $\chi$ is measured by a wavelength monitor. In addition, when values for $\chi$ and $(K/\chi)$ are both required, they may both be obtained from the same apparatus.

A value for the reciprocal dispersive power $\Gamma$ can be obtained to a certain relative precision from known refractive properties of known constituents of a gas in the measuring path. For those applications where the gas composition is not known to a requisite accuracy and/or the refractive properties of the gas constituents is not known to a corresponding requisite accuracy, $\Gamma$ can be measured by apparatus such as described in copending commonly owned U.S. application Ser. No. 09/232,515 filed Jan. 19, 1999 entitled "Apparatus And Methods For Measuring Intrinsic Optical Properties Of A Gas" by Henry A. Hill, the foregoing application being incorporated herein by reference.

The relative precision to which the dispersion $(n_5-n_4)$ can be determined, if cyclic error effects are not compensated, is limited in part by the effect of cyclic errors. The correction for cyclic error effects that has been made in obtaining the $[\Phi-\theta(K/\chi)-Q_\zeta]$ factor in Eqs. (59) and (61) is $Q_\psi$, given by the formula $$Q_\psi 32 Z_\psi - (K/\chi)\xi_{104} \quad (63)$$

where $$\xi_\psi = \left(\frac{l_5}{p_5}\psi_5 + \frac{l_4}{p_4}\psi_4\right), \quad (64)$$

$$Z_\psi = \left(\frac{l_5}{p_5}\psi_5 - \frac{l_4}{p_4}\psi_4\right). \quad (65)$$

The correction $Q_{104}$ enters as a term in a factor $[\Phi-\theta(K/\chi)-Q_\psi-Q_\zeta]$ where $\Phi$ and $\theta$ are the corresponding values of $\Phi$ and $\theta$, respectively, uncompensated for effects of cyclic errors. Thus the magnitude of the cyclic error effects in determined values of the dispersion $(n_5-n_4)$, according to Eqs. (59) and (63), is of the order of $$\left[\left(\frac{l_m}{p_m}\right)|\psi_m|\right] \Big/ \overline{L}\chi(n_5 - n_4), \quad m = 4 \text{ and } 5. \quad (66)$$

Consider for example, an application where $\lambda_4=0.633$ $\mu$m, $\lambda_4=2\lambda_5$, $p_4=p_5=1$, $\overline{L}=0.5$ m, and the gas is comprised of air at 25° C. and a pressure of one atmosphere. For the example conditions, the magnitude of the contribution of $\psi_4$ to the relative precision as expressed by Eq. (66) is $$\approx 0.019|\psi_4, \quad (67)$$

$\psi_4$ being expressed in radians and $|\psi_4|$ indicating the absolute value of $\psi_4$. Continuing with the example, for a specific cyclic error of $|\psi_4|=0.1$ radians, a cyclic error in phase corresponding in the example to a cyclic error in a distance measurement of 5 nm, the specific cyclic error limits the relative precision to which the dispersion $(n_5-n_4)$ can be measured to $\approx 0.2\%$. If a source for the $\lambda_4$ beam is a NbYAG laser with $\lambda_4=1.06$ $\mu$m, the corresponding limits on the relative precision to which the dispersion $(n_5-n_4)$ can be measured is $\approx 0.6\%$.

The limitations of effects of cyclic errors on the relative precision to which the dispersion $(n_5-n_4)$ can be determined, if cyclic error effects are not compensated, propagate directly to limitations of effects of cyclic errors on relative precision to which refractivity effects of gas in a measurement path of a distance measuring interferometer can be determined using dispersion interferometry. From inspection of Eq. (61), it is evident that the magnitude of the cyclic error contribution of $\psi_m$ entering through $Q_\psi$ is $\cong \Gamma|\psi_m|$ relative to the magnitude of the cyclic error contribution $|\psi_4|$ entering through the $\phi_4=(\phi_4-\psi_4-\zeta_4)$ term. For the two cases of $\lambda_4=0.633$ $\mu$m with $\lambda_4=2\lambda_5$ and $\lambda_4=1.06$ $\mu$m also with $\lambda_4=2\lambda_5$, the values for $\Gamma$ are 22 and 75, respectively. Thus the effects of cyclic error contributions to the correction term in Eq. (61) for the refractivity of a gas in a measuring path must be reduced by approximately one and a half or more orders of magnitude if the effects of the cyclic error contributions resulting from the correction term are to be of the order of or less than the effects of the cyclic error contributions resulting directly from the $\phi_4=(\phi_4-\psi_4-\zeta_4)$ term.

The remaining description of the third embodiment is the same as corresponding portions of the description given for the first embodiment.

The distance $L_5$ can also be determined in a first variant of the third embodiment using $\phi_5$ instead of $\phi_4$. The corresponding equation for the determination of $L_5$ is $$L_5 = \frac{1}{(\chi + K)} \left\{ \begin{array}{l} \frac{l_5}{p_5}(\varphi - \zeta_5) - \\ [1 - (\Delta L/\overline{L})]\frac{(\Gamma + 1)}{[1 - (K/\chi)]}[\Phi - (K/\chi)\vartheta - Q_\zeta] \end{array} \right\} + \quad (68)$$

$$\frac{(\Gamma + 1)}{(n_5 + n_4)}\Delta L[1 - (\Delta L/\overline{L})].$$

The remaining description of the first variant of the third embodiment is the same as corresponding portions of the description given for the third embodiment.

It will be evident to those skilled in the art that the quantities $L_4$ and $L_5$ of the third embodiment and of the first variant of the third embodiment, respectively, can both be determined and used to obtain reduced statistical error in a determination of a change in a physical path length without departing from either the scope or spirit of the present invention.

It will also be evident to those skilled in the art that $L_5$ could be the distance determined by the third embodiment instead of $L_4$ without departing from either the scope or spirit of the present invention.

It will be further evident to those skilled in the art that for those end use applications where $K/\chi$ must be known to a certain precision and/or $\chi$ must be known to another certain precision, effects of cyclic errors in measured wavelength and wavelength ratio values obtained by wavelength measuring and monitoring apparatus can be measured and compensated by application of the apparatus and method of the first and second embodiments and variants thereof and wavelength monitors such as subsequently described herein in a sixth embodiment and variants thereof of the present invention without departing from the scope and spirit of the present invention.

For those end use applications where $\Gamma$ is measured for the gas in the measuring path 398, it may further be necessary to measure and compensate for effects of cyclic errors. The subsequently described herein in the sixth embodiment and variants thereof may be used in obtaining measured values of $\Gamma$ compensated for effects of cyclic errors.

A second variant of the third embodiment is described. In the third embodiment, the effects of cyclic errors are compensated by using corresponding methods and apparatus of the first embodiment. In the second variant of the third embodiment, the effects of cyclic errors are compensated by using the corresponding methods and apparatus of the variant of the first embodiment. The remaining description of the second variant of the third embodiment is the same as corresponding portions of descriptions given for the first and third embodiments and variants thereof.

The fourth embodiment of the present invention is described, in accordance with the preferred apparatus and method of the fourth embodiment, which comprises apparatus and method for measuring and monitoring the dispersion of a gas in a measurement path and the change in the optical path length of the measurement path due to the gas. The fourth embodiment further comprises apparatus and method for compensating for effects of cyclic errors on a measured dispersion of the gas and on measured changes in the optical path length of the measurement path due to the gas. The fourth embodiment is from the fourth category of the several different categories. The refractive index of the gas and/or the physical length of the measurement path may be changing. In addition, the ratio of the wavelengths of light beams generated by adopted light sources is matched with a certain relative precision to a known ratio value comprised of non-zero quantities. The non-zero quantities may comprise one or more low order non-zero integers.

In the third embodiment and variants thereof, effects of cyclic errors are compensated by using corresponding methods and apparatus of the first embodiment and variants thereof, i.e. by compensating for effects of cyclic errors in a space of electrical interference signals. In the fourth embodiment, effects of cyclic errors are compensated by using the corresponding methods and apparatus of the second embodiment and variants thereof, i.e. by compensating for effects of cyclic errors in a space of phases of electrical interference signals.

The effects of cyclic errors in corrections for effects of a gas in a measuring path, corrections generated from optical dispersion related signals, are greater than the effects of cyclic errors in the signal used for determination of changes in optical path length by one and a half or more orders of magnitude.

In accordance with the preferred apparatus and method of the fourth embodiment, the fourth embodiment comprises light beam 309 and the source of light beam 309, interferometer 369, translator 367, and detector systems 389 and 390 of the third embodiment shown in FIG. 4a. The fourth embodiment further comprises electronic processor 427 shown in a FIGS. 5a and 5b.

Electronic signals of the fourth embodiment corresponding to electronic signals 321, 322, 323, and 324 shown FIG. 4a are hereinafter referenced as electronic signals 421, 422, 423, and 424, respectively. The frequencies of electronic drivers 305 and 306 of the fourth embodiment are $f_6$ and $f_7$, respectively, with angular frequencies $\omega_6$ and $\omega_7$, respectively. The angular frequencies $\omega_{6,Ny}$ and $\omega_{7,Ny}$ are the angular Nyquist frequencies of detector systems 389 and 390, respectively, for the fourth embodiment. Wavelengths of sources 301 and 302 for the fourth embodiment are $\lambda_6$ and $\lambda_7$, respectively, with a known approximate ratio $l_6/l_7$. Reference signals $s_{6,Ref}$ and $s_{7,Ref}$ are transmitted as electronic signals 421 and 422, respectively. Heterodyne signals $s_6$ and $s_7$ of the fourth embodiment correspond to heterodyne signals $s_4$ and $s_5$, respectively, of the third embodiment. Heterodyne signals $s_6$ and $s_7$ are transmitted as electronic signals 423 and 424, respectively.

Figure 5A:
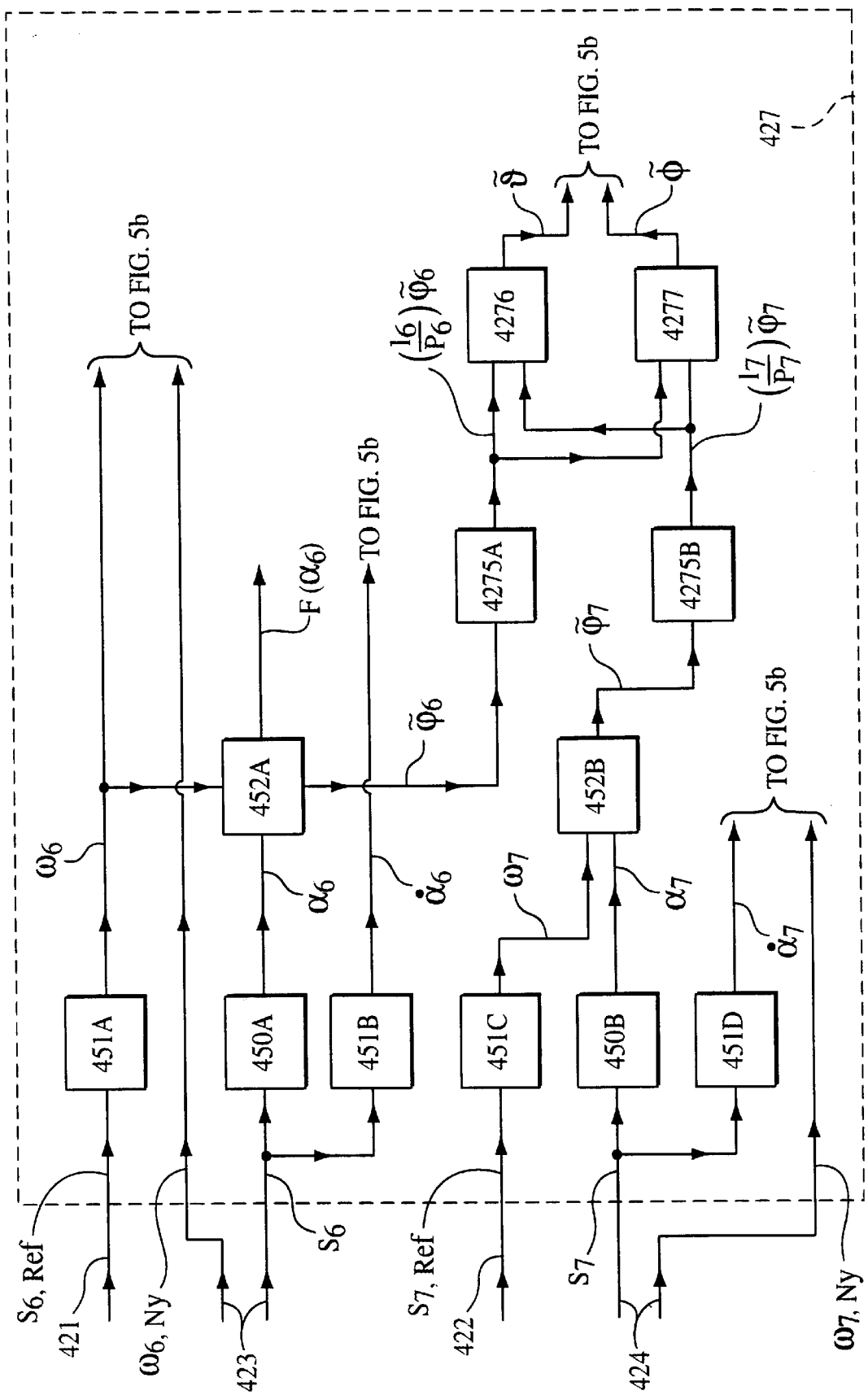
FIGS. 5a and 5b are schematic diagrams of electronic processors for use with the interferometry system of FIG. 4a in a fourth embodiment of the invention.
Figure 5B:
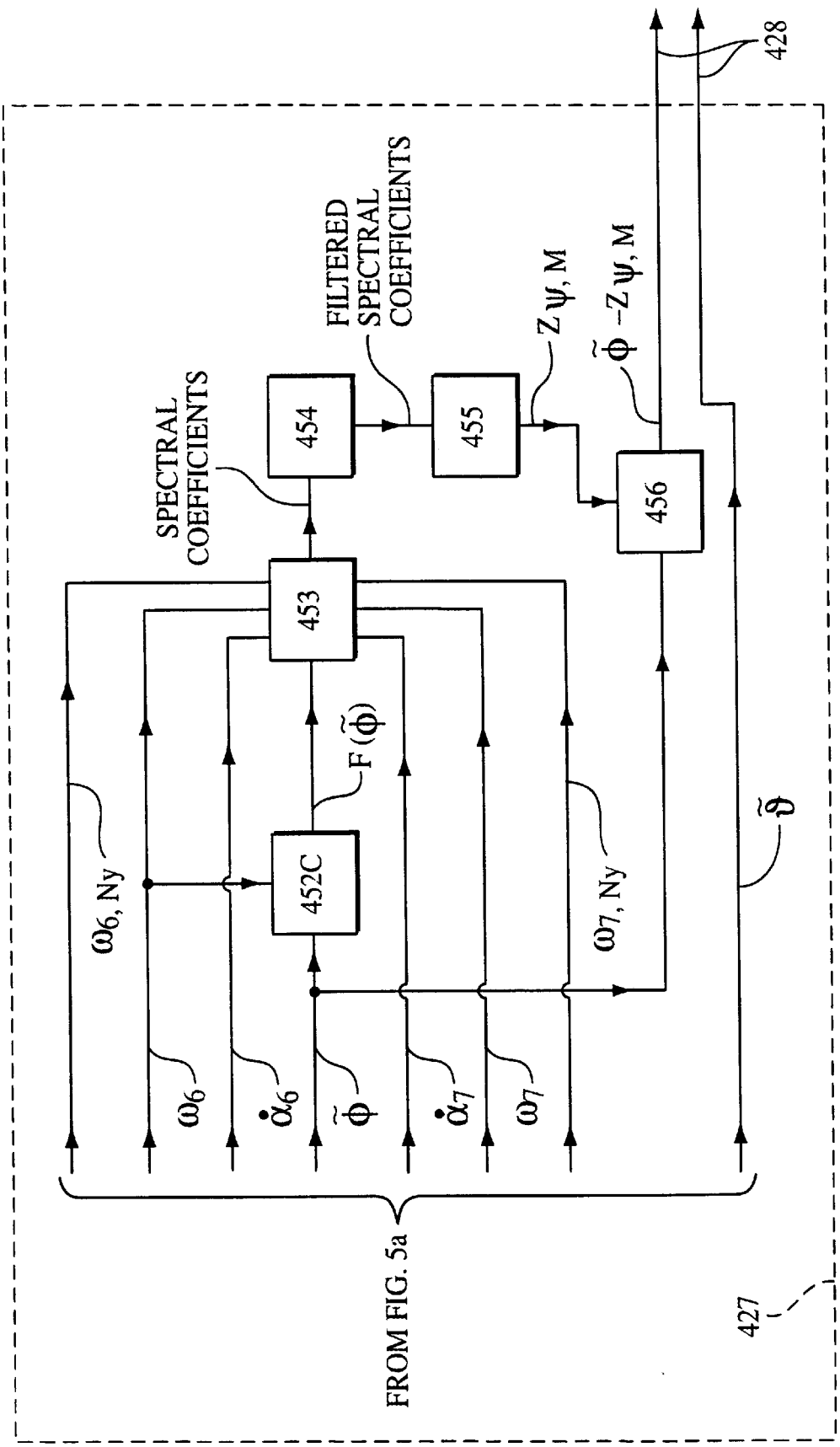

Referring to FIG. 5a, phase 96 is determined by certain elements of electronic processor 427 wherein the certain elements comprise electronic processors 450A, 451A, and 452A that perform like functions as electronic processors 250, 251A, and 252, respectively, of the second embodiment. Phase $\phi_7$ is determined by certain other elements of electronic processor 427 wherein the certain other elements comprise electronic processors 450B, 451C, and 452B perform like functions as electronic processors 250, 251A, and 252, respectively, of the second embodiment. Elements 4275A, 4275B, 4276, and 4277 of the fourth embodiment perform like functions as elements 3275A, 3275B, 3276, and 3277 of the third embodiment to determine a and O). The definitions of 5 and 4 of the fourth embodiment are $$\vartheta = \left(\frac{l_7}{p_7}\tilde{\varphi}_7 + \frac{l_6}{p_6}\tilde{\varphi}_6\right), \tag{69}$$

$$\Phi = \left(\frac{l_7}{p_7}\tilde{\varphi}_7 - \frac{l_6}{p_6}\tilde{\varphi}_6\right), \tag{70}$$

where 96 =6 - 6t and 97 =O 7 - 07t. The descriptions of a 6 and a? are the same as corresponding portions of the description given for a 3 of the second embodiment.

Electronic processor 427 further comprises electronic processors 452C, 453, 454, and 455 to determine ZIPM of QI,M wherein $$Q_\psi = Z_\psi - (K/\chi)\xi_{104}, \tag{71}$$

$$\xi_\psi = \left(\frac{l_7}{p_7}\psi_7 + \frac{l_6}{p_6}\psi_6\right), \tag{72}$$

-continued $$Z_\psi = \left(\frac{l_7}{p_7}\psi_7 - \frac{l_6}{p_6}\psi_6\right). \tag{73}$$

Electronic processors 452C, 453, 454, and 455 of the fourth embodiment perform like functions as electronic processors 252, 253, 254, and 255 of the second embodiment. Phases $\Phi$ and $Z_{\psi,M}$ are transmitted to electronic processor 456 where $\Phi - Z_{\psi,M}$ is generated. Electronic processor 456 of the fourth embodiment performs like functions as electronic processor 256, of the second embodiment.

The cyclic error compensated phase $\Phi - Z_{\psi,M}$ is transmitted to digital computer 429 as signal 428. Digital computer 429 computers dispersion $(n_7 - n_6)$ according to the formula $$(n_7 - n_6) = \frac{1}{\chi \bar{L}[1-(K/\chi)^2]}\left[(\Phi - Z_\psi) - (\vartheta - \xi_\psi)(K/\chi) - Q_\zeta\right] - \tag{74}$$

$$\left(\frac{\Delta L}{\bar{L}}\right)\left(\frac{1}{n_7+n_6}\right).$$

The effects of cyclic errors in $\theta$, $\xi_\psi$, are included in Eq. (74) for completeness. However, the effects of $\xi_\psi$ are not compensated in the fourth embodiment. Note that the effect of $\xi_\psi$ in the computation of the dispersion $(n_7-n_6)$ is reduced by the factor $(K/\chi)$ relative to the effect of $Z_\psi$ and therefore the effect of $\xi_\psi$ can be negligible for end use applications where $|K/\chi|<<1$.

For those applications related to distance measuring interferometry, heterodyne phase $\phi_6$ and phases $\theta$ and $\Phi$ may be used to determine distance $L_6$ as a quantity independent of the effects of the refractive index of the gas in the measuring path of the distance measuring interferometer and corrected for effects of cyclic errors in the dispersion related signals using the formula $$L_6 = \frac{1}{(\chi - K)}\left\{\begin{array}{l}\frac{l_6}{p_6}(\tilde{\varphi}_6 - \zeta_6) - \\ [1-(\Delta L/\bar{L})]\frac{\Gamma}{[1+(K/\chi)]}\left[(\Phi - Z_\psi) - (K/\chi)(\vartheta - \xi_\psi) - Q_\zeta\right]\end{array}\right\} + \Gamma\frac{1}{(n_7+n_6)}\Delta L[1-(\Delta L/\bar{L})]. \tag{75}$$

The remaining description of the fourth embodiment is the same as corresponding portions of the descriptions given for the second and third embodiments of the present invention.

Figure 5C:
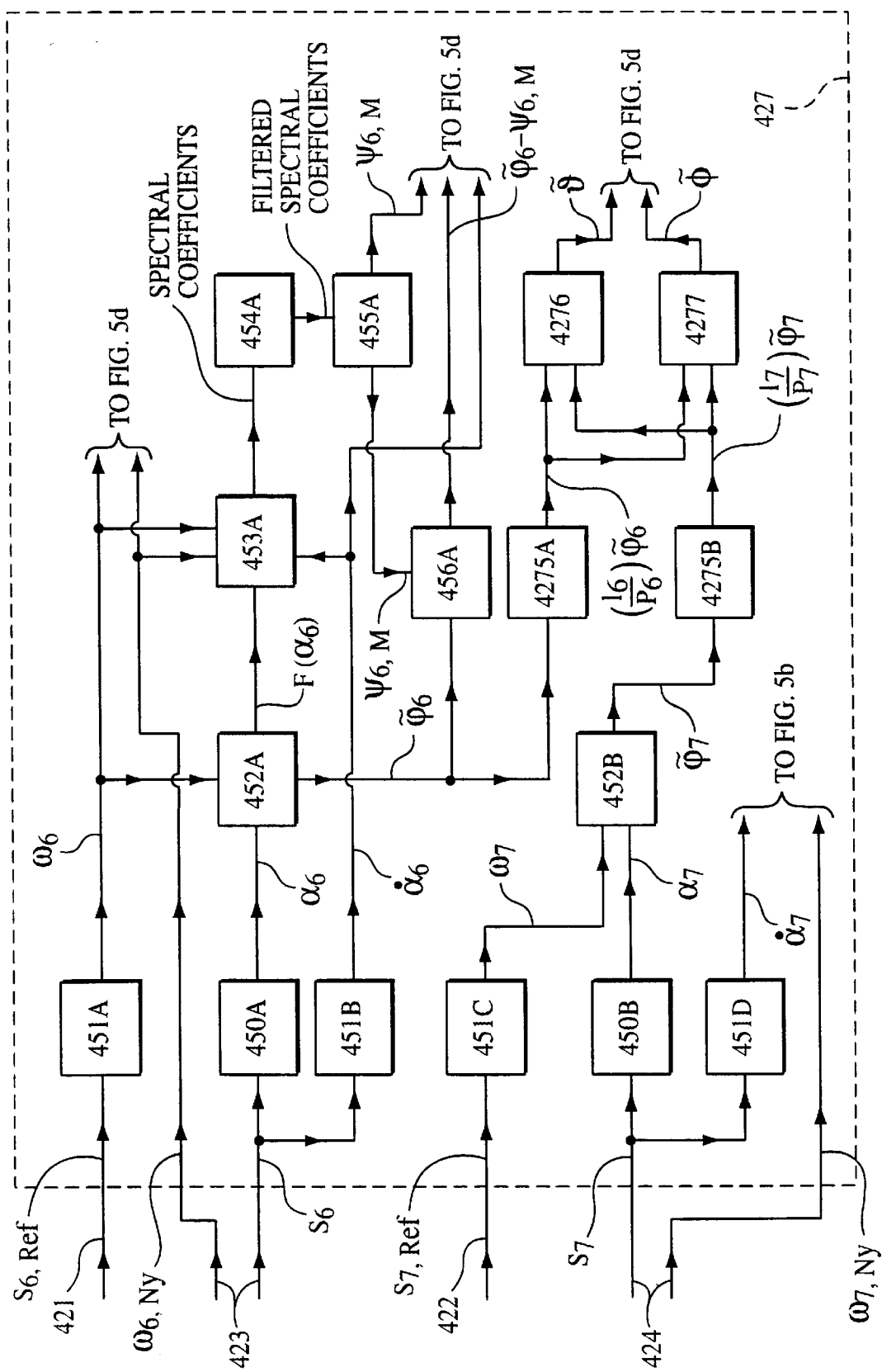
FIGS. 5c and 5d are schematic diagrams of electronic processors for use with the interferometry system of FIG. 4a in a fifth embodiment of the invention.
Figure 5D:
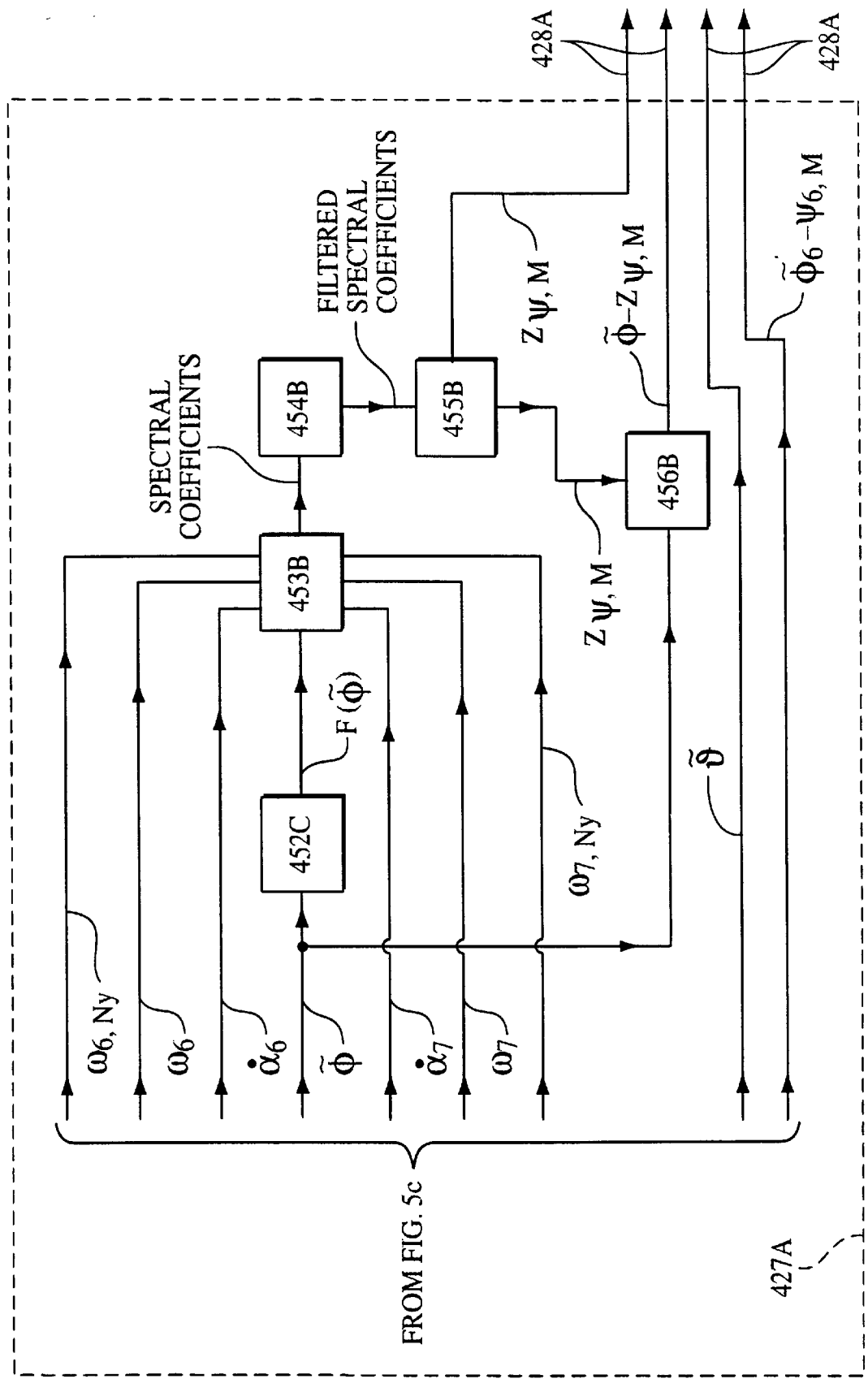

FIGS. 5c and 5d depict in schematic form, in accordance with the preferred apparatus and method of the fifth embodiment of the present invention, electronic processor 527A. The fifth embodiment is from the fourth category of embodiments and comprises beam 309, source of beam 309, interferometer 369, detector system 389, and digital computer 329 of the third embodiment shown in FIG. 4a and electronic processor 427A shown in FIGS. 5c and 5d.

The fifth embodiment comprises apparatus and method for measuring and monitoring dispersion of a gas in a measurement path, the change in the optical path length of the measurement path due to the gas, and a change in the optical path length of the measurement path due to a change in the physical path length of the measurement path. The fifth embodiment further comprises apparatus and method for measuring and compensating for effects of cyclic errors in the measured dispersion of a gas in the measurement path, in the change in the optical path length of the measurement path due to the gas, and in the change in the optical path length of the measurement path due to a change in the physical path length of the measurement path.

In the fourth embodiment, effects of cyclic errors are compensated by using corresponding methods and apparatus of the first embodiment and variants thereof. In the fifth embodiment, the effects of cyclic errors are also compensated by using the corresponding methods and apparatus of the first embodiment and variants thereof.

Electronic processor 427A comprises electronic processors 450A, 451A, 451B, 452A, 453A, 454A, 455A, and 456A that perform like functions as electronic processors 250, 251A, 251B, 252, 253, 254, 255, and 256 of the second embodiment to generated $\psi_{6,M}$ and $\phi_6-\psi_{6,M}$. Electronic processor 427A further comprises electronic processors 450B, 451C, 451D, and 452B that perform the like functions as 250, 251A, 251B, and 252 to generate $\phi_7$. Electronic processors 4275A, 4275B, 4276, and 4277 of the fifth embodiment perform like functions as electronic processors 453B, 454B, 455B, and 456B that perform like functions as electronic processors 4275A, 4275B, 4276, and 4277 of the fourth embodiment to generate $\theta$ and $\Phi$. Electronic processors 452C, 453B, 454B, 455B, and 456B perform like functions as electronic processors 452C, 453, 454, 455, and 456 of the fourth embodiment to generate $Z_{6,M}$ and $\Phi-Z_{6,M}$.

The cyclic error corrected phase $\phi_6-\psi_{6,M}$, phases $\theta$ and $\Phi-Z_{\psi,M}$, and cyclic error correction terms $\psi_{6,M}$ and $Z_{\psi,M}$ are transmitted to digital computer 329 as signal 428A and used by digital computer 329 to determine distance $L_6$ as a quantity independent of the effects of the refractive index of the gas in the measuring path of the distance measuring interferometer and compensated for effects of cyclic errors in both the dispersion and distance measuring related signals using Eq. (75) wherein $\xi_{\psi,M}$ is computed by the formula $$\xi_{\psi,M} = Z_{\psi,M} + 2\left(\frac{l_6}{p_6}\right)\psi_{6,M}. \tag{76}$$

The remaining description of the fifth embodiment is the same as corresponding portions of the descriptions given for the second, third, and fourth embodiments and variants therein.

A sixth embodiment is described, in accordance with the preferred apparatus and method of the sixth embodiment, that comprises both an apparatus and method for measuring and correcting for cyclic errors in both a dispersion measuring related signal and a refractivity measuring related signal or refractivity measuring related signals used to determine intrinsic optical properties of a gas. The sixth embodiment further comprises both an apparatus and method for measuring and correcting for cyclic errors in a wavelength measuring and/or related signal used to determine and/or monitor the wavelength of an optical beam. The sixth embodiment is from the fifth category of the several different categories.

The apparatus and method of the sixth embodiment comprises apparatus and method of the fourth embodiment to measure a dispersion of a gas and a refractivity of the gas to determine a corresponding reciprocal dispersal power of the gas that is corrected for effects of cyclic errors. For the determination of the refractivity of the gas, a vacuum is provided for a measurement path at the respective wavelength. The vacuum measurement path can also be used for measuring and monitoring the wavelength compensated for effects of cyclic errors. The wavelength of the second wavelength used to measure the dispersion can be measured and monitored compensated for cyclic errors by providing a measurement path at the second wavelength.

Reference is made to U.S. application Ser. No. 09/323, 515 entitled "Apparatus And Methods For Measuring Intrinsic Optical Properties Of A Gas," ibid., for further description of apparatus and methods for measuring and monitoring intrinsic optical properties of a gas and wavelengths of optical beams. The foregoing application has been incorporated herein by reference.

The remaining description of the sixth embodiment is the same as corresponding portions of the description given for the fourth embodiment and variants thereof.

A variant of the sixth embodiment is described, in accordance with the preferred apparatus and method of the variant of the sixth embodiment, that comprises both an apparatus and method for measuring and correcting for cyclic errors in both a dispersion measuring related signal and a refractivity measuring related signal or refractivity measuring related signals used to determine intrinsic optical properties of a gas. The variant of the sixth embodiment further comprises both an apparatus and method for measuring and correcting for cyclic errors in a wavelength measuring and/or related signal used to determine and/or monitor the wavelength of an optical beam. The variant of the sixth embodiment is from the fifth category of the several different categories.

The apparatus and method of the variant of the sixth embodiment comprises apparatus and method of the fifth embodiment to measure a dispersion of a gas and a refractivity of the gas to determine a corresponding reciprocal dispersal power of the gas that is corrected for effects of cyclic errors. For the determination of the refractivity of the gas, a vacuum is provided for a measurement path at the respective wavelength. The vacuum measurement path can also be used for measuring and monitoring the wavelength compensated for effects of cyclic errors. The wavelength of the second wavelength used to measure the dispersion can be measured and monitored compensated for cyclic errors by providing a measurement path at the second wavelength.

The remaining description of the variant of the sixth embodiment is the same as corresponding portions of the description given for the fifth and sixth embodiments.

Variations of the signal processing techniques in any of the embodiments described above are also within the scope of the invention. For example, window functions can be applied to the interferometric data prior to analyzing its spectrum to better resolve peaks corresponding to the cyclic errors. In particularly, window functions can be selected to suppress the contribution of the heterodyne interference peak at the dominant frequency at $\omega+\dot\phi$ to the data being analyzed.

The relevance of such window functions can be demonstrated by considering a sliding-window Fourier transform analysis of interferometric data that includes by cyclic errors. The sliding-window Fourier transform samples the interferometric signal, e.g., s(t), over a time window of duration $\tau$, and then Fourier transforms the sampled data. Thus, the transformed data will correspond to the Fourier transform of the unwindowed interferometric signal convolved with the Fourier transform of the time window, which is a sinc function. The convolution of the sinc function with the dominant peak in the interferometric data produces a background in the transformed data that corresponds to the wings of the sinc function. The background can hide the cyclic-error peaks because such peaks typically have much smaller amplitudes than the amplitude of the peak at the dominant frequency at $\omega+\dot\phi$, making it more difficult to accurately characterize the cyclic error coefficients.

To address such difficulties, embodiments can include one or more electronic processors that employ a window function to suppress the broad wings of the sinc function associated with the sliding-window Fourier transform. For example, any of processors 151B, 252, 257, 351B, 351D, 452A, and 452C described above can be modified to cause a window function to be applied to input data to the processor prior to calculating a Fourier transform of the input data. For example, suitable window functions can include any of an approximate Gaussian window, an approximate Lorentzian window, a cosine bell window, a triangular window, and other windows that smooth out the data near its endpoints. The processor multiples the input data by such a window function, which, e.g., is selected to have a time constant comparable to $\tau$, and then Fourier transforms the so-windowed data. Because the window function more gradually reduces the amplitude of the data near its endpoints relative to that of the sliding-window Fourier transform alone, the background caused by the dominant peak in the spectral data is reduced, so that cyclic error peaks can be more accurately identified.

One computationally inexpensive technique for implementing a triangular window function is to add together a series of data samples from a sliding-window data acquisition. In particular, consider a detector that successively samples N point data sequences, wherein each successive data sequence is shifted by less than N increments, e.g., by one increment. Summing together a series of the data sequences at corresponding points can produce a triangular window function. Thus, for example, if successive data sequences were shifted by one increment, M successive data sequences can be summed together to produce an N+M−1 point data sequences, which is then Fourier transformed and whose Fourier transform will have a reduced background because of the successive summing (which produces the triangular window).

Other window functions are also possible, for example, the processor can employ a window function that suppresses the $\omega+\phi$ frequency of the dominant peak, in favor of the cyclic error frequencies. Alternatively, or in addition, the contribution of dominant frequency to the data can be removed from the data, either in the time or frequency domain, to "prewhitened" the data. By removing the contribution of the dominant peak, the cyclic error peaks are more accurately resolved and quantified.

For example, any of processors 151B, 252, 257, 351B, 351D, 452A, and 452C described above can be modified as follows. First, a sliding-window Fourier transform is applied to the input data. Based on the Fourier transform, the amplitude and phase of the dominant peak is determined. Then, a signal equal to the convolution of a delta-function at the dominant frequency and the sinc-function corresponding to the sliding-window is subtracted from the Fourier transformed data to thereby remove the contribution produced by the dominant peak, and better reveal cyclic error peaks. Alternatively, the contribution can be removed in the time domain by subtracting from the input data sampled by the sliding window the contribution of a sinusoidal term at the dominant frequency having the amplitude and phase determined by the sliding window Fourier transform. The resulting input data is then Fourier transformed to reveal the cyclic error peaks. In either domain, the procedure can be iteratively improved based on subsequent calculations of the cyclic error contribution to the amplitude and phase of the dominant peak.

Another technique that can be implemented by the electronic processors of the embodiments described above is the use of a tuned filter (also referred to a phase lock-in) to more accurately determine the cyclic error coefficients. The tuned filter can be used when a particular set of cyclic error terms have been identified as making a statistically significant contribution to the interference signal. Thereafter, the tuned filter can be used repeatedly to update the cyclic error coefficients during use of the interferometry system. The tuned filter is now described with reference to FIG. 8, which is a schematic diagram of an electronic processor 800. For the purposes of the present discussion, electronic processor 800 is a component of electronic processor 127 shown in FIG. 2b as part of the first embodiment. Electronic processor 800 can also be similarly implemented in any of the other embodiments, e.g., as a component of any of electronic processors 127A, 227, 227A, 327, 427, and 427A, in a straightforward manner.

Figure 8:
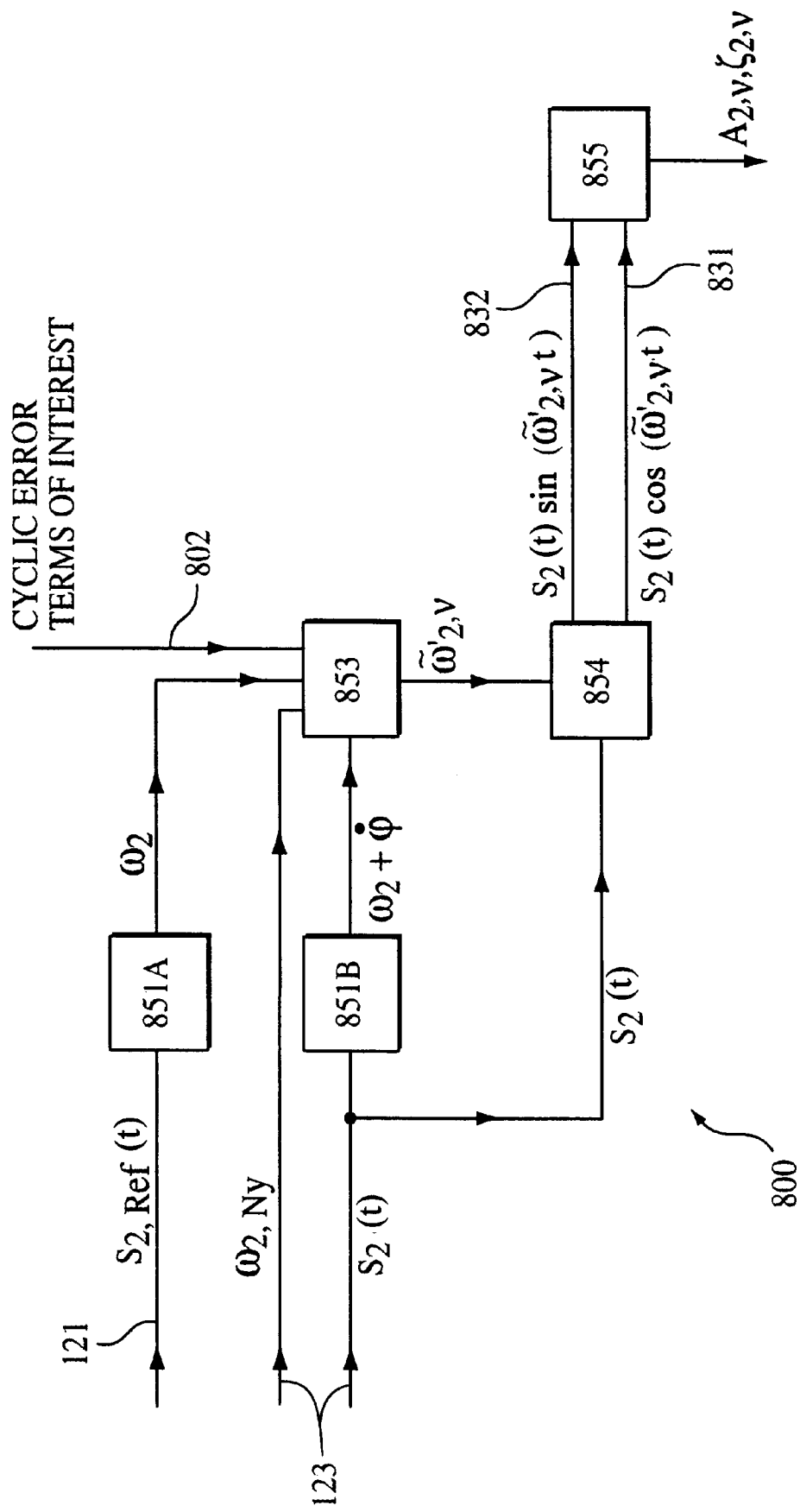
FIG. 8 is a schematic diagram of an electronic processor for use in embodiments of the interferometry systems described herein.

Referring to FIG. 8, electronic processor 800 receives as input signals a portion of signal 123 from detector 185 indicative of the interference signal $s_2(t)$, another portion of signal 123 from detector indicative of the Nyquist frequency $\omega_{2,Ny}$, and a portion of signal 121 from driver 105 indicative of reference signal $s_{2,Ref}(t)$. Signals $s_{2,Ref}(t)$ and $s_2(t)$ pass into spectrum analyzers 851A and 851B, respectively. Spectrum analyzer 851A determines the heterodyne reference frequency $\omega_2$ based on reference signal $s_{2,Ref}(t)$, and spectrum analyzer 851B analyzes the interference signal $s_2(t)$ to determine the frequency of the dominant peak in $s_2(t)$, which corresponds to $\omega_2+\dot{\phi}_2$ (or an alias thereof). The values of $\omega_2$ and $\omega_2+\dot{\phi}_2$ are then sent to processor 853, which also receives as an input the signal indicative of the Nyquist frequency $\omega_{2,Ny}$ and a signal 802 indicating cyclic error terms of interest. As described previously, such terms can be sent from electronic processor 154, which stores information on statistically significant cyclic error terms based on chi-square tests performed by electronic processor 153. Based on the input signals, processor 853 determines the frequency at which each cyclic error term of interest will appear in the signal of $s_2(t)$ for the Doppler shift $\dot{\phi}_2$ of the presently sampled data. In particular, processor 853 determines which of the cyclic error frequencies $\omega_{2,v}$, if any, appear as an alias $\omega_{2,vA}$ according to Eqs. (6) and (7) because of the magnitude of the Doppler shift. Processor 853 then sends the cyclic error frequencies $\omega'_{2,v}$ to electronic processor 854, where $\omega'_{2,v}$ denotes either the fundamental cyclic error frequency $\omega_{2,v}$ or its alias $\omega_{2,vA}$, as appropriate.

Referring still to FIG. 8, electronic processor 854 receives as an additional input another portion of signal 123 from detector 185 indicative of the interference signal $s'_2(t)$. For each of the cyclic error frequencies $\omega'_{2,v}$, electronic processor 854 multiplies $s_2(t)$ by $\cos\omega'_{2,v}$ and $\sin\omega'_{2,v}$ to produce two output signals 831 and 832, respectively, which are sent to processor 855. The multiplication with the cosine and sine terms shifts each frequency in $s_2(t)$ by $+\omega'_{2,v}$ and $-\omega'_{2,v}$ in each of signals 831 and 832, the latter shift producing a low-frequency term (e.g., a zero-frequency term) for the cyclic error term of interest. Processor 855 is a low pass filter, which removes the high frequency terms to retain only the low-frequency term, e.g., by digitally integrating the signal over a time constant T. In particular, the integration yields:

$$\frac{1}{2T}\int_0^T s_2(t)\cos(\tilde{\omega}'_{2,v})\,dt = A_{2,v}\cos(\zeta_{2,v}), \quad (77)$$

and $$\frac{1}{2T}\int_0^T s_2(t)\sin(\tilde{\omega}'_{2,v})\,dt = -A_{2,v}\sin(\zeta_{2,v}). \quad (78)$$

Processor 855 then determines the amplitude $A_{2,v}$ and phase $\zeta_{2,v}$ of the cyclic error coefficient by using an arctangent calculation on the integration results for Eqs. (77) and (78). Alternatively, processor 855 can calculate a complex amplitude for the cyclic error term when using a complex representation for the interference signal including cyclic errors. Processors 854 and 855 repeat the calculations for each of the cyclic error terms of interest. Processor 855 then sends the cyclic error coefficients to one or more subsequent processors in processor 127, such as processor 155, where they are ultimately used to remove the contribution of the cyclic errors terms from the interferometric signal.

Notably, because processors 851A, 851B, and 853 tune the frequencies $\omega'_{2,v}$ by monitoring the Doppler shift $\phi_2$, the time constant of the low pass filter in processor 855 (e.g., the integration time) can be long compared to the rate of change of the Doppler shift. Therefore, the time constant T can be made sufficiently long to produce accurate values for the cyclic error coefficients despite low signal-to-noise in $s_2(t)$. This is particularly important in applications such as microlithography where there is a desire to rapidly change the slew rate of the stage (and therefore the Doppler shift) and thereby increase the productivity of the microlithography tool.

In a further embodiment of electronic processor 800, the second portion of signal 123 from detector 185 indicative of the interference signal $s_2(t)$ can be pre-whitened in the time domain, as described above. In particular, the signal is pre-whitened prior to passing into an electronic processor 854 to thereby remove the contribution of the dominant heterodyne term at frequency $\omega_2+\phi_2$ (or its alias) and produce a signal indicative of an approximate value for $s_{2,\psi}(t)$ (defined by Eq. (5)), which is then sent to electronic processor 854.

Another variation on the signal processing techniques of the embodiments described above is noted. Aspects of the invention generally propose to characterize the cyclic error contribution to the interferometric signal as a spectral representation. As described above in detail, whether particular cyclic error terms contribute to the dominant peak in the interferometric signal depends on the Doppler shift and Nyquist frequency. Because the Doppler shift changes during operation of the interferometry system, particular cyclic error terms can be characterized when the Doppler shift causes such cyclic error terms to be spectrally separated from the dominant term. Ultimately, a spectral representation of all statistically relevant cyclic error terms can be constructed, and the phase $\phi$ of the interference signal (absent cyclic error contributions) can be determined iteratively by subtracting the cyclic error contribution to the interference signal in the time domain based on the spectral representation and the previous estimation of $\phi$. For example, processors 152, 155, and 156 in processor 127 of the first embodiment perform such an iterative calculation.

Figure 9:
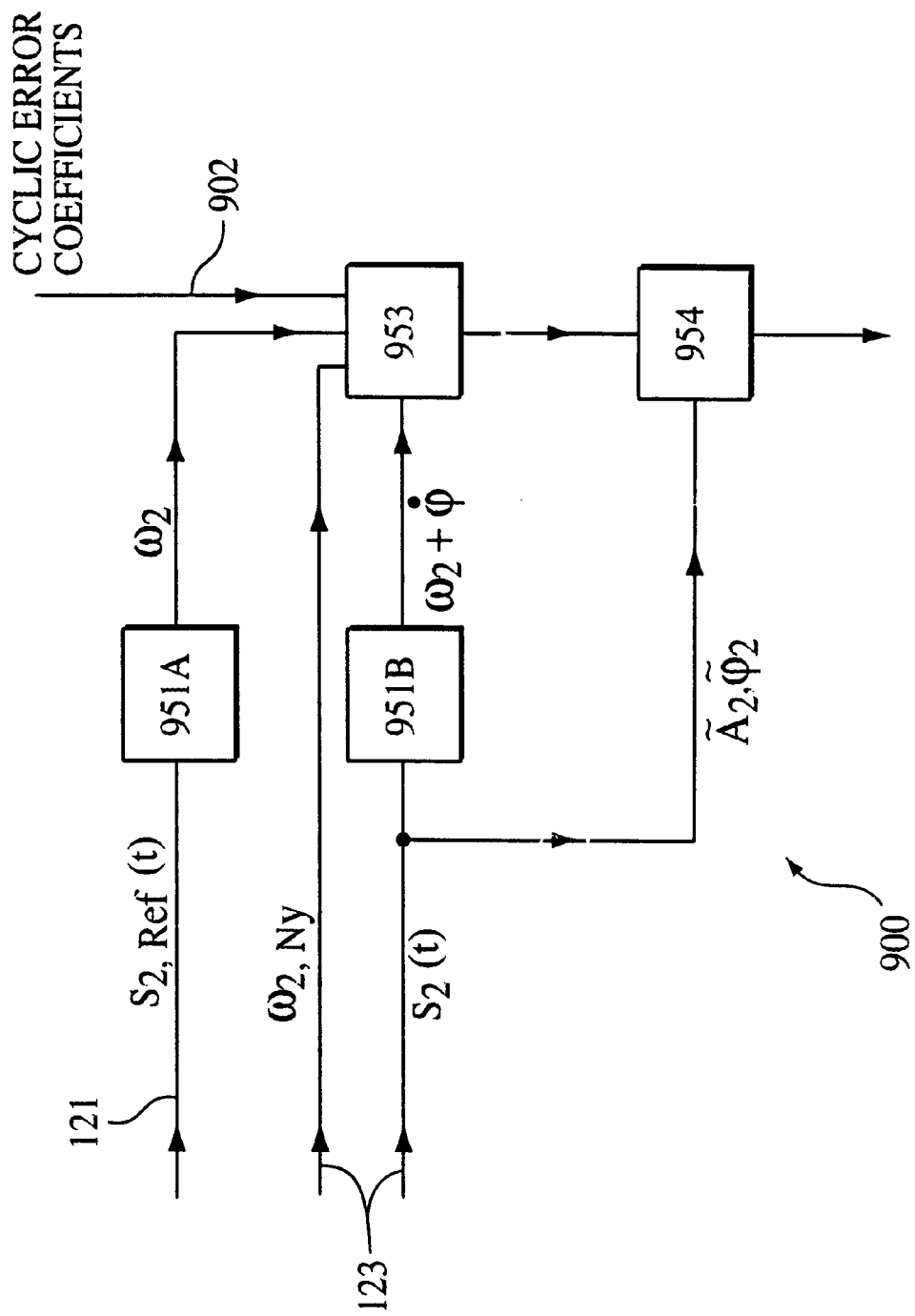
FIG. 9 is a schematic diagram of another electronic processor for use in embodiments of the interferometry systems described herein.

In an alternative procedure, the cyclic error contribution is subtracted from the interference signal in the frequency domain to iteratively determine the phase $\phi$. In such instances, only those cyclic errors that contribute to the interference signal at the dominant frequency need to be considered. For example, FIG. 9 is a schematic diagram of an electronic processor 900 that implements such a procedure. For the purposes of the present discussion, electronic processor 900 is a component of electronic processor 127 shown in FIG. 2b as part of the first embodiment. Electronic processor 900 can also be similarly implemented in any of the other embodiments, e.g., as a component of any of electronic processors 127A, 227, 227A, 327, 427, and 427A, in a straightforward manner.

Referring to FIG. 9, electronic processor 900 receives as input signals a portion of signal 123 from detector 185 indicative of the interference signal $s_2(t)$, another portion of signal 123 from detector indicative of the Nyquist frequency $\omega_{2,Ny}$, and a portion of signal 121 from driver 105 indicative of reference signal $s_{2,Ref}(t)$. Signals $s_{2,Ref}(t)$ and $s_2(t)$ pass into spectrum analyzers 951A and 951B, respectively. Spectrum analyzer 951A determines the heterodyne reference frequency $\omega_2$ based on reference signal $s_{2,Ref}(t)$, and spectrum analyzer 951B analyzes the interference signal $s_2(t)$ to determine the frequency of the dominant peak in $s_2(t)$, which corresponds to $\omega_2+\phi_2$ (or an alias thereof). The values of $\omega_2$ and $\omega_2+\phi_2$ are then sent to processor 953, which also receives as an input the signal indicative of the Nyquist frequency $\omega_{2,Ny}$ and a signal 902 indicative of values for the cyclic error coefficients, e.g., the amplitudes $A_{2,v}$ and phases $\zeta_{2,v}$ determined by processor 800. Processor 953 determines which of the cyclic error terms contribute to the signal $s_2(t)$ at the dominant frequency for the presently sampled data (according to, e.g., Eqs. (2), (6), and (7)), and then sends the corresponding cyclic error coefficients to processor 954.

Still referring to FIG. 9, spectrum analyzer 951B further determines the amplitude $\tilde{A}_2$ and phase $\phi_2$ of the dominant peak in $s_2(t)$, e.g., by a sliding-window Fourier transform, and sends the amplitude and phase to processor 954. Processor 954 then iteratively determines the phase $\phi_2$ for the interference signal in the absence of cyclic errors by determining a value for $\phi_2$ that is self-consistent with the amplitude $\tilde{A}_2$ and phase $\phi_2$ and the cyclic error terms from processor 953 that were determined to contribute to the interference signal at the dominant frequency. Under some circumstances, the value for the phase $\phi_2$ determined by the frequency domain technique of processor 900 may be more accurate than that determined by the time-domain technique because only those cyclic errors that contribute at the dominant frequency are used.

It is also noted that embodiments that combine features of processors 127, 127A, 227, 227A, 327, 427, 427A, 800, and 900, can be modified to remove redundant components. For example, electronic processor 851A in processor 800 can be replaced by processor 151A in processor 127 when processor 800 is a component of processor 127 because processors 151A and 851A perform the same function.

The interferometry systems described above quantify nonlinearities (e.g., cyclic errors) and use the quantified nonlinearities to correct distance measurements, dispersion measurements, and intrinsic optical property measurements for the presence of such nonlinearities. As a result, such interferometry systems provide highly accurate measurements. Such systems can be especially useful in lithography applications used in fabricating large scale integrated circuits such as computer chips and the like. Lithography is the key technology driver for the semiconductor manufacturing industry. Overlay improvement is one of the five most difficult challenges down to and below 100 nm line widths (design rules), see for example the *Semiconductor Industry Roadmap*, p82 (1997).

Overlay depends directly on the performance, i.e. accuracy and precision, of the distance measuring interferometers used to position the wafer and reticle (or mask) stages. Since a lithography tool may produce $50–100M/year of product, the economic value from improved performance distance measuring interferometers is substantial. Each 1% increase in yield of the lithography tool results in approximately $1M/year economic benefit to the integrated circuit manufacturer and substantial competitive advantage to the lithography tool vendor.

The function of a lithography tool is to direct spatially patterned radiation onto a photoresist-coated wafer. The process involves determining which location of the wafer is to receive the radiation (alignment) and applying the radiation to the photoresist at that location (exposure).

To properly position the wafer, the wafer includes alignment marks on the wafer that can be measured by dedicated sensors. The measured positions of the alignment marks define the location of the wafer within the tool. This information, along with a specification of the desired patterning of the wafer surface, guides the alignment of the wafer relative to the spatially patterned radiation. Based on such information, a translatable stage supporting the photoresist-coated wafer moves the wafer such that the radiation will expose the correct location of the wafer.

During exposure, a radiation source illuminates a patterned reticle, which scatters the radiation to produce the spatially patterned radiation. The reticle is also referred to as a mask, and these terms are used interchangeably below. In the case of reduction lithography, a reduction lens collects the scattered radiation and forms a reduced image of the reticle pattern. Alternatively, in the case of proximity printing, the scattered radiation propagates a small distance (typically on the order of microns) before contacting the wafer to produce a 1:1 image of the reticle pattern. The radiation initiates photo-chemical processes in the resist that convert the radiation pattern into a latent image within the resist.

Interferometry systems are important components of the positioning mechanisms that control the position of the wafer and reticle, and register the reticle image on the wafer. If such interferometry systems include the phase measurement portion described above, the accuracy of distances measured by the systems increases as cyclic error contributions to the distance measurement are minimized.

In general, the lithography system, also referred to as an exposure system, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes resist coated onto the wafer. The illumination system also includes a mask stage for supporting the mask and a positioning system for adjusting the position of the mask stage relative to the radiation directed through the mask. The wafer positioning system includes a wafer stage for supporting the wafer and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithography: Science and Technology* (Marcel Dekker, Inc., New York, 1998), the contents of which is incorporated herein by reference.

Interferometry systems described above can be used to precisely measure the positions of each of the wafer stage and mask stage relative to other components of the exposure system, such as the lens assembly, radiation source, or support structure. In such cases, the interferometry system can be attached to a stationary structure and the measurement object attached to a movable element such as one of the mask and wafer stages. Alternatively, the situation can be reversed, with the interferometry system attached to a movable object and the measurement object attached to a stationary object.

More generally, such interferometry systems can be used to measure the position of any one component of the exposure system relative to any other component of the exposure system, in which the interferometry system is attached to, or supported by, one of the components and the measurement object is attached, or is supported by the other of the components.

Figure 6A:
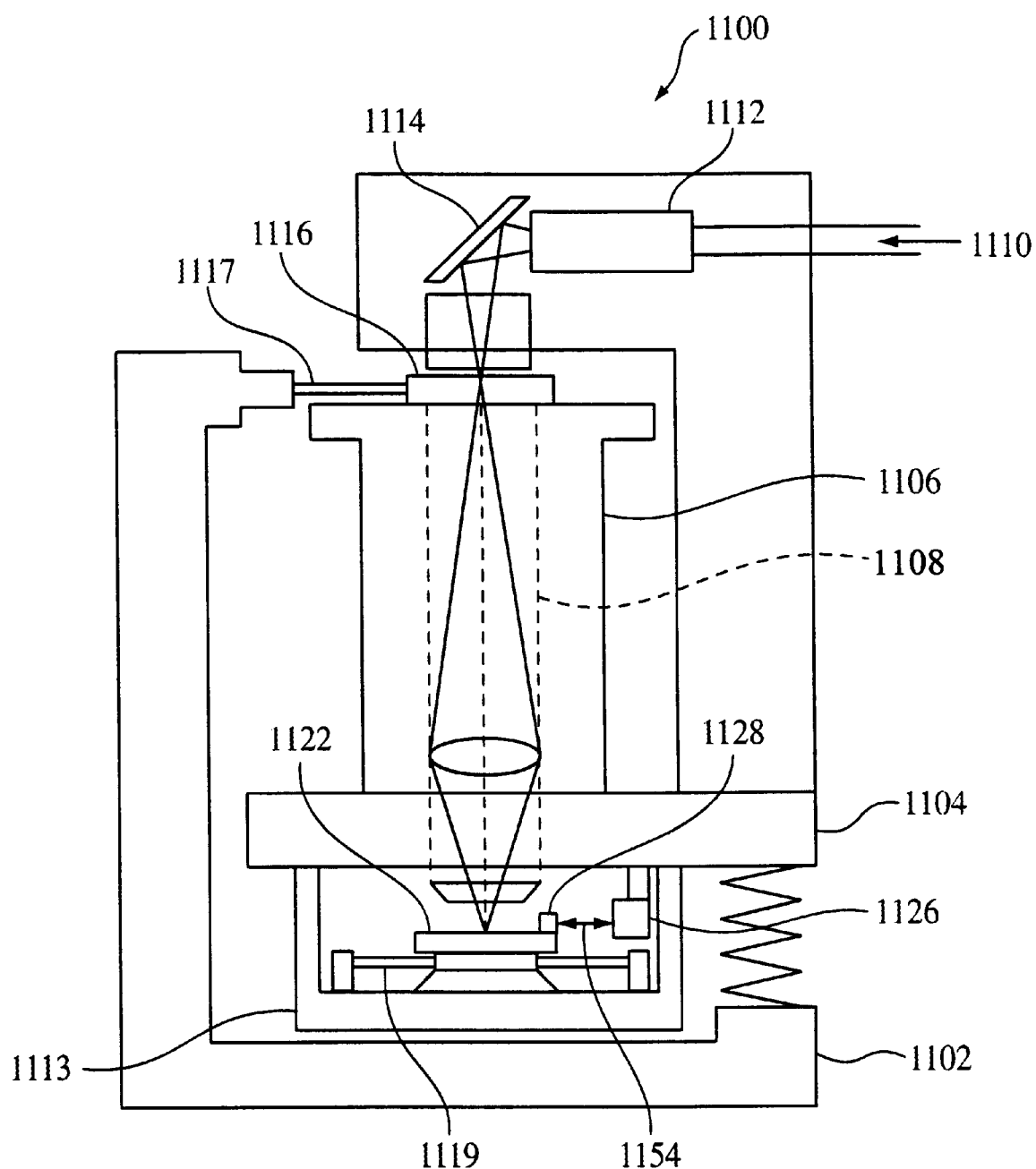
FIG. 6a is schematic diagram of a lithography system that includes an interferometry system described here and is used to make integrated circuits.

An example of a lithography scanner 1100 using an interferometry system 1126 is shown in FIG. 6a. The interferometry system is used to precisely measure the position of a wafer (not shown) within an exposure system. Here, stage 1122 is used to position and support the wafer relative to an exposure station. Scanner 1100 includes a frame 1102, which carries other support structures and various components carried on those structures. An exposure base 1104 has mounted on top of it a lens housing 1106 atop of which is mounted a reticle or mask stage 1116, which is used to support a reticle or mask. A positioning system for positioning the mask relative to the exposure station is indicated schematically by element 1117. Positioning system 1117 can include, e.g., piezoelectric transducer elements and corresponding control electronics. Although, it is not included in this described embodiment, one or more of the interferometry systems described above can also be used to precisely measure the position of the mask stage as well as other moveable elements whose position must be accurately monitored in processes for fabricating lithographic structures (see supra Sheats and Smith *Microlithography: Science and Technology*).

Suspended below exposure base 1104 is a support base 1113 that carries wafer stage 1122. Stage 1122 includes a plane mirror 1128 for reflecting a measurement beam 1154 directed to the stage by interferometry system 1126. A positioning system for positioning stage 1122 relative to interferometry system 1126 is indicated schematically by element 1119. Positioning system 1119 can include, e.g., piezoelectric transducer elements and corresponding control electronics. The measurement beam reflects back to the interferometry system, which is mounted on exposure base 1104. The interferometry system can be any of the embodiments described previously.

During operation, a radiation beam 1110, e.g., an ultraviolet (UV) beam from a UV laser (not shown), passes through a beam shaping optics assembly 1112 and travels downward after reflecting from mirror 1114. Thereafter, the radiation beam passes through a mask (not shown) carried by mask stage 1116. The mask (not shown) is imaged onto a wafer (not shown) on wafer stage 1122 via a lens assembly 1108 carried in a lens housing 1106. Base 1104 and the various components supported by it are isolated from environmental vibrations by a damping system depicted by spring 1120.

In other embodiments of the lithographic scanner, one or more of the interferometry systems described previously can be used to measure distance along multiple axes and angles associated for example with, but not limited to, the wafer and reticle (or mask) stages. Also, rather than a UV laser beam, other beams can be used to expose the wafer including, e.g., x-ray beams, electron beams, ion beams, and visible optical beams.

In some embodiments, the lithographic scanner can include what is known in the art as a column reference. In such embodiments, the interferometry system 1126 directs the reference beam (not shown) along an external reference path that contacts a reference mirror (not shown) mounted on some structure that directs the radiation beam, e.g., lens housing 1106. The reference mirror reflects the reference beam back to the interferometry system. The interference signal produce by interferometry system 1126 when combining measurement beam 1154 reflected from stage 1122 and the reference beam reflected from a reference mirror mounted on the lens housing 1106 indicates changes in the position of the stage relative to the radiation beam. Furthermore, in other embodiments the interferometry system 1126 can be positioned to measure changes in the position of reticle (or mask) stage 1116 or other movable components of the scanner system. Finally, the interferometry systems can be used in a similar fashion with lithography systems involving steppers, in addition to, or rather than, scanners.

Figure 6B:
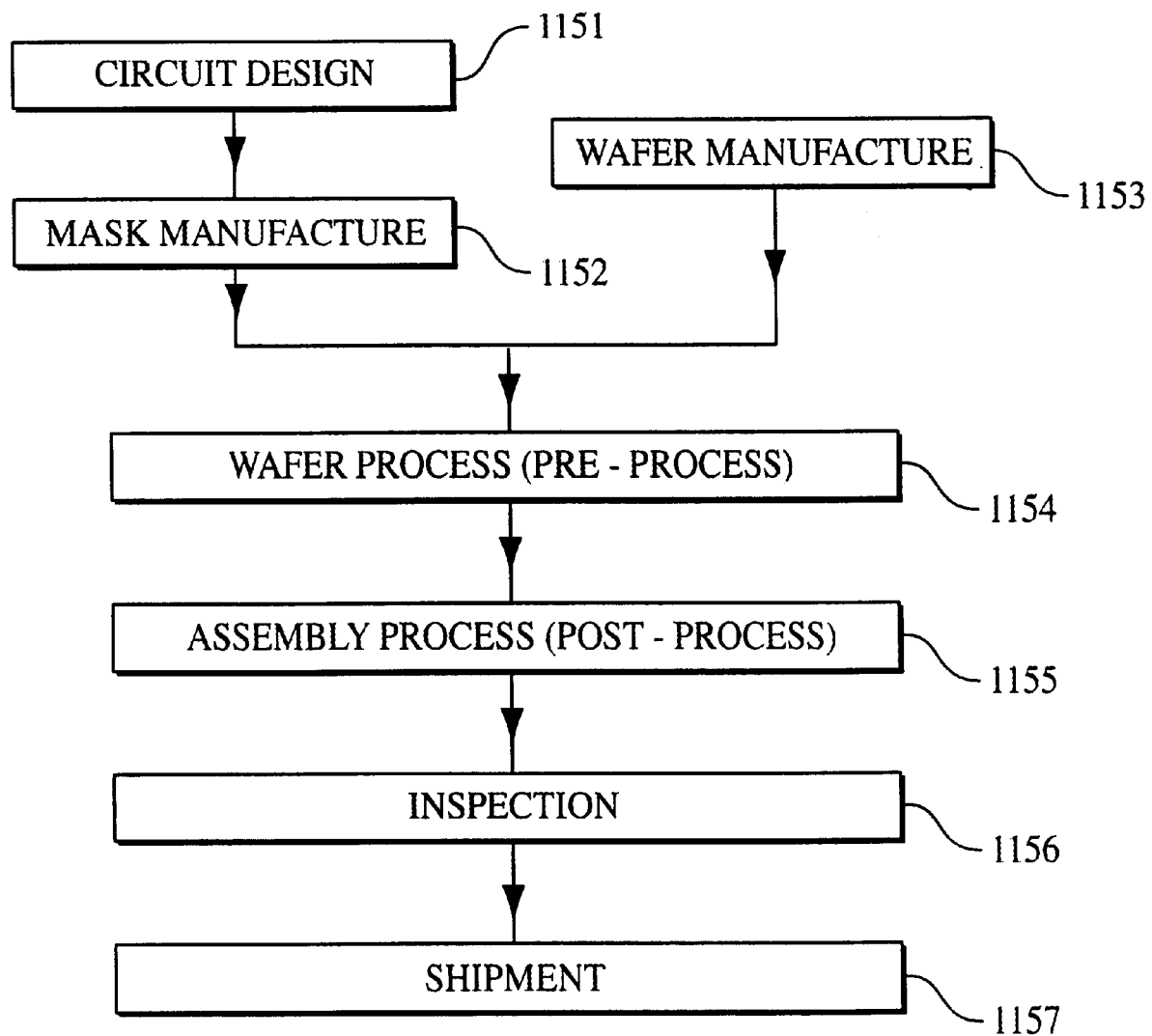
FIGS. 6b–c are flow charts that described steps for making integrated circuits.

As is well known in the art, lithography is a critical part of manufacturing methods for making semiconducting devices. For example, U.S. Pat. No. 5,483,343 outlines steps for such manufacturing methods. These steps are described below with reference to FIGS. 6b and 6c. FIG. 6b is a flow chart of the sequence of manufacturing a semiconductor device such as a semiconductor chip (e.g. IC or LSI), a liquid crystal panel or a CCD. Step 1151 is a design process for designing the circuit of a semiconductor device. Step 1152 is a process for manufacturing a mask on the basis of the circuit pattern design. Step 1153 is a process for manufacturing a wafer by using a material such as silicon.

Step 1154 is a wafer process which is called a pre-process wherein, by using the so prepared mask and wafer, circuits are formed on the wafer through lithography. To form circuits on the wafer that correspond with sufficient spatial resolution those patterns on the mask, interferometric positioning of the lithography tool relative the wafer is necessary. The interferometry methods and systems described herein can be especially useful to improve the effectiveness of the lithography used in the wafer process.

Step 1155 is an assembling step, which is called a post-process wherein the wafer processed by step 1154 is formed into semiconductor chips. This step includes assembling (dicing and bonding) and packaging (chip sealing). Step 1156 is an inspection step wherein operability check, durability check and so on of the semiconductor devices produced by step 1155 are carried out. With these processes, semiconductor devices are finished and they are shipped (step 1157).

Figure 6C:
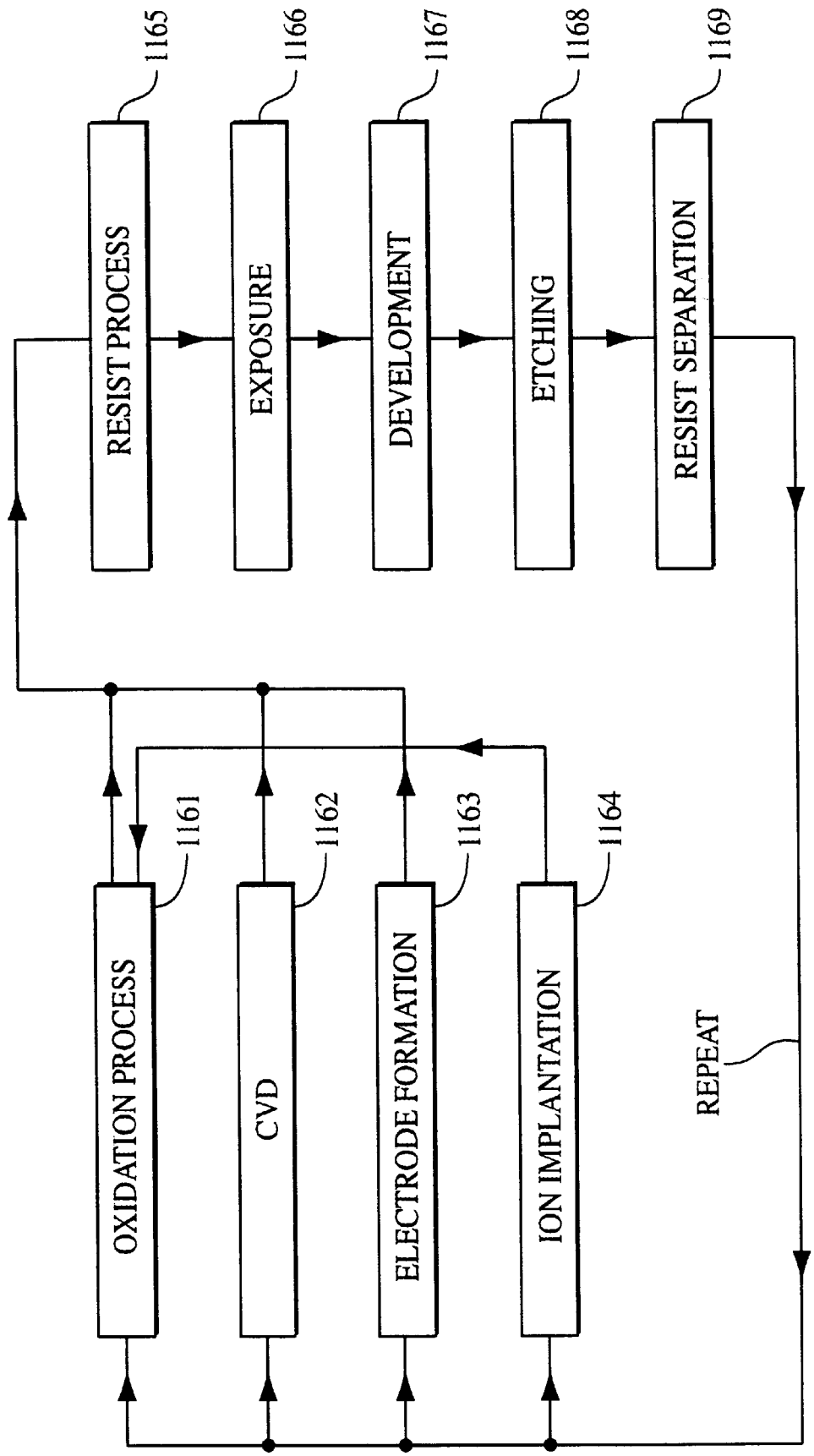

FIG. 6c is a flow chart showing details of the wafer process. Step 1161 is an oxidation process for oxidizing the surface of a wafer. Step 1162 is a CVD process for forming an insulating film on the wafer surface. Step 1163 is an electrode forming process for forming electrodes on the wafer by vapor deposition. Step 1164 is an ion implanting process for implanting ions to the wafer. Step 1165 is a resist process for applying a resist (photosensitive material) to the wafer. Step 1166 is an exposure process for printing, by exposure (i.e., lithography), the circuit pattern of the mask on the wafer through the exposure apparatus described above. Once again, as described above, the use of the interferometry systems and methods described herein improve the accuracy and resolution of such lithography steps.

Step 1167 is a developing process for developing the exposed wafer. Step 1168 is an etching process for removing portions other than the developed resist image. Step 1169 is a resist separation process for separating the resist material remaining on the wafer after being subjected to the etching process. By repeating these processes, circuit patterns are formed and superimposed on the wafer.

The interferometry systems described above can also be used in other applications in which the relative position of an object needs to be measured precisely. For example, in applications in which a write beam such as a laser, x-ray, ion, or electron beam, marks a pattern onto a substrate as either the substrate or beam moves, the interferometry systems can be used to measure the relative movement between the substrate and write beam.

Figure 7:
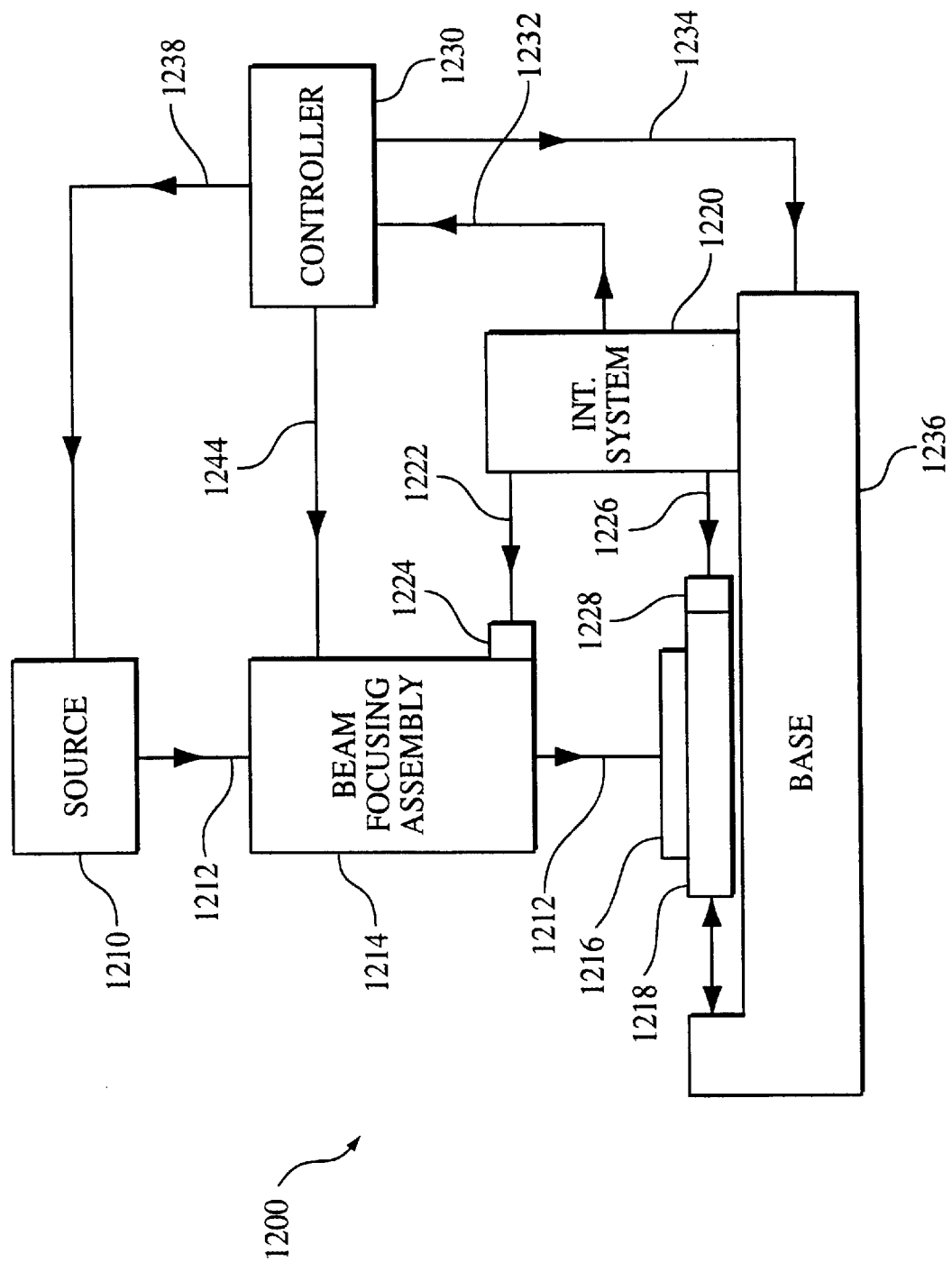
FIG. 7 is a schematic of a beam writing system that includes an interferometry system described herein.

As an example, a schematic of a beam writing system 1200 is shown in FIG. 7. A source 1210 generates a write beam 1212, and a beam focusing assembly 1214 directs the radiation beam to a substrate 1216 supported by a movable stage 1218. To determine the relative position of the stage, an interferometry system 1220 directs a reference beam 1222 to a mirror 1224 mounted on beam focusing assembly 1214 and a measurement beam 1226 to a mirror 1228 mounted on stage 1218. Since the reference beam contacts a mirror mounted on the beam focusing assembly, the beam writing system is an example of a system that uses a column reference. Interferometry system 1220 can be any of the interferometry systems described previously. Changes in the position measured by the interferometry system correspond to changes in the relative position of write beam 1212 on substrate 1216. Interferometry system 1220 sends a measurement signal 1232 to controller 1230 that is indicative of the relative position of write beam 1212 on substrate 1216. Controller 1230 sends an output signal 1234 to a base 1236 that supports and positions stage 1218. In addition, controller 1230 sends a signal 1238 to source 1210 to vary the intensity of, or block, write beam 1212 so that the write beam contacts the substrate with an intensity sufficient to cause photophysical or photochemical change only at selected positions of the substrate.

Furthermore, in some embodiments, controller 1230 can cause beam focusing assembly 1214 to scan the write beam over a region of the substrate, e.g., using signal 1244. As a result, controller 1230 directs the other components of the system to pattern the substrate. The patterning is typically based on an electronic design pattern stored in the controller. In some applications the write beam patterns a resist coated on the substrate and in other applications the write beam directly patterns, e.g., etches, the substrate.

An important application of such a system is the fabrication of masks and reticles used in the lithography methods described previously. For example, to fabricate a lithography mask an electron beam can be used to pattern a chromium-coated glass substrate. In such cases where the write beam is an electron beam, the beam writing system encloses the electron beam path in a vacuum. Also, in cases where the write beam is, e.g., an electron or ion beam, the beam focusing assembly includes electric field generators such as quadrapole lenses for focusing and directing the charged particles onto the substrate under vacuum. In other cases where the write beam is a radiation beam, e.g., x-ray, UV, or visible radiation, the beam focusing assembly includes corresponding optics and for focusing and directing the radiation to the substrate.

Other aspects, advantages, and modifications are within the scope of the following claims.

What is claimed is:

1. An interferometry system comprising:
   an interferometer which during operation directs two beams along separate paths and then combines the beams to produce an overlapping pair of exit beams, the separate paths defining an optical path length difference;
   a detector which responds to optical interference between the overlapping pair of exit beams and produces an interference signal s(t) indicative of the optical path length difference, the signal s(t) including a dominant term having a frequency equal to the sum of the frequency splitting ω between the two beams, if any, and a Doppler shift φ defined by the rate of change of the optical path length difference, wherein properties of the interferometry system causes the signal s(t) to further include additional terms each having a frequency not equal to the sum of the frequency splitting ω and the Doppler shift φ; and
   an analyzer coupled to the detector which during operation: i) applies a window function to a sequence of values of the signal s(t); ii) Fourier transforms the windowed sequence of values, the Fourier transform defining a power spectrum equal to the square modulus of the Fourier transform; and iii) identifies at least one of the additional terms based on at least one peak in the power spectrum at a frequency not equal to the sum of the frequency splitting ω and the Doppler shift φ.

2. The system of claim 1, wherein during operation the analyzer further quantifies at least one of the additional terms based on the amplitude and phase of the Fourier transform at the frequency of the at least one peak in the power spectrum.

3. The system of claim 2, wherein during operation the analyzer further uses the quantified additional term to estimate a change in the optical path length difference corresponding to a particular value of s(t).

4. The system of claim 3, wherein during operation the analyzer uses the estimated change in optical path length difference to do at least one of determine a change in physical path length, determine a change in dispersion, determine an intrinsic value of a gas, and monitor the wavelength of the beams.

5. The system of claim 1, wherein during operation the analyzer further produces a signal indicative of system degradation when the amplitude of the identified additional term exceeds a threshold value, and wherein the system further comprises an alert mechanism coupled to the analyzer and responsive to the system degradation signal.

6. The system of claim 5, wherein the alert mechanism comprises at least one of a visual display, a sound system, a warning light, and a printer.

7. The system of claim 1, wherein the window function reduces the amplitude of the sequence of values of s(t) as the sequence approaches either of its endpoints.

8. The system of claim 1, wherein the window function suppresses the frequency equal to the sum of the frequency splitting ω and the Doppler shift φ relative to a frequency of at least one of the additional terms.

9. An interferometry system comprising:
   an interferometer which during operation directs two beams along separate paths and then combines the beams to produce an overlapping pair of exit beams, the separate paths defining an optical path length difference;
   a detector which responds to optical interference between the overlapping pair of exit beams and produces an interference signal s(t) indicative of the optical path length difference, the signal s(t) including a dominant term having a frequency equal to the sum of the frequency splitting ω between the two beams, if any, and a Doppler shift φ defined by the rate of change of the optical path length difference, wherein properties of the interferometry system causes the signal s(t) to further include additional terms each having a frequency not equal to the sum of the frequency splitting ω and the Doppler shift φ; and
   an analyzer coupled to the detector and comprising a low-pass filter, wherein during operation the analyzer: i) tracks the value of the Doppler shift based on the signal s(t); ii) calculates the frequency $\omega'_v$ of one of the additional terms based on the tracked value of the Doppler shift; iii) generates a first tuned-filter signal equal to $s(t)\cos(\omega'_v t)$ and a second tuned-filter signal equal to $s(t)\sin(\omega'_v t)$; and iv) passes the tuned-filter signals through the low-pass filter to quantify the additional term corresponding to $\omega'_v$.

10. The interferometry system of claim 9, wherein during operation the analyzer calculates the frequency $\omega'_v$ of one of the additional terms based on the tracked value of the Doppler shift and a Nyquist frequency defined by the sampling rate of the detector.

11. The interferometry system of claim 9, wherein during operation the analyzer generates additional tuned-filter signals based on the frequency of at least one other additional term to quantify the at least one other additional term.

12. The interferometry system of claim 9, wherein during operation the analyzer further uses the quantified additional term to estimate a change in the optical path length difference corresponding to a particular value of s(t).

13. The system of claim 12, wherein during operation the analyzer uses the estimated change in optical path length difference to do at least one of determine a change in physical path length, determine a change in dispersion, determine an intrinsic value of a gas, and monitor the wavelength of the beams.

14. The system of claim 9, wherein during operation the analyzer further produces a signal indicative of system degradation when the amplitude of the quantified additional term exceeds a threshold value, and wherein the system further comprises an alert mechanism coupled to the analyzer and responsive to the system degradation signal.

15. The system of claim 14, wherein the alert mechanism comprises at least one of a visual display, a sound system, a warning light, and a printer.

16. An interferometry system comprising:
   an interferometer which during operation directs two beams along separate paths and then combines the beams to produce an overlapping pair of exit beams, the separate paths defining an optical path length difference;
   a detector which responds to optical interference between the overlapping pair of exit beams and produces an interference signal s(t) indicative of the optical path length difference, the signal s(t) including a dominant term having a frequency equal to the sum of the frequency splitting ω between the two beams, if any, and a Doppler shift φ defined by the rate of change of the optical path length difference, wherein properties of the interferometry system causes the signal s(t) to further include additional terms each having a frequency not equal to the sum of the frequency splitting ω and the Doppler shift φ; and an analyzer coupled to the detector which during operation: i) provides a quantification for at least some of the additional terms; ii) Fourier transforms at least one set of values of s(t); and iii) estimates a value for the optical path length difference based on the amplitude and phase of the Fourier transform at the frequency ω+φ and values of the quantification for the additional terms that contribute to the Fourier transform at the frequency ω+φ based on the Doppler shift φ corresponding to the set of values of s(t).

17. The interferometry system of claim 16, wherein during operation the analyzer identifies which of the additional terms in the quantification contribute to the Fourier transform at the frequency ω+φ based on the Doppler shift φ corresponding to the set of values of s(t) and a Nyquist frequency corresponding to the sampling rate of the detector.

18. The system of claim 16, wherein during operation the analyzer uses the estimated change in optical path length difference to do at least one of determine a change in physical path length, determine a change in dispersion, determine an intrinsic value of a gas, and monitor the wavelength of the beams.

19. A lithography system for use in fabricating integrated circuits on a wafer, the system comprising:

a stage for supporting the wafer;

an illumination system for imaging spatially patterned radiation onto the wafer;

a positioning system for adjusting the position of the stage relative to the imaged radiation; and the interferometry system of claim 1, 9, or 16 for measuring the position of the stage.

20. A lithography system for use in fabricating integrated circuits on a wafer, the system comprising:

a stage for supporting the wafer; and an illumination system including a radiation source, a mask, a positioning system, a lens assembly, and the interferometry system of claim 1, 9, or 16 wherein during operation the source directs radiation through the mask to produce spatially patterned radiation, the positioning system adjusts the position of the mask relative to the radiation from the source, the lens assembly images the spatially patterned radiation onto the wafer, and the interferometry system measures the position of the mask relative to the radiation from the source.

21. A beam writing system for use in fabricating a lithography mask, the system comprising:

a source providing a write beam to pattern a substrate;

a stage supporting the substrate;

a beam directing assembly for delivering the write beam to the substrate;

a positioning system for positioning the stage and beam directing assembly relative one another; and the interferometry system of claim 1, 9, or 16 for measuring the position of the stage relative to the beam directing assembly.

22. An interferometry method for use with an interferometry system comprising:

directing two beams along separate paths;

combining the beams to produce an overlapping pair of exit beams, the separate paths defining an optical path length difference;

measuring optical interference between the overlapping pair of exit beams to produce an interference signal s(t) indicative of the optical path length difference, the signal s(t) including a dominant term having a frequency equal to the sum of the frequency splitting ω between the two beams, if any, and a Doppler shift φ defined by the rate of change of the optical path length difference, wherein properties of the interferometry system causes the signal s(t) to further include additional terms each having a frequency not equal to the sum of the frequency splitting ω and the Doppler shift φ;

applying a window function to a sequence of values of the signal s(t);

Fourier transforming the windowed sequence of values, the Fourier transform defining a power spectrum equal to the square modulus of the Fourier transform; and identifying at least one of the additional terms based on at least one peak in the power spectrum at a frequency not equal to the sum of the frequency splitting ω and the Doppler shift φ.

23. An interferometry method for use with an interferometry system comprising:

directing two beams along separate paths;

combining the beams to produce an overlapping pair of exit beams, the separate paths defining an optical path length difference;

measuring optical interference between the overlapping pair of exit beams to produce an interference signal s(t) indicative of the optical path length difference, the signal s(t) including a dominant term having a frequency equal to the sum of the frequency splitting ω between the two beams, if any, and a Doppler shift φ defined by the rate of change of the optical path length difference, wherein properties of the interferometry system causes the signal s(t) to further include additional terms each having a frequency not equal to the sum of the frequency splitting ω and the Doppler shift φ;

tracking the value of the Doppler shift based on the signal s(t);

calculating the frequency $\omega'_v$ of one of the additional terms based on the tracked value of the Doppler shift;

generating a first tuned-filter signal equal to $s(t)\cos(\omega'_{84} t)$ and a second tuned-filter signal equal to $s(t)\sin(\omega'_{84} t)$; and passing the tuned-filter signals through a low-pass filter to quantify the additional term corresponding to $\omega'_v$.

24. An interferometry method for use with an interferometry system comprising:

directing two beams along separate paths;

combining the beams to produce an overlapping pair of exit beams, the separate paths defining an optical path length difference;

measuring optical interference between the overlapping pair of exit beams to produce an interference signal s(t) indicative of the optical path length difference, the signal s(t) including a dominant term having a frequency equal to the sum of the frequency splitting ω between the two beams, if any, and a Doppler shift φ defined by the rate of change of the optical path length difference, wherein properties of the interferometry system causes the signal s(t) to further include additional terms each having a frequency not equal to the sum of the frequency splitting ω and the Doppler shift φ;

providing a quantification for at least some of the additional terms;

Fourier transforming at least one set of values of s(t); and estimating a value for the optical path length difference based on the amplitude and phase of the Fourier transform at the frequency $\omega+\dot\phi$ and values of the quantification for the additional terms that contribute to the Fourier transform at the frequency $\omega+\dot\phi$ based on the Doppler shift $\dot\phi$ corresponding to the set of values of s(t).

25. A lithography method comprising:

supporting a wafer on a stage;

imaging spatially patterned radiation onto the wafer;

adjusting the position of the stage relative to the imaged radiation; and using the interferometry method of claim 22, 23, or 24 to measure the relative position of the stage.

26. A lithography method comprising:

supporting a wafer on a stage;

directing radiation from a source through a mask to produce spatially patterned radiation;

positioning the mask relative to the radiation;

using the interferometry method of claim 22, 23, or 24 to measures the position of the mask relative to the radiation; and imaging the spatially patterned radiation onto the wafer.

27. A beam writing method comprising:

providing a write beam to pattern a substrate;

supporting the substrate on a stage;

delivering the write beam to the substrate;

positioning the stage relative to the write beam; and using the interferometry method of claim 22, 23, or 24 to measure the relative position of the stage.

* * * * *

UNITED STATES PATENT AND TRADEMARK OFFICE
CERTIFICATE OF CORRECTION

PATENT NO. : 6,246,481 B1  
DATED : June 12, 2001  
INVENTOR(S) : Henry A. Hill, Ph.D.

Page 1 of 1

It is certified that error appears in the above-identified patent and that said Letters Patent is hereby corrected as shown below:

<u>Column 66</u>  
Line 44, "s(t) cos($\omega'_{84} t$)" should be -- s(t) cos($\bar{\omega}'_v t$) --;  
Line 45, "s(t) sin($\omega'_{84} t$)" should be -- s(t) sin($\bar{\omega}'_v t$) --;

Signed and Sealed this

Ninth Day of April, 2002

*Attest:*

*Attesting Officer*

JAMES E. ROGAN  
*Director of the United States Patent and Trademark Office*

UNITED STATES PATENT AND TRADEMARK OFFICE
CERTIFICATE OF CORRECTION

PATENT NO.    : 6,246,481 B1
DATED         : June 12, 2001
INVENTOR(S)   : Henry A. Hill, Ph.D.

It is certified that error appears in the above-identified patent and that said Letters Patent is hereby corrected as shown below:

Title page,
Item [56], References Cited, U.S. PATENT DOCUMENTS, please add the following:
-- 4,948,254    08/1990    Ishida
   5,331,400    7/1994     Wilkening et al.
   5,404,222    4/1995     Lis
   5,483,343    1/1996     Iwamoto et al.
   6,008,902    12/1999    Rinn --
FOREIGN PATENT DOCUMENTS, please add the following:
-- 351078       12/1995    Japan (Abstract Only)
   117083       04/1996    Japan (Abstract Only) --
OTHER PUBLICATIONS, please add the following:
-- Badami V.G. et al., "Investigation of Nonlinearity in High Accuracy Heterodyne Laser Interferometry," 1997 PROCEEDINGS, Vol. 16, pp. 153-156.
Wu, C.M. et al., "Analytical Modeling of the Periodic Nonlinearity in Heterodyne Interferometry," APPLIED OPTICS, Vol. 37, No. 28, 1 October 1998, pp. 6696-6700.
Oka K. et al., "Polarization Heterodyne Interferometry Using Another Local Oscillator Beam," OPTICS COMMUNICATIONS, 92 (1992), 1-5.
Hines, B. et al., "Sub-Nanometer Laser Metrology - Some Techniques and Models," JET PROPULSION LABORATORY, CALIFORNIA INSTITUTE OF TECHNOLOGY, pp. 1195-1204.
Bobroff, N., "Recent Advances in Displacement Measuring Interferometry," MEASUREMENT SCIENCE & TECHNOLOGY, Vol. 4, No. 9, September 1993, pp. 907-926.

Column 3,
Lines 42, 46 and 65, replace "$\overset{..}{\phi}$" with -- $\dot{\phi}$ --.
Lines 66, replace "$s(t) \cos(\omega t+\phi+\zeta_{1,0,1,0})+NL$" with -- $s(t) \propto \cos(\omega t+\phi+\zeta_{1,0,1,0})+NL$ --.

Column 4,
Lines 1, 36, 37 and 47, replace "$\phi$" with -- $\varphi$ --.

Line 56, replace "$\omega$" with -- $\tilde{\omega}$ --.

Lines 59 and 66, replace "$\omega$" with -- $\tilde{\omega}$ --. (both occurrences).

Line 67, replace "$\omega$" with -- $\tilde{\omega}$ --. (first and second occurrences).

UNITED STATES PATENT AND TRADEMARK OFFICE
CERTIFICATE OF CORRECTION

PATENT NO. : 6,246,481 B1  
DATED : June 12, 2001  
INVENTOR(S) : Henry A. Hill, Ph.D.

It is certified that error appears in the above-identified patent and that said Letters Patent is hereby corrected as shown below:

<u>Column 5,</u>
Lines 1 and 3, replace "$\omega$" with -- $\tilde{\omega}$ -- (second occurrence).

Line 4, replace "$\omega$" with -- $\tilde{\omega}$ -- (third occurrence).

Lines 4, 9, 42 and 47, replace "$\dot{\phi}$" with -- $\dot{\varphi}$ --.

Line 5, replace "$\omega$" with -- $\tilde{\omega}$ -- (first occurrence).

Line 6, replace "$\dot{\phi}$" with -- $\dot{\varphi}$ -- (both occurrences).

Line 31, replace "$\omega$" with -- $\tilde{\omega}$ -- (both occurrences).

Lines 41 and 48, "$\phi$" with -- $\varphi$ --.
Line 42, replace "s(t)" with -- s(t)$\propto$ --.
Lines 42 and 64, replace "$\phi$" with -- $\varphi$ -- (both occurrences).

<u>Column 6,</u>
Lines 1, 2, 24, 28 and 29, replace "$\phi$" with -- $\varphi$ --.

Lines 2, 5, 9, 24, 29, 34, 38, 55 and 59, replace "$\dot{\phi}$" with -- $\dot{\varphi}$ --.

<u>Column 7,</u>
Line 9, replace "in it)." with -- in s(t). --.

Line 19, replace "$\dot{\phi}$" with -- $\dot{\varphi}$ -- (all occurrences).

Line 38, replace "$\dot{\phi}$" with -- $\dot{\varphi}$ --.

<u>Column 8,</u>
Lines 57 and 62, replace "$\dot{\phi}$" with -- $\dot{\varphi}$ --.

<u>Column 9,</u>
Lines 3, 10, 42 and 47, replace "$\dot{\phi}$" with -- $\dot{\varphi}$ --.

Lines 50, 52, 53, 55 and 59, replace "$\omega$" with -- $\tilde{\omega}$ --.

<u>Column 10,</u>
Lines 24, 29, 34, 36, 37, 43 and 44, replace "$\dot{\phi}$" with -- $\dot{\varphi}$ --.

UNITED STATES PATENT AND TRADEMARK OFFICE
CERTIFICATE OF CORRECTION

PATENT NO. : 6,246,481 B1
DATED : June 12, 2001
INVENTOR(S) : Henry A. Hill, Ph.D.

It is certified that error appears in the above-identified patent and that said Letters Patent is hereby corrected as shown below:

Column 11,
Lines 28, 33, 53 and 58, replace "$\overset{.}{\phi}$" with -- $\dot{\varphi}$ --.

Column 12,
Lines 12, 33, 37, 44 and 60, replace "$\overset{.}{\phi}$" with -- $\dot{\varphi}$ --.

Lines 62, 64, 65 and 67, replace "ω" with -- $\tilde{\omega}$ --.

Column 13,
Lines 11, 15 and 20, replace "$\overset{.}{\phi}$" with -- $\dot{\varphi}$ --.

Line 22, replace "$\overset{.}{\phi}$" with -- $\dot{\varphi}$ -- (both occurrences).

Column 16,
Lines 26 and 33, replace "φ" with -- φ -- (both occurrences).
Lines 32, 34 and 43, replace "φ" with -- φ --.

Lines 33 and 34, replace "$\overset{.}{\phi}$" with -- $\dot{\varphi}$ --.

Column 17,
Lines 5, 7, 12, 16, 22 and 46, replace "φ" with -- φ --.

Lines 44, 47, 52, 54, 62 and 64, replace "$\overset{.}{\phi}$" with -- $\dot{\varphi}$ --.

Line 49, replace "$\overset{.}{\phi}$" with -- $\dot{\varphi}$ -- (all occurrences).

Column 18,
Lines 1, 31, 38, 40, 42, 46, 50, 62 and 65, replace "$\overset{.}{\phi}$" with -- $\dot{\varphi}$ --.
Lines 4, 14, 23, 27, 28, 30 and 58, replace "φ" with -- φ --.

Column 19,
Lines 3 and 5, replace "φ" with -- φ --.
Lines 6 and 35, replace "$\overset{.}{\phi}$" with -- $\dot{\varphi}$ --.

Line 8, replace "φ" with -- $\tilde{\varphi}$ --.

Line 8, replace "ψ" with -- $\tilde{\psi}$ --.

Line 10, replace "φ" with -- $\tilde{\varphi}$ -- (both occurrences).

Line 10, replace "ψ" with -- $\tilde{\psi}$ -- (second occurrence).

UNITED STATES PATENT AND TRADEMARK OFFICE
CERTIFICATE OF CORRECTION

PATENT NO. : 6,246,481 B1
DATED : June 12, 2001
INVENTOR(S) : Henry A. Hill, Ph.D.

It is certified that error appears in the above-identified patent and that said Letters Patent is hereby corrected as shown below:

Column 22,
Lines 57 and 62, replace "$\phi$" with -- $\varphi$ --.

Column 23,
Line 38, replace "$\phi$" with -- $\varphi$ --.
Line 44, replace "$\geqq$" with -- $\geq$ --.

Column 24,
Line 8, replace "$\dot{\phi}$" with -- $\dot{\varphi}$ --.

Lines 40 and 43, replace "$\phi$" with -- $\varphi$ --.

Column 25,
Lines 8, 18, 31, 32, 35 and 52, replace "$\omega$" with -- $\tilde{\omega}$ -- (both occurrences).

Lines 14, 40, 42 and 43, replace "$\omega$" with -- $\tilde{\omega}$ --.

Line 27, replace "$\omega$" with -- $\tilde{\omega}$ -- (second occurrence).

Line 39, replace "$\omega$" with -- $\tilde{\omega}$ -- (all occurrences).

Line 41, replace "$\dot{\phi}$" with -- $\dot{\varphi}$ -- (both occurrences).

Line 43, replace "$\dot{\phi}$" with -- $\dot{\varphi}$ -- (all occurrences).

Lines 43 and 44, replace "$\phi$" with -- $\varphi$ --.

Lines 44, 63 and 64, replace "$\dot{\phi}$" with -- $\dot{\varphi}$ --.

Column 26,
Lines 35, 36, 39, 42, 45, 52 and 56, replace "$\dot{\phi}$" with -- $\dot{\varphi}$ --.

Lines 48 and 54, replace "$\dot{\phi}$" with -- $\dot{\varphi}$ -- (both occurrences).

Column 27,
Lines 17, 35 and 37, replace "$\phi$" with -- $\varphi$ --.
Line 24, replace "$\dot{\phi}$" with -- $\dot{\varphi}$ --.
Lines 49 and 52, replace "$\phi$" with -- $\varphi$ -- (both occurrences).
Line 63, after "(t)-" insert -- $\beta$ --.

UNITED STATES PATENT AND TRADEMARK OFFICE
CERTIFICATE OF CORRECTION

PATENT NO. : 6,246,481 B1
DATED : June 12, 2001
INVENTOR(S) : Henry A. Hill, Ph.D.

It is certified that error appears in the above-identified patent and that said Letters Patent is hereby corrected as shown below:

Column 28,
Line 30, replace "$\phi$" with -- $\varphi$ --.

Column 29,
Line 7, replace "=" with -- + -- (second occurrence).
Line 18, replace "xf" with -- $x^n$ --.
Lines 24 and 37, replace "$\omega$" with -- $\tilde{\omega}$ -- (both occurrences).

Lines 26, 29, 31, 33 and 35, replace "$\phi$" with -- $\varphi$ --.

Lines 36, 41 and 61, replace "$\dot{\phi}$" with -- $\dot{\varphi}$ --.

Line 57, replace "$\dot{\phi}$" with -- $\dot{\varphi}$ -- (both occurrences).

Column 30,
Lines 58, 59 and 61, replace "$\omega$" with -- $\tilde{\omega}$ --.

Line 63, replace "$\dot{\phi}$" with -- $\dot{\varphi}$ --.

Column 31,
Line 17, replace "$\phi$" with -- $\varphi$ --.

Line 34, replace "$\dot{\phi}$" with -- $\dot{\varphi}$ --.

Line 58, replace "$\geqq$" with -- $\geq$ --.

Line 58, replace "$\omega$" with -- $\tilde{\omega}$ -- (first occurrence).

Column 32,
Line 13, replace "$\omega$" with -- $\tilde{\omega}$ --.

Line 23, replace "O2T" with -- $\omega_{2,T}$ --.

Line 27, replace "$\dot{\phi}$" with -- $\dot{\varphi}$ --.

Column 33,
Line 23, replace "$\phi$" with -- $\varphi$ -- (both occurrences).
Lines 44 and 46, replace "$\phi$" with -- $\varphi$ --.

UNITED STATES PATENT AND TRADEMARK OFFICE
CERTIFICATE OF CORRECTION

PATENT NO. : 6,246,481 B1
DATED : June 12, 2001
INVENTOR(S) : Henry A. Hill, Ph.D.

It is certified that error appears in the above-identified patent and that said Letters Patent is hereby corrected as shown below:

Column 34,
Lines 15 and 57, replace " $\dot{\phi}$ " with -- $\dot{\varphi}$ --.

Line 53, replace " $\dot{\phi}$ " with -- $\dot{\varphi}$ -- (both occurrences).

Lines 65 and 67, replace "$\phi$" with -- $\varphi$ --.

Column 35,
Line 17, replace " $\dot{\phi}$ " with -- $\dot{\varphi}$ --.

Column 37,
Lines 1, 3, 7 and 11, replace "$\phi$" with -- $\varphi$ --.
Line 44, replace "))" with -- ) --.

Column 38,
Lines 16 and 43, replace "$\phi$" with -- $\varphi$ --.

Column 39,
Lines 24, 37 and 38, replace "$\phi$" with -- $\varphi$ --.
Line 35, replace "$\phi$" with -- $\varphi$ -- (both occurrences).

Column 40,
Lines 32 and 34, replace "$\phi$" with -- $\varphi$ -- (both occurrences).

Line 55, replace "$\omega$" with -- $\tilde{\varphi}$ --.
Line 61, replace "$\omega$" with -- $\tilde{\omega}$ -- (both occurrences).
Line 62, replace "$\omega$" with -- $\tilde{\omega}$ --.

Column 41,
Lines 1, 5, 27 and 28, replace "$\omega$" with -- $\tilde{\omega}$ --.

Line 14, replace "$\omega$" with -- $\tilde{\omega}$ -- (second occurrence).
Lines 17, 18, 22 and 37, replace "$\omega$" with -- $\tilde{\omega}$ -- (both occurrences).
Line 27, replace "$\omega$" with -- $\tilde{\omega}$ --.

Lines 19, 20, 51, 65 and 67, replace "$\phi$" with -- $\varphi$ --.

Line 29, replace " $\dot{\phi}$ " with -- $\dot{\varphi}$ -- (both occurrences).

UNITED STATES PATENT AND TRADEMARK OFFICE
CERTIFICATE OF CORRECTION

PATENT NO. : 6,246,481 B1
DATED : June 12, 2001
INVENTOR(S) : Henry A. Hill, Ph.D.

It is certified that error appears in the above-identified patent and that said Letters Patent is hereby corrected as shown below:

Column 41 (cont'd),

Line 30, replace "$\dot{\phi}$" with -- $\dot{\varphi}$ -- (all occurrences).

Line 58, replace "$\dot{\phi}$" with -- $\dot{\varphi}$ --.

Line 67, replace "$\phi$" with -- $\tilde{\varphi}$ --.

Column 42,
Lines 6, 9, 10 and 64, replace "$\phi$" with -- $\varphi$ --.
Lines 7 and 8, replace "$\phi$" with -- $\varphi$ -- (both occurrences).

Column 43,
Lines 1, 5, 6, 16 and 23, replace "$\phi$" with -- $\varphi$ --.

Column 45,
Lines 2, 4 and 9, replace "$\phi$" with -- $\varphi$ --.
Line 6, replace "$\phi$" with -- $\varphi$ -- (both occurrences).

Column 46,
Line 20, replace "$W_{wm}$" with -- $W_m$ --.
Line 24, after "$W_{m,1}$" insert -- $\neq$ --.
Line 33, replace "$\xi$" with -- $f$ -- .
Lines 31, 41 and 46, replace "$\phi$" with -- $\varphi$ --.

Column 47,
Lines 1, 4 and 5, replace "$\phi$" with -- $\varphi$ -- (both occurrences).
Lines 8, 18, 49 and 61, replace "$\theta$" with -- $\vartheta$ --.
Lines 61, replace "$\phi$" with -- $\varphi$ --.

Column 48,
Lines 48, 64 and 65, replace "$\theta$" with -- $\vartheta$ --.
Line 49, replace "$Q$" with -- $Q$ -- (both occurrences).
Line 52, replace "32" with -- = --.
Line 52, replace "104" with -- $\psi$ --.
Line 62, replace "$Q_{104}$" with -- $Q$ --.

Lines 62 and 64, replace "$\Phi$" with -- $\tilde{\Phi}$ --.

Line 63, replace "$\theta$" with -- $\tilde{\vartheta}$ -- (both occurrences).

UNITED STATES PATENT AND TRADEMARK OFFICE
CERTIFICATE OF CORRECTION

PATENT NO. : 6,246,481 B1
DATED : June 12, 2001
INVENTOR(S) : Henry A. Hill, Ph.D.

It is certified that error appears in the above-identified patent and that said Letters Patent is hereby corrected as shown below:

<u>Column 49,</u>
Line 10, after "4" insert -- | --.
Line 31, replace "Q" with -- $Q$ --.
Lines 33 and 42, replace "ϕ" with -- φ -- (first occurrences).

Lines 33 and 42, replace "ϕ" with -- $\tilde{\varphi}$ --. (second occurrence).

Line 47, replace "ϕ" with -- φ -- (both occurrences).
Line 51, after "φ" insert -- 5 --.

<u>Column 51,</u>
Line 24, replace "96" with -- $\tilde{\varphi}_6$ --.

Line 30, replace "ϕ" with -- $\tilde{\varphi}$ --.

Line 44, replace "a" with -- $\tilde{\varphi}$ --.

Line 44, replace "O" with -- $\tilde{\Phi}$ --.

Line 46, replace "5" with -- $\tilde{\varphi}$ --.

Line 46, replace "4" with -- $\tilde{\Phi}$ --.

Line 54, replace "96=6-6t" with -- $\tilde{\varphi}_6 = a_6 - w_6 t$ --.

Line 54, replace "97=07-07t" with -- $\tilde{\varphi}_7 = a_7 - w_7 t$ --.

Line 54, replace "6" with -- $a_6$ --.
Line 55, replace "a?" with -- $a_7$ --.
Line 56, replace "3" with -- $a_3$ --.
Line 58, replace "ZIPM" with -- $Z_{\psi,M}$ --.
Line 59, replace "QI,M" with -- $Q_{\psi,M}$ --.
Line 63, replace "104" with -- ψ --.

<u>Column 52,</u>
Lines 8, 10, 13 and 31, replace "Φ" with -- $\tilde{\Phi}$ --.
Line 23, replace "θ" with -- ϑ --.

Line 31, replace "θ" with -- $\tilde{\vartheta}$ --

Line 31, replace "ϕ" with -- φ --.

UNITED STATES PATENT AND TRADEMARK OFFICE
CERTIFICATE OF CORRECTION

PATENT NO.    : 6,246,481 B1
DATED         : June 12, 2001
INVENTOR(S)   : Henry A. Hill, Ph.D.

It is certified that error appears in the above-identified patent and that said Letters Patent is hereby corrected as shown below:

Column 53,
Lines 11, 14 and 23, replace "$\varphi$" with -- $\tilde{\varphi}$ --.

Lines 19, 22 and 24, replace "$\Phi$" with -- $\tilde{\Phi}$ --.

Lines 18 and 23, repalce "$\theta$" with -- $\tilde{\vartheta}$ --

Line 45, replace "$\dot{\phi}$" with -- $\dot{\varphi}$ --.

Column 54,
Line 62, replace "$\dot{\phi}$" with -- $\dot{\varphi}$ --.

Column 55,
Line 36, replace "$\dot{\phi}$" with -- $\dot{\varphi}$ --.

Column 56,
Lines 31, 32 and 42, replace "$\dot{\phi}$" with -- $\dot{\varphi}$ --.

Lines 44, 45, 47, 48 and 55, replace "$\omega$" with -- $\tilde{\omega}$ --.

Lines 49 and 59, replace "$\omega$" with -- $\tilde{\omega}$ -- (both occurrences).

Line 56, replace "$\omega$" with -- $\tilde{\omega}$ -- (second occurrence).

Column 57,
Line 25, replace "$\omega$" with -- $\tilde{\omega}$ --.

Lines 25 and 42, replace "$\dot{\phi}$" with -- $\dot{\varphi}$ --.

Line 44, replace "(5))" with -- (5) --.
Lines 59 and 63, "$\phi$" with -- $\varphi$ --.

Column 58,
Lines 24 and 25, replace "$\dot{\phi}$" with -- $\dot{\varphi}$ --.

Line 35, replace "$\phi$" with -- $\tilde{\varphi}$ --.

Lines 38, 40, 41 and 44, replace "$\phi$" with -- $\varphi$ --.

UNITED STATES PATENT AND TRADEMARK OFFICE
CERTIFICATE OF CORRECTION

PATENT NO.     : 6,246,481 B1
DATED          : June 12, 2001
INVENTOR(S)    : Henry A. Hill, Ph.D.

It is certified that error appears in the above-identified patent and that said Letters Patent is hereby corrected as shown below:

Column 63,
Lines 16, 21, 30 and 60, replace "$\dot{\phi}$" with -- $\dot{\varphi}$ --.

Column 64,
Lines 7, 12 and 64, replace "$\dot{\phi}$" with -- $\dot{\varphi}$ --.

Lines 16, 19, 20, 22 and 24, replace "ω" with -- $\tilde{\omega}$ --.

Column 65,
Lines 2, 9, 16 and 17, replace "$\dot{\phi}$" with -- $\dot{\varphi}$ --.

Line 11, replace "$\dot{\phi}$" with -- $\dot{\varphi}$ --. (both occurrences).

Column 66,
Line 6, replace "φ" with -- φ --.

Lines 12, 21, 33, 39, 61 and 67, replace "$\dot{\phi}$" with -- $\dot{\varphi}$ --.

Lines 42 and 48, replace "ω" with -- $\tilde{\omega}$ --.

Column 67,
Lines 6, 8 and 9, replace "$\dot{\phi}$" with -- $\dot{\varphi}$ --.

Signed and Sealed this

Eighth Day of July, 2003

JAMES E. ROGAN
*Director of the United States Patent and Trademark Office*